United States Patent
Sazonov et al.

(10) Patent No.: US 10,736,566 B2
(45) Date of Patent: Aug. 11, 2020

(54) FOOD INTAKE MONITOR

(71) Applicant: The Board of Trustees of The University of Alabama, Tuscaloosa, AL (US)

(72) Inventors: Edward Sazonov, Northport, AL (US); Muhammad Farooq, Tuscaloosa, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 346 days.

(21) Appl. No.: 15/895,781

(22) Filed: Feb. 13, 2018

(65) Prior Publication Data

US 2018/0242908 A1 Aug. 30, 2018

Related U.S. Application Data

(60) Provisional application No. 62/458,160, filed on Feb. 13, 2017.

(51) Int. Cl.
*A61B 5/00* (2006.01)
*A61B 5/12* (2006.01)
(Continued)

(52) U.S. Cl.
CPC ............ *A61B 5/4866* (2013.01); *A61B 5/002* (2013.01); *A61B 5/036* (2013.01); *A61B 5/1118* (2013.01);
(Continued)

(58) Field of Classification Search
CPC ...... H04R 1/1016; H04R 3/00; H04R 3/0005; H04R 25/652; H04R 2225/023;
(Continued)

(56) References Cited

U.S. PATENT DOCUMENTS 5,263,491 A 11/1993 Thornton
6,135,950 A 10/2000 Adams
(Continued)

FOREIGN PATENT DOCUMENTS

WO 2008023374 2/2008

OTHER PUBLICATIONS

Bedri, et al., "A Wearable System for Detecting Eating Activities with Proximity Sensors in the Outer Ear", In: Proceedings of the 2015 ACM International Symposium on Wearable Computers [Internet]. New York, NY, USA: ACM; 2015 [cited Dec. 22, 2015]. p. 91-92. Available from: http://doi.acm.org/10.1145/2802083.2808411.

(Continued)

*Primary Examiner* — Xu Mei
(74) *Attorney, Agent, or Firm* — Meunier Carlin & Curfman LLC

(57) ABSTRACT

Systems and methods for monitoring food intake include an air pressure sensor for detecting ear canal deformation, according to some implementations. For example, the air pressure sensor detects a change in air pressure in the ear canal resulting from mandible movement. Other implementations include systems and methods for monitoring food intake that include a temporalis muscle activity sensor for detecting temporalis muscle activity, wherein at least a portion of the temporalis muscle activity sensor is coupled adjacent a temple portion of eyeglasses and disposed between the temple tip and the frame end piece. The temporalis muscle activity sensor may include an accelerometer, for example, for detecting movement of the temple portion due to mandibular movement from chewing.

20 Claims, 31 Drawing Sheets

(51) Int. Cl.

| | |
|---|---|
| *A61B 90/00* | (2016.01) |
| *A61B 5/11* | (2006.01) |
| *G16H 20/60* | (2018.01) |
| *G06N 3/08* | (2006.01) |
| *G09B 19/00* | (2006.01) |
| *G09B 5/06* | (2006.01) |
| *A61B 5/03* | (2006.01) |
| *G16H 40/63* | (2018.01) |
| *G06N 7/00* | (2006.01) |
| *A61B 7/00* | (2006.01) |
| *G06N 5/04* | (2006.01) |
| *G06N 5/00* | (2006.01) |
| *H04R 3/00* | (2006.01) |

(52) U.S. Cl.
CPC .............. *A61B 5/12* (2013.01); *A61B 5/4542* (2013.01); *A61B 5/6803* (2013.01); *A61B 5/6817* (2013.01); *A61B 5/7246* (2013.01); *A61B 5/7264* (2013.01); *A61B 5/7278* (2013.01); *A61B 7/001* (2013.01); *A61B 90/361* (2016.02); *G06N 3/08* (2013.01); *G06N 7/005* (2013.01); *G09B 5/06* (2013.01); *G09B 19/0092* (2013.01); *G16H 20/60* (2018.01); *G16H 40/63* (2018.01); *A61B 5/1123* (2013.01); *A61B 5/486* (2013.01); *A61B 5/7285* (2013.01); *A61B 5/742* (2013.01); *A61B 2562/0204* (2013.01); *A61B 2562/0219* (2013.01); *A61B 2562/0247* (2013.01); *A61B 2562/168* (2013.01); *G06N 5/003* (2013.01); *G06N 5/048* (2013.01); *H04R 3/002* (2013.01)

(58) Field of Classification Search
CPC .......... H04R 2225/025; H04R 2460/13; A61B 5/4866; A61B 90/361; A61B 5/002; A61B 5/036; A61B 5/1118; A61B 5/12; A61B 5/6803; A61B 5/6817; A61B 5/7246; A61B 5/7264; A61B 5/7278; A61B 5/1123; A61B 5/486; A61B 5/7285; A61B 5/742; A61B 7/001; A61B 2562/0204; A61B 2562/0219; A61B 2562/0247; A61B 2562/168; G16H 40/63; G16H 20/60; G06N 3/08; G06N 5/003; G06N 5/048; G06N 7/005
USPC ...... 381/95, 26, 328, 151, 91, 122; 181/130; 600/559, 586, 590
See application file for complete search history.

(56) References Cited

U.S. PATENT DOCUMENTS

| | | | | |
|---|---|---|---|---|
| 6,647,368 | B2* | 11/2003 | Nemirovski | H04B 1/3877 600/300 |
| 6,735,477 | B2* | 5/2004 | Levine | A61B 5/0031 607/40 |
| 8,696,616 | B2 | 4/2014 | Baynham | |
| 9,168,000 | B2 | 10/2015 | Dunki-Jacobs et al. | |
| 10,006,896 | B2* | 6/2018 | Fernstrom | G01N 33/02 |
| 10,102,342 | B1* | 10/2018 | Vleugels | G16H 20/60 |
| 2002/0022774 | A1* | 2/2002 | Karnieli | G06F 19/324 600/300 |
| 2005/0017602 | A1 | 1/2005 | Arms et al. | |
| 2006/0064037 | A1 | 3/2006 | Shalon et al. | |
| 2009/0012433 | A1 | 1/2009 | Fernstorm | |
| 2010/0194573 | A1 | 8/2010 | Hoover et al. | |
| 2011/0125063 | A1 | 5/2011 | Shalon | |
| 2011/0276312 | A1 | 11/2011 | Shalon et al. | |
| 2013/0267794 | A1 | 10/2013 | Fernstorm | |
| 2014/0275748 | A1 | 9/2014 | Dunki-Jacobs | |
| 2014/0294193 | A1* | 10/2014 | Tikander | H04R 3/02 381/74 |
| 2016/0012749 | A1 | 1/2016 | Connor | |
| 2016/0073953 | A1* | 3/2016 | Sazonov | A61B 5/7267 600/590 |
| 2016/0132642 | A1* | 5/2016 | Carmi | G06F 3/017 348/77 |
| 2016/0148535 | A1* | 5/2016 | Ashby | G09B 19/0092 434/127 |
| 2019/0272845 | A1* | 9/2019 | Hasan | H04R 1/08 |

OTHER PUBLICATIONS

Bedri, et al., "Detecting Mastication: A Wearable Approach", Proceedings of the 2015 ACM on International Conference on 10 Multimodal Interaction [Internet]; New York, NY, USA: ACM 2015 [cited Dec. 7, 2015] p. 247-250. (ICMI 2015).

Black, et al., "Critical evaluation of energy intake data using fundamental principles of energy physiology: 2. Evaluating the results of published surveys", Eur J Clin Nutr. Dec. 1991;45(12):583-99.

Champagne, et al. "Energy Intake and Energy Expenditure: A Controlled Study Comparing Dietitians and Non-dietitians", J Am Diet Assoc. 2002;102(10):1428-32.

Day, et al., "Epidemiological assessment of diet: a comparison of a 7-day diary with a food frequency questionnaire using urinary markers of nitrogen, potassium and sodium", International Journal of Epidemiology. Apr. 1, 2001;30(2):309-17.

De Castro JM. "Methodology, Correlational Analysis, and Interpretation of Diet Diary Records of the Food and Fluid Intake of Free-living Humans", Appetite. Oct. 1994;23(2):179-92.

Doulah, et al., "Meal Microstructure Characterization from Sensor-Based Food Intake Detection," Front. Nutr., vol. 4, 2017, Article 31, 10 pages.

Farooq, et al., "A Novel Wearable Device for Food Intake and Physical Activity Recognition," Sensors, vol. 16, No. 7, p. 1067, Jul. 2016.

Fontana, et al., "Automatic Ingestion Monitor: A Novel Wearable Device for Monitoring of Ingestive Behavior," IEEE Trans. Biomed. Eng., vol. 61, No. 6, pp. 1772-1779, Jun. 2014.

Fontana, et la., "A robust classification scheme for detection of 25 food intake through non-invasive monitoring of chewing," in 2012 Annual International Conference of the IEEE Engineering in Medicine and Biology Society (EMBC), pp. 4891-4894, 2012.

Kaczkowski, et al., "Four-Day Multimedia Diet Records Underestimate Energy Needs in Middle-Aged and Elderly Women as Determined by Doubly-Labeled Water", The Journal of Nutrition. 130(4):802-5, Apr. 1, 2000.

Karantonis, et al., "Implementation of a real-time human movement classifier using a triaxial accelerometer for ambulatory monitoring," IEEE Trans. Inf. Technol. Biomed., vol. 10, No. 1, pp. 156-167, Jan. 2006.

Lee, et al., "Exercise intensity and longevity in men: The Harvard Alumni Health Study," J. Am. Med. Assoc., vol. 273, No. 15, pp. 1179-1184, 1995.

Livingstone, et al., "Markers of the validity of reported energy intake", J Nutr. 133 Suppl 3:895S-920S, Mar. 2003.

Peng, et al., "Feature selection based on mutual information: criteria of max-dependency, max-relevance, and min-redundancy," IEEE Trans. Pattern Anal. Mach. Intell., vol. 27, No. 8, pp. 1226-1238, 2005.

Prentice, et al., "Metabolism or appetite: questions of energy balance with particular reference to obesity", J Hum Nutr Diet. Apr. 1989, 2(2):95-104.

Sazonov, et al., "A Sensor System for Automatic Detection of Food Intake Through Non-Invasive Monitoring of Chewing," IEEE Sens. J., vol. 12, No. 5, pp. 30 1340-1348, May 2012.

Sazonov, et al., "Non-invasive monitoring of chewing and swallowing for objective quantification of ingestive behavior", Physiological Measurement. 29: 525-541, Nov. 2008.

Wang, et al., "CARE: Chewing Activity Recognition Using Non-invasive Single Axis Accelerometer", In: Adjunct Proceedings of

(56) References Cited

OTHER PUBLICATIONS the 2015 ACM International Joint Conference on Pervasive and Ubiquitous Computing and Proceedings of the 2015 ACM International Symposium on Wearable Computers [Internet]. New York, NY, USA: ACM; 2015 p. 109-112. Available from: http://doi.acm.org/10.1145/2800835.2800884.

Zhang, et al., "Diet eyeglasses: Recognising food chewing using EMG and smart eyeglasses", In: 2016 IEEE 13th International Conference on Wearable and Implantable Body Sensor Networks (BSN). 2016. p. 7-12.

Office Action issued in co-pending U.S. Appl. No. 14/845,855, dated Jan. 11, 2017.

Office Action issued in co-pending U.S. Appl. No. 14/845,855, dated Sep. 7, 2017.

Office Action issued in co-pending U.S. Appl. No. 14/845,855, dated Mar. 30, 2018.

* cited by examiner

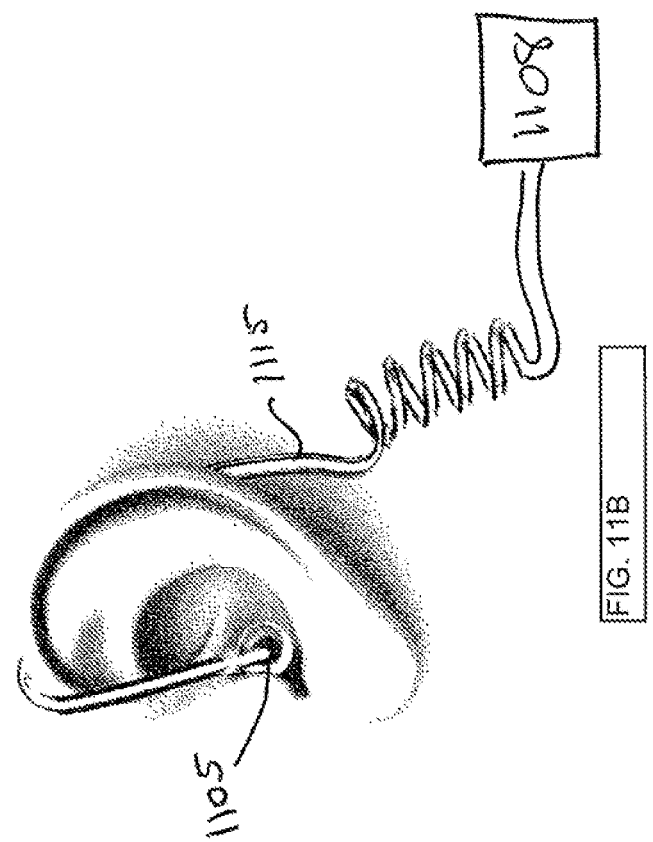
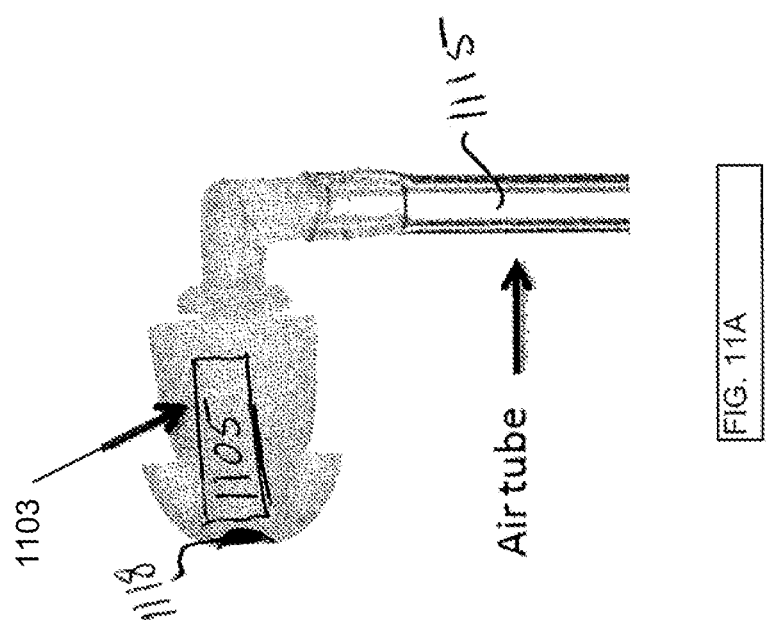

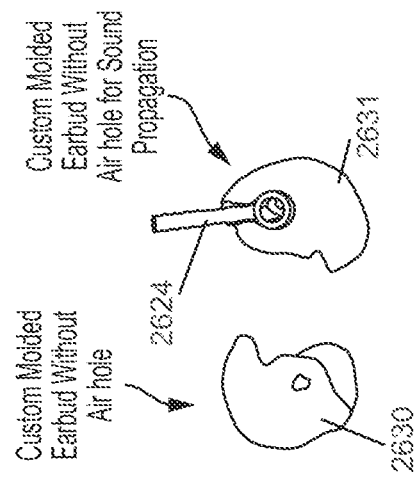
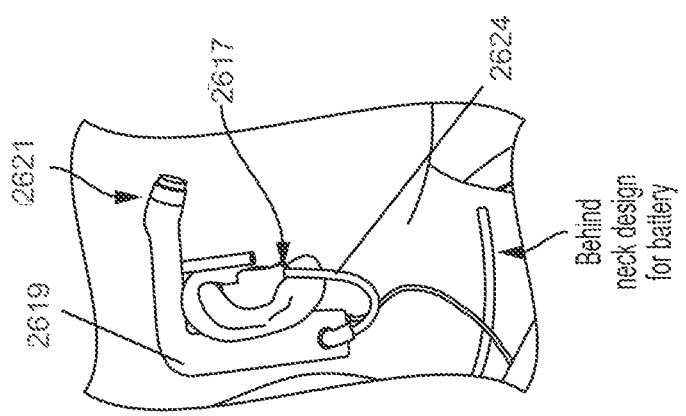
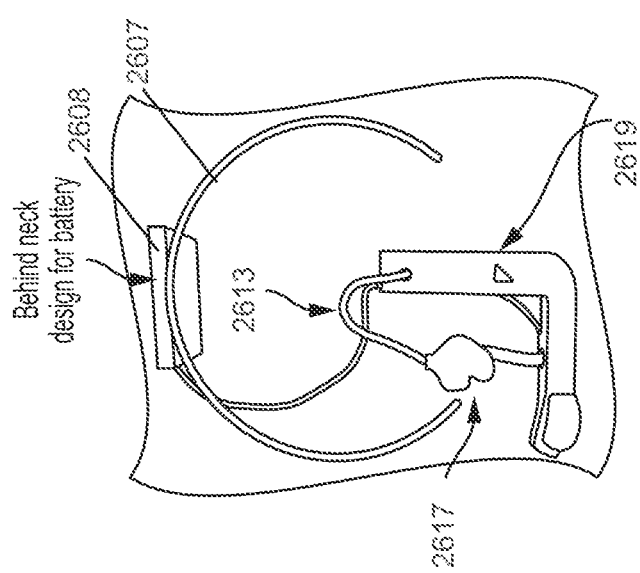
FIG. 26C
FIG. 26B
FIG. 26A

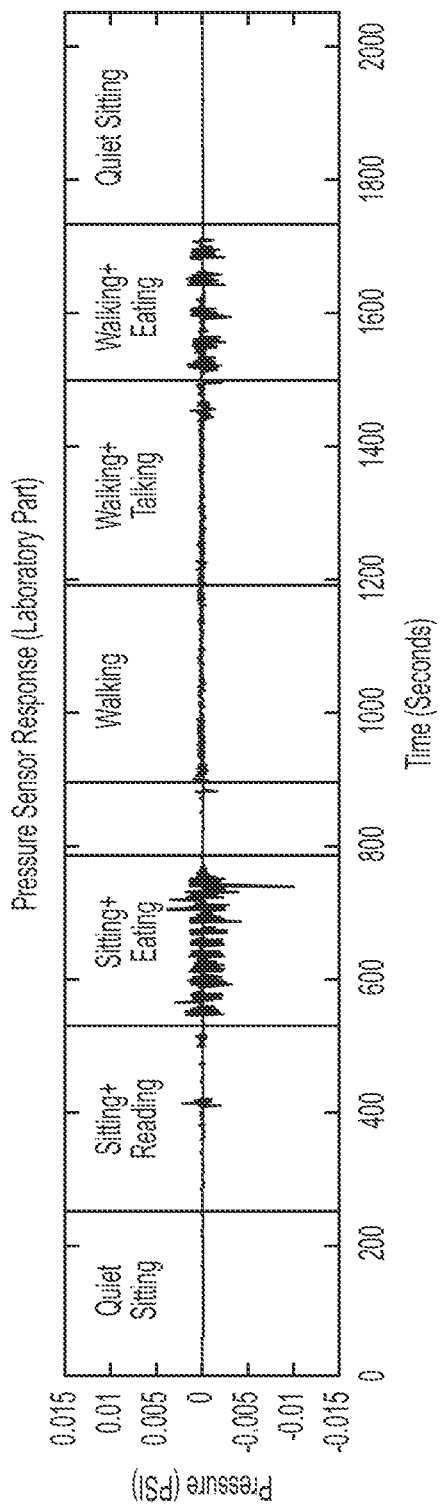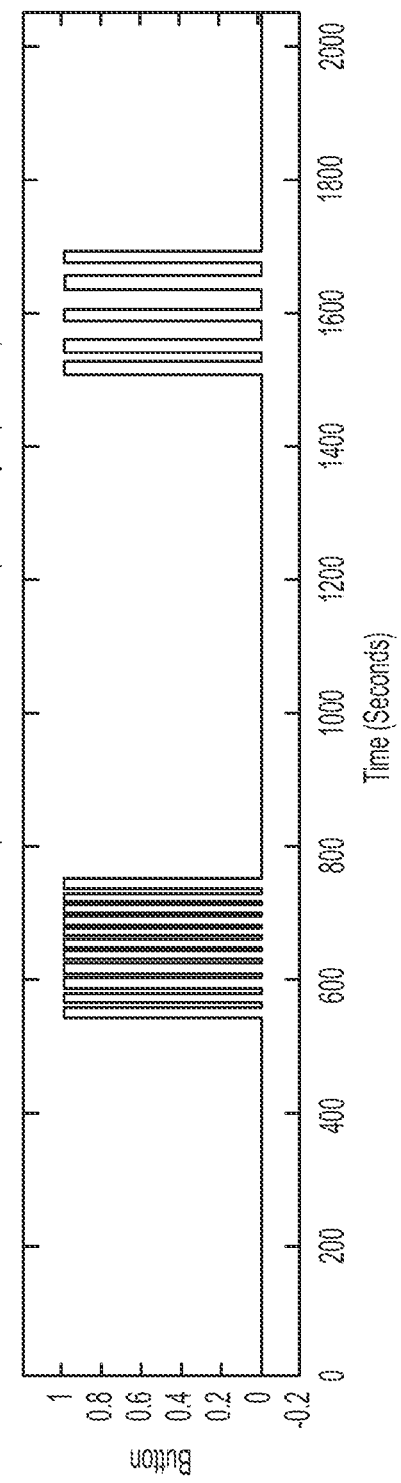
FIG. 27A
FIG. 27B

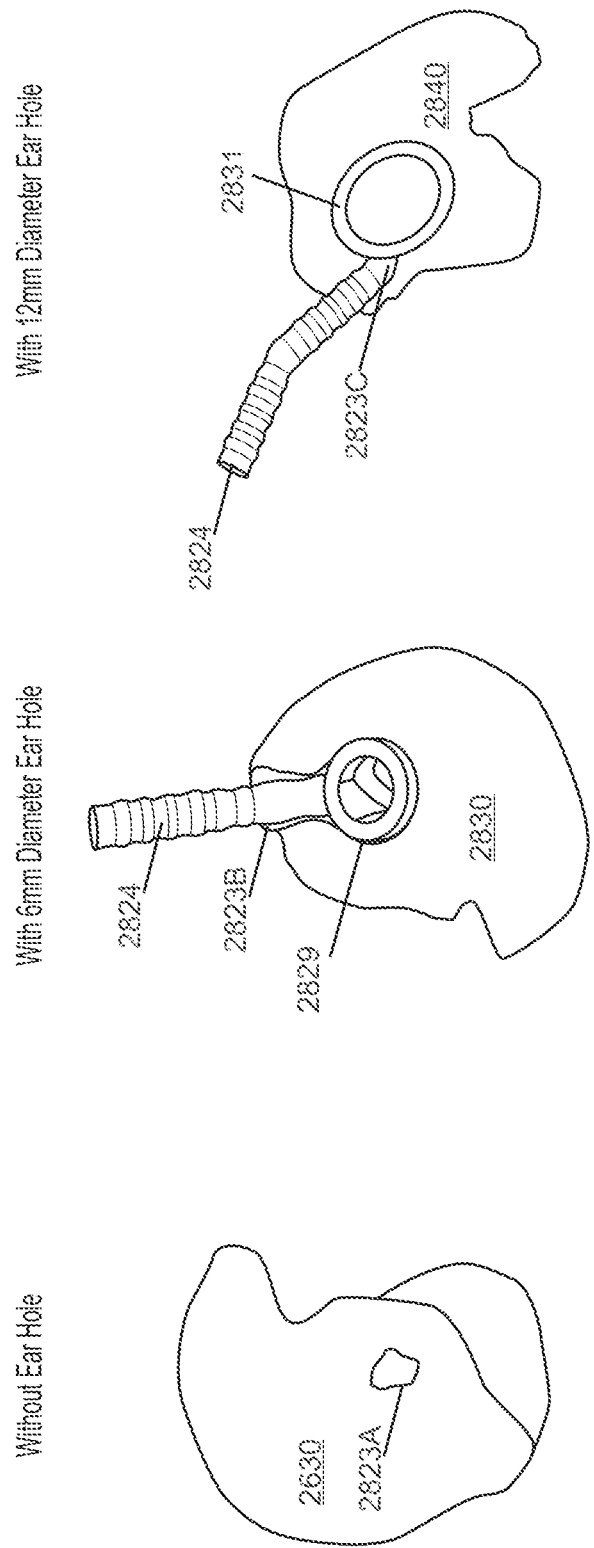

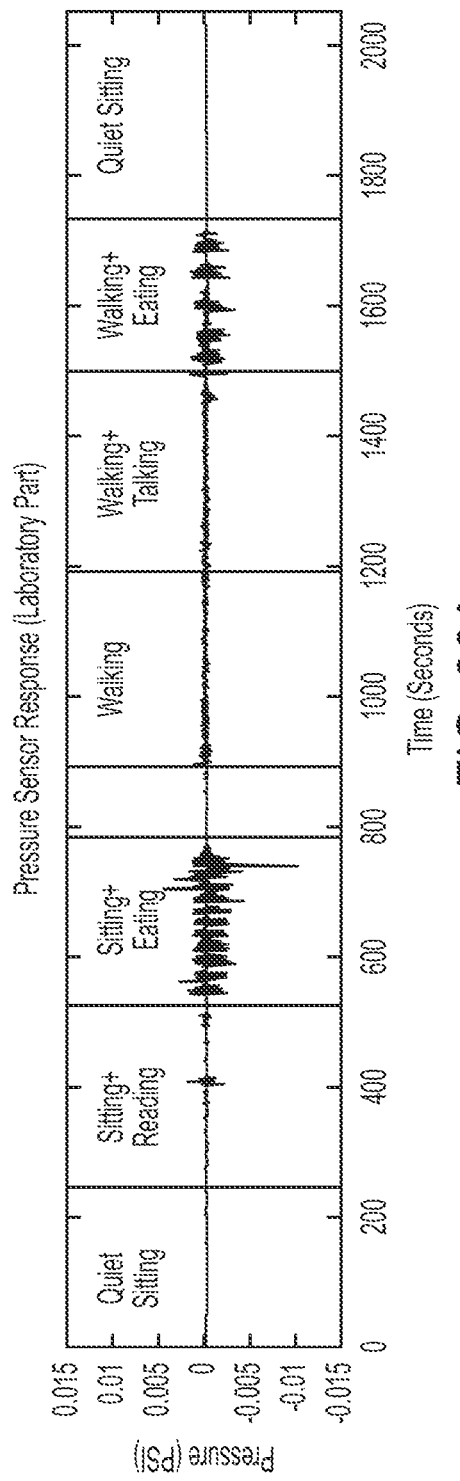
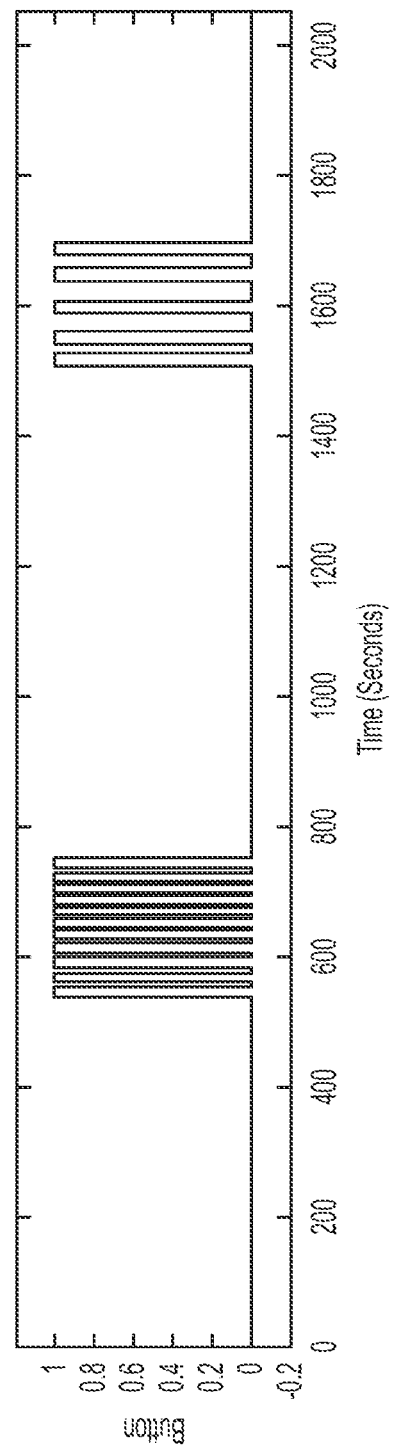
FIG. 30A
FIG. 30B

FOOD INTAKE MONITOR

CROSS REFERENCE TO RELATED APPLICATIONS

This application claims the benefit of priority to U.S. Provisional Application No. 62/458,160 filed Feb. 13, 2017, the disclosure of which is incorporated herein by reference in its entirety.

BACKGROUND

The prevalence of obesity in developed countries is increasing at an alarming rate. Obesity contributes to an increased risk of heart disease, hypertension, diabetes, and some cancers and is now considered a risk factor for cardiovascular disease. Millions of people are attempting to lose weight at any time, but the rate of success at preventing weight regain remains low.

The research community devotes a significant effort toward studying effects of energy intake and expenditure on energy balance and weight gain. A fundamental baseline for each person measures how much consumed food and associated calories are required for effective weight loss or gain. Various techniques have been used to record food intake, including keeping a personal record or using a software application on a personal computer, PDA or smartphone. These techniques, however, rely on a user to record or take pictures of every meal and the portions received, which proves unlikely in practice. Other techniques have sought to automatically monitor food intake. For example, a wearable system may listen for the sound of a person swallowing or chewing to determine the rate of food consumption or count the number of hand-to-mouth gestures ("bites"). Even these wearable systems, however, are either too imprecise (such as sound-based approaches) or require input from a user (such as the hand gesture counters). A user must turn the gesture counter on or off when consuming a meal to avoid the possibility of falsely recording consumption of food throughout the day. Furthermore, many of the eyeglass-based sensors for food intake detection require direct contact of the sensors with skin and are attached using medical adhesive (e.g. EMG or strain sensors). This limits the usability of the devices and might cause discomfort to the user. These approaches are also sensitive to the placement of the sensors that require careful placement on a specific location such as temporalis muscle.

Other embodiments have attempted to incorporate accelerometers into hardware used for monitoring food consumption. Due to the limited number of activities and lack of motion from the activities of daily living, the full potential of using accelerometers on the eyeglasses was not explored. In addition, most of the published studies relying on eyeglass sensors for detection of food intake were limited to the controlled laboratory conditions and their performance was not evaluated in unconstrained free-living environment.

Another technique attempting to record food intake relies on an optical ear canal deformation sensor which receives information from three infrared proximity sensors to measure the deformation. A three-dimensional gyroscope is used to measure the motion of the body. However, in this system, the sensor blocks the ear canal and interferes with normal hearing, and the optical sensors consume a large amount of power. These limitations prevent the implementation of a truly wearable device.

At the present time there is no accurate, inexpensive, non-intrusive way to objectively quantify energy intake in free living conditions and study behavioral patterns of food consumption.

SUMMARY

Systems and methods for monitoring food intake include an air pressure sensor for detecting ear canal deformation, according to some implementations. For example, the air pressure sensor detects a change in air pressure in the ear canal resulting from mandible movement. Other implementations include systems and methods for monitoring food intake that include a temporalis muscle activity sensor for detecting temporalis muscle activity, wherein at least a portion of the temporalis muscle activity sensor is coupled adjacent a temple portion of eyeglasses and disposed between the temple tip and the frame end piece. The temporalis muscle activity sensor may include an accelerometer, for example, for detecting movement of the temple portion due to mandibular movement from chewing.

BRIEF DESCRIPTION OF THE DRAWINGS

FIGS. 11A-11B illustrate a first embodiment of a food intake monitor utilizing an ear canal air pressure monitor as disclosed herein.

FIGS. 26A-26C are respective hardware configurations for a food intake monitor for positioning about a wearer's neck and head as described in this disclosure.

FIGS. 27A-27C are respective data plots of pressure sensor data gathered as output from at least one of the hardware configurations for a food intake monitor as disclosed in FIGS. 26A-26C.

FIGS. 28A-28C are respective embodiments of custom ear buds designed for use with the hardware components and sensors of a food intake monitor as disclosed herein.

FIGS. 30A-30B are data plots of pressure sensor outputs from food intake monitors configured according to this disclosure.

DESCRIPTION

Figure 1A:
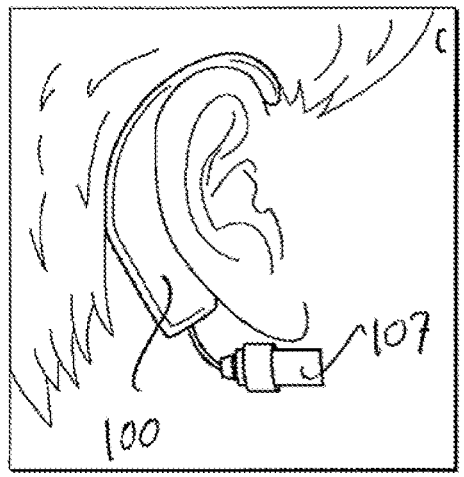
FIGS. 1A-1D illustrates exemplary components for monitoring ingestive behavior according to various implementations.

The disclosed systems and methods provide an automated wearable device for monitoring ingestive behavior, caloric and nutrient intake, and, optionally, modifying ingestive behavior and caloric intake using real-time feedback from the wearable system.

A human can be considered a thermal and mass exchange system. The underlying physical principle is the law of conservation of energy and matter. Conservation of mass under normal conditions over some considerably long period T can be expressed by the following formula taking into account major components:

$$\int_T (M_{FOOD} + M_{O_2}) = \qquad (1)$$

-continued
$$\int_T (M_{WEIGHTGAIN} + M_{CO_2} + M_{Fecal} + M_{Urinary} + M_{Evaporation})$$

Conservation of energy under normal conditions (constant body temperature) for a period T can be expressed by the following formula:

$$\int_T E_{FOOD} = \int_T (E_{MECHWORK} + E_{HEAT} + E_{STORAGE} + E_{WASTE}), \qquad (2)$$

where $E_{FOOD}$ is energy content of food intake (digestible chemical energy+heat energy), $E_{MECHWORK}$ is energy spent for external work (force×distance), $E_{HEAT}$ is energy lost as heat, $E_{STORAGE}$ is energy stored in protein, carbohydrate and fat storage, and $E_{WASTE}$ is chemical energy of food, which was not consumed and lost through excretions.

The systems and methods disclosed herein provide techniques to quantify energy and nutrient intake. Most of the energy intake in humans comes from food. By monitoring chewing (mastication) and swallowing (deglutition), food intake quantities can be estimated. In one exemplary implementation, deglutition (swallowing) can be reliably identified by a device detecting characteristic sounds in the area lateral or caudal to the laryngeal prominence. Deglutition can also be identified by a device detecting characteristic sounds in the mastoid bone, detecting electrical impulses resulting from muscle activation during swallowing, or by detecting changes in electrical impedance of the laryngeal region during swallowing. Mastication (chewing) creates specific motion of the lower jaw that can be identified by a device detecting motion of the mandible and/or skin in the region of the outer ear. Mastication can also be identified by a device detecting characteristic sound in the mastoid bone or ear canal or detecting deformation inside of the ear canal, as well as by detecting electrical signals resulting from muscle activation during jaw motion.

Wearable non-intrusive sensors may detect deglutition through a sound sensor located in the area caudal to the laryngeal prominence. Another exemplary implementation may detect deglutition through a behind-the-ear sound sensor and detect mastication through a behind-the-ear strain sensor. Alternatively, optical, tactile, or magnetic sensors may be used located at various locations around the body. Further, signal processing methods and pattern recognition methods may automatically detect deglutition and mastication. A classification algorithm may utilize signals from mastication and/or deglutition sensors as predictors and identify periods of food consumption, recognize and identify individual foods in the meal, and/or trigger a camera that captures the image of the food being eaten.

FIG. 1A illustrates a first exemplary implementation of a food intake monitor (100) that includes a piezoelectric sensor (107) that may be worn in the area immediately below the outer ear. The sensor may detect changes in the skin curvature created by the characteristic motion of the mandible during chewing of food. In one exemplary implementation, a buffered signal from the sensor may be acquired by a data acquisition system.

Figure 1B:
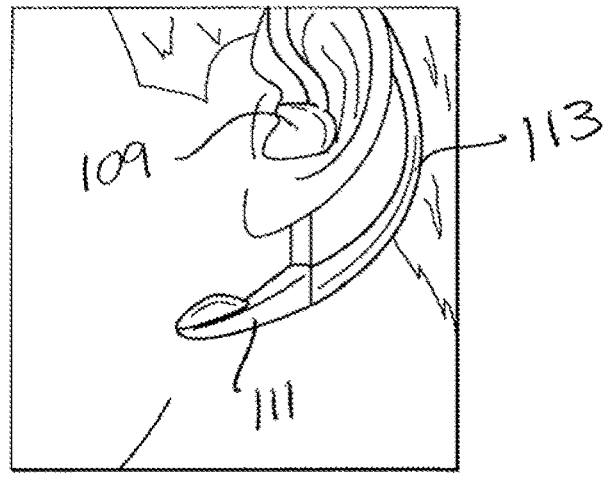
Figure 1C:
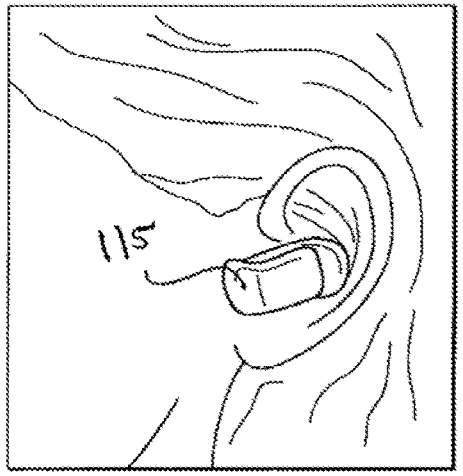
Figure 1D:
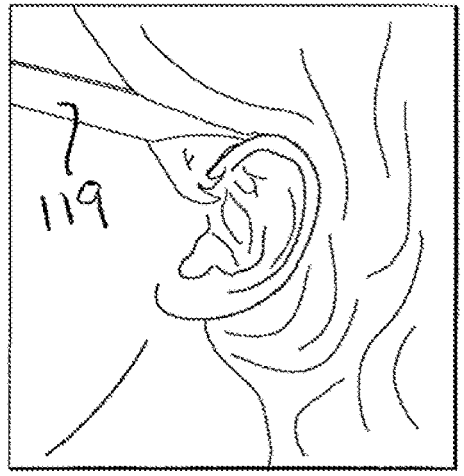

FIGS. 1B and 1C illustrate exemplary implementations that rely on a sound, strain, tactile, optical, or magnetic sensor (109, 112) in a boom (113) of a headset worn over the ear and detect jaw motion or/and include a sensor (115) in the ear canal to detect a chewing sound or deformation of the ear canal. FIG. 1D illustrates another exemplary implementation with the sensors integrated into the frames (119) of eye glasses either directly in front of the ear (straight or curved temples) or behind the ear (temple tips that may be elongated to reach lower ear).

Figure 2A:
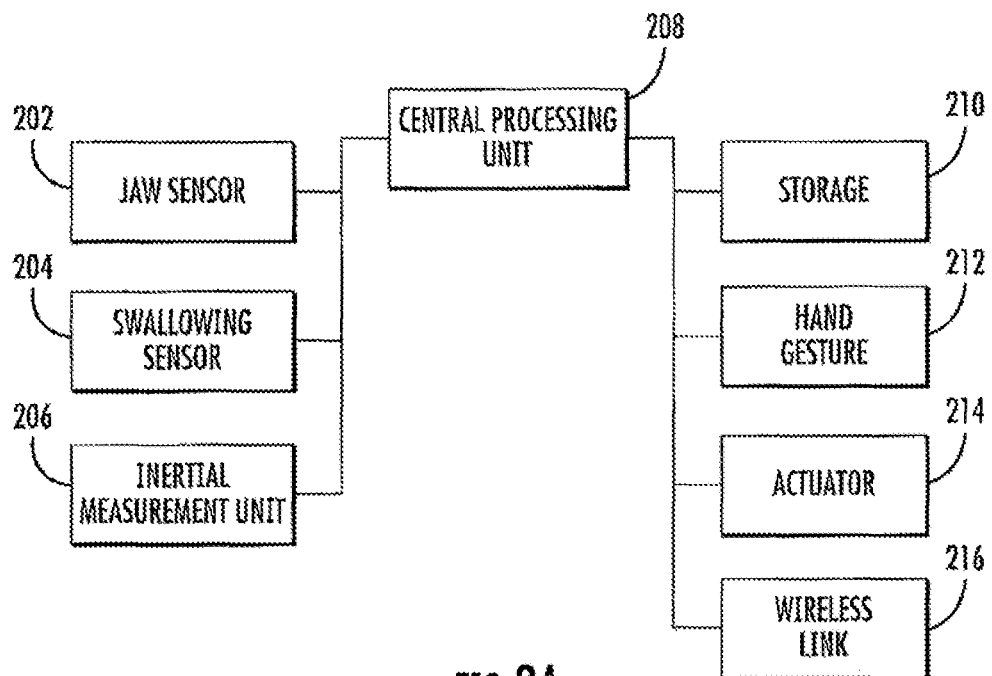
FIG. 2A illustrates an exemplary system for monitoring ingestive behavior.

FIG. 2A illustrates a system including a jaw sensor 202, such as the piezoelectric sensor, strain sensor, magnetic, or optical sensor, a swallowing sensor 204 that detects deglutition by monitoring sounds, mechanical motion, electrical potentials, or electrical signals in the laryngeal area, an inertial measurement unit 206 that detects body motion, a hand gesture sensor 212 that detects hand motion and/or proximity of the hand to the mouth, an actuator 214 (for example, a vibrator or an ear phone) that delivers real-time feedback to the user, and an external wireless link 216 (such as Wi-Fi or Bluetooth) that delivers sensors data and/or food information or imagery to a remote server, such as smart phone, personal computer, or cloud computer. The system need not contain all of the devices 202, 204, 206, 212, 214 and 216, as the system may be configured with fewer than all four sensors and/or without the internal actuator or wireless link to an external device. For example, output from the jaw sensor 202, inertial measurement unit 206, and hand gesture sensor 212 may be combined to detect food consumption, without relying on output from a swallowing sensor 204. Central processing unit 208 may perform signal processing to detect food consumption and store signals and historical trending data in storage 210. The items in FIG. 2 may be connected using an internal wireless link, and one or more of the items may be combined into a single component.

The swallowing sensor 204 may be a microphone specific for this application or one typically used for hands-free radio communications. It may also be a mechanical sensor, such as an accelerometer or strain sensor that detects displacement of the laryngopharynx in the absolute or relative to the inertial measurement unit's 206 frame of reference. It may also be an electrical electrode sensor that detects electrical potentials on the surface of the neck resulting from muscle excitation during swallowing. It may also be an electrical impedance sensor where a small DC or AC current is injected into the transmission electrode and received on the receiver electrode to detect swallowing and passing of the food bolus through the laryngopharynx. The waveform may be digitized by a sound card and a sound recording application at the sampling rate of, for example, 8000 Hz, although other sampling rates may be used. The swallowing sensor 204 may be positioned around the neck or on the mastoid bone behind the ear. The swallowing sensor 204 can be worn as a medallion attached, on a neck band or as a self-adhesive strip, offering a non-intrusive, wearable device that does not need special attention. A swallowing sound has a unique time-frequency pattern that can be identified by pattern recognition methods. Temporary medical adhesives may be used for providing better contact between the sensor and surface of the skin, or utilize an in-ear probe.

In one implementation, jaw sensor 202 may be a piezoelectric, foil, or ink-printed strain sensor that detects the specific motion of the lower jaw by capturing strains created by motion of the posterior border of the mandible's ramus, deformations on the surface of the skin during chewing, or vibrations propagated through the tissues during food crushing while chewing. Such a sensor may be attached to the skin or reside in an enclosure such as the boom in FIG. 1B or FIG. 1C without attachment to the skin but remaining in contact with the skin. In another implementation, jaw sensor 202 may be an optical or magnetic sensor that detects skin surface deformation and/or motion during chewing without direct contact with the skin or body tissues. Such a sensor may or may not need additional optical or magnetic markers placed on the skin below the sensor. In another implementation, jaw sensor 202 may be a tactile sensor that detects skin motion or vibrations from skin that is in the contact but free to slide under the sensor. In another implementation, jaw sensor 202 may be electrical electrodes that detect electrical potentials from jaw muscle actuation during chewing. In some embodiments, the jaw sensor is attached as an adhesive patch below a wearer's outer ear.

These two sensors can be integrated into a single device (208) worn behind the ear in a manner similar to a wireless phone headset, such as an earpiece or in frames of eye glasses. A camera (213) may be incorporated into the single device (208) to assist in tracking food intake as discussed below. No special fittings or positioning of the sensors are required. Further, the sensors may be disguised as or integrated into a headset for a cellular phone.

The inertial measurement unit 206 may contain a microelectromechanical, piezoelectric or other type of accelerometer and/or gyroscope and/or magnetometer. The inertial measurement unit may be sensitive to 1 to 9 dimensions of measurements such as linear acceleration, angular velocity or magnetic field.

In other implementations, an air pressure sensor detects ear canal deformation by detecting a change in air pressure within the ear canal resulting from mandible movement. As shown in prior art embodiments 10A and 10B [1, 2] of the attached figures, earlier versions of a food intake monitor incorporate an air pressure sensor as shown. The ear canal sensor relies on the information from three infrared proximity sensors to measure the deformation. A 3D gyroscope is used to measure the motion of the body. The limitations of the proposed system are that the sensor blocks the ear canal and interferes with normal hearing; the optical sensors consume a large amount of power and prevent implementation of a truly wearable device. During chewing, the mandible location changes, which causes the volume deformation in the ear canal. This volume deformation causes changes in the in-ear pressure, which can be measured by the air pressure sensor.

Beginning with FIG. 11, according to the present disclosure and the embodiments herein, the air pressure sensor (1105) is disposed within an earpiece housing or ear bud (1103) that fits behind the ear lobe or elsewhere outside of the ear canal. The air pressure sensor (1105) is coupled to an air tube (1115) that extends between the air pressure sensor (1105) and an earbud (1103). An inlet (1118) to the earbud is fully or partially inserted into the ear canal. Air from the ear canal travels into the ear bud, through the air tube, and to the air pressure sensor. The air pressure sensor converts pressure variations into voltage variations. The changes in the voltage are measured by a microcontroller (1108), for example, a low power microcontroller (1108). The microcontroller (1108) may also utilize a timer subsystem of the microcontroller. The voltage variation is a signal carrying information that may be used for detection and characterization (such as counting the number of chews or measuring chewing rate) of food intake.

The earbud (1103), in some implementations, leaves the ear canal open, allowing for unobstructed hearing. And, in some implementations, the earbud includes a speaker that allows for discrete delivery of audio information into the user's ear. Exemplary implementations of the air pressure sensor implemented as part of the earbud are described and shown in the attached figures filed herewith.

Ear canal deformation sensors may be implemented as shown in FIG. 11B with the earbud tip (1105) extended to go into the ear canal. Ear canal deformations during chewing are converted into pressure variations by the air tube (1115) connected to the ear bud (1103), and these pressure variations are measured by a pressure sensor (1105). As discussed in more detail below, the ear canal deformation sensor may work as part of a system in conjunction with an accelerometer and may reside in the ear bud body or in an external enclosure proximate to the ear bud body. An enclosure for electronics and a battery, with appropriate transceivers for receiving communications data tracking the ear canal pressure variations and accelerometer output signals, may be located proximate the ear bud (e.g., behind the ear) or integrated into another device (smartphone, mp3 player, Bluetooth headset, etc.).

Figure 12:
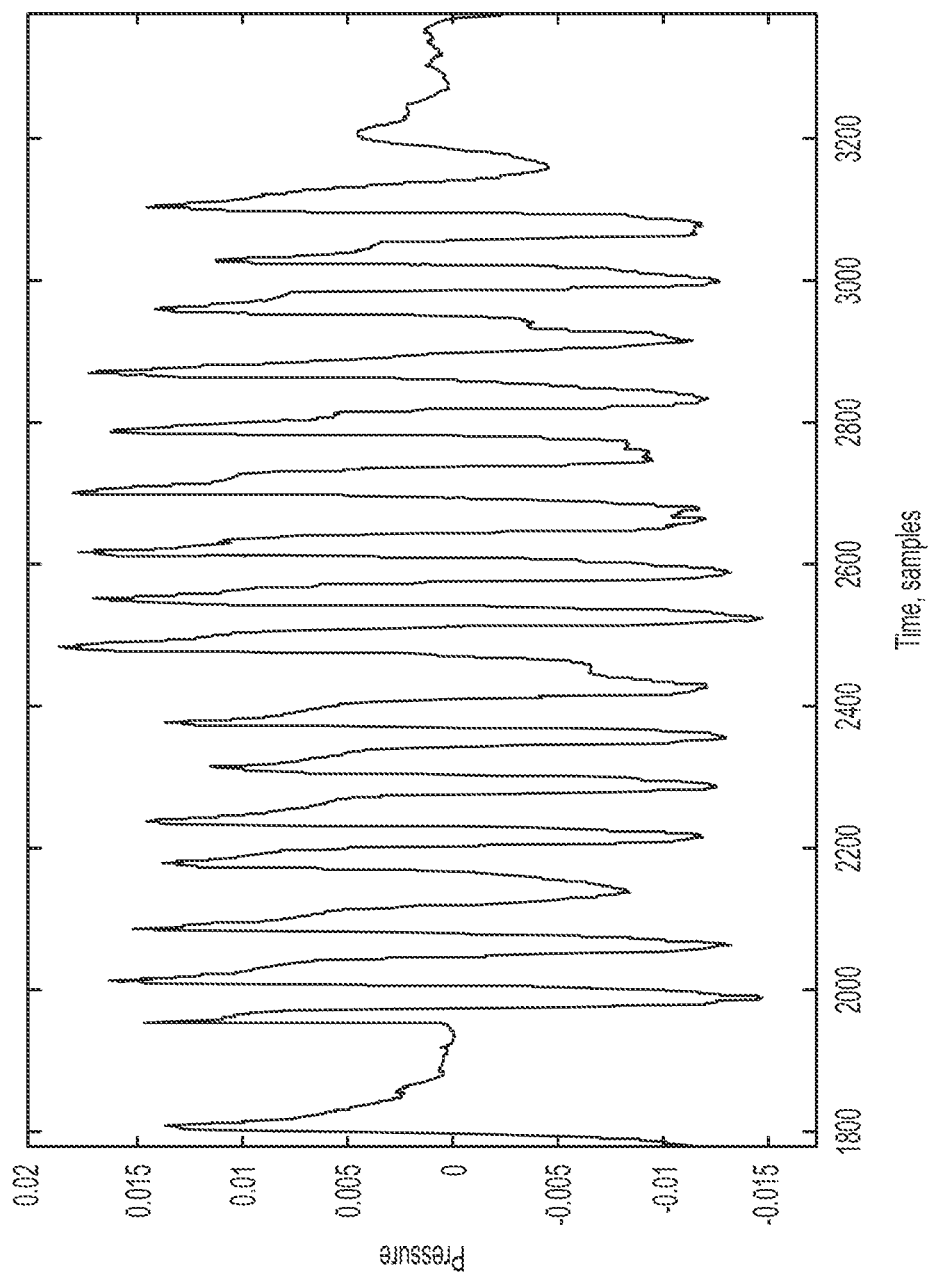
FIG. 12 is a plot of air pressure versus time samples resulting from an air pressure based food intake monitor according to the present disclosure.
Figure 13:
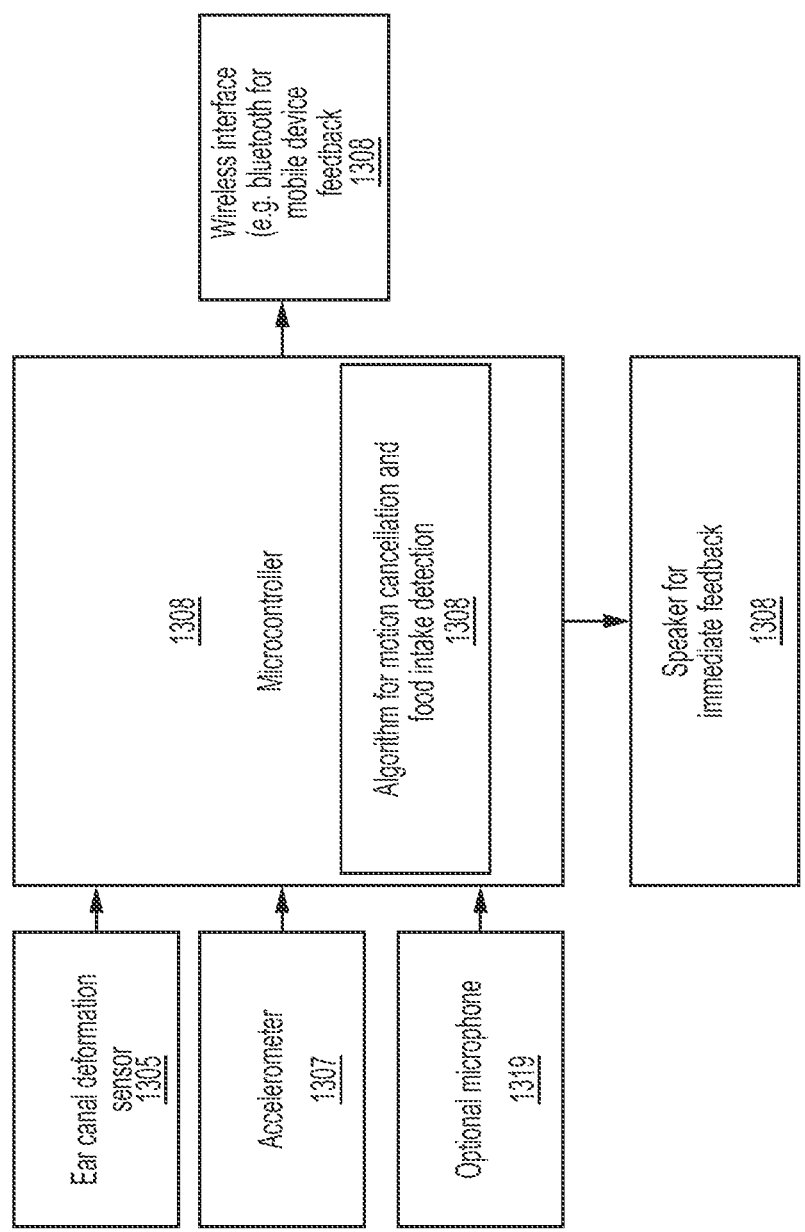
FIG. 13 is a schematic of data communication flow among hardware components of a food intake monitor as disclosed herein.

FIG. 12 illustrates the signal collected by the air pressure sensor (1105), under certain conditions, may be affected by the physical activity of the user and/or intrinsic activities, such as speech. The sampled air pressure indicates periodic changes in ear canal pressure related to mastication, indicating that food is being ingested. In some implementations, such as that illustrated in FIG. 13, additional sensors, such as an accelerometer (1307) and/or a microphone (1309) (discussed below), are also included in the earpiece housing (or elsewhere) with the air pressure sensor (1105, 1305) to improve food intake detection based on ear canal deformation. In addition, in further or alternative implementations, a camera and/or a Bluetooth (or other type of area network) communication device (1315) are included for more expansive options in tracking and identifying food intake. For example, the earpiece housing may include a Bluetooth earpiece housing (1315). In implementations having a camera, the camera may be activated whenever mandible movement associated with food intake is detected by the air pressure sensor and/or other sensors and accompanying algorithm(s).

Figure 14:
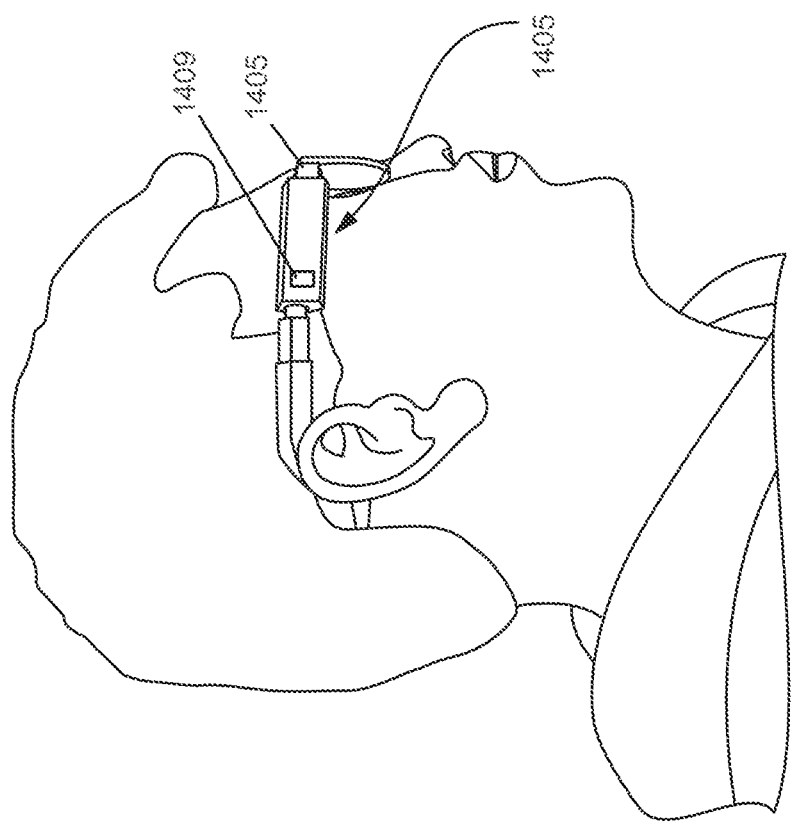
FIG. 14 is a side view of a food intake monitor embodied as a clip on device for attaching to a pair of eyeglasses according to the present disclosure.

In other (or further) implementations such as shown in FIG. 14, a temporalis muscle activity sensor (1409) is used to detect the oscillatory patterns of the thickness of the temporalis muscle for detection of mastication (chewing), due to the temporalis' role as a masticatory muscle during chewing. The contraction and relaxation of the temporalis muscle results in elevation, retraction, and side-to-side grinding movements of the mandible, or lower jawbone, during the mastication cycle. This muscle activity results in approximately 1.2 mm changes of the muscle thickness, with a lower deviation compared with that of the masseter and sternocleidomastoid muscles for adults without temporomandibular disorder. This sensor (1409) may be coupled to eyeglasses to monitor the temporalis muscle activity by measuring the movement of the temple portions of eyeglasses during eating. In the embodiment of FIG. 14, the sensor (1409) (and/or any other sensors described herein), may be embodied in a clip-on architecture that is both attachable and removable from a pair of eyeglasses. The sensor may be disposed on the temple portion of the eyeglasses between the temple tips and the end portions of the frames. In some implementations, beginning with FIG. 15, the sensors that embody a system for food intake monitoring may include a three-dimensional accelerometer (1508), which measures the acceleration forces caused by the movements of the temporalis muscle during eating.

The accelerometer signal from the temple portion (1503) of the glasses is highly correlated with the temporalis muscles activity during eating, which suggest that the accelerometer is responding to the eating activity. Similarly, the accelerometer (1508) may be used for detection and monitoring of physical activity of the user, such as walking. Signal processing algorithms, such as noise cancellation techniques or individual component analysis, may be used to de-correlate the signals to improve food intake recognition. The signal from the accelerometer (1508) may also be used to recognize specific activities performed by the user (e.g., sedentary, ambulatory) and estimate energy expenditure of the user.

Figure 15A:
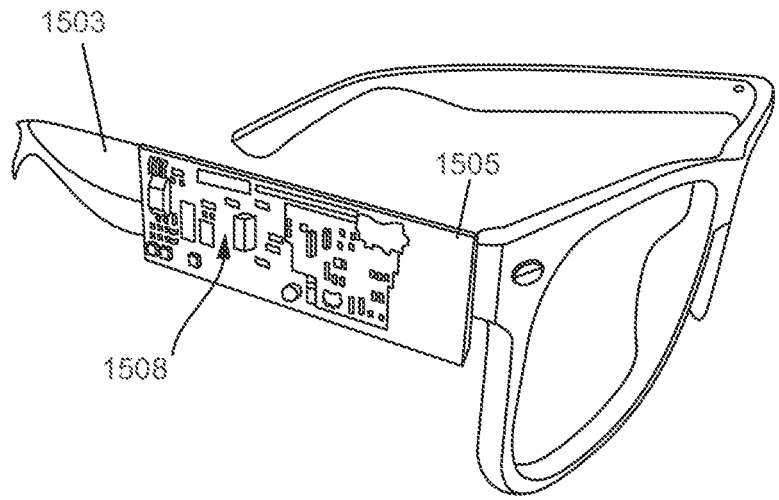
FIGS. 15A-15B are each a side perspective view of a circuit board encompassing an accelerometer in an embodiment of a food intake monitor for use with a pair of eyeglasses as disclosed herein.
Figure 15B:
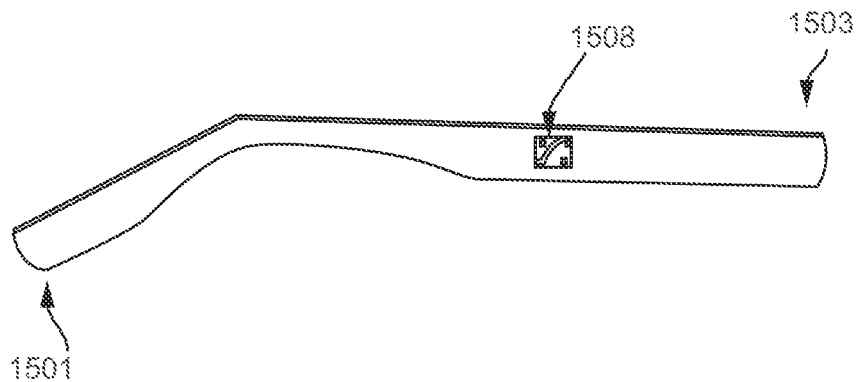
Figure 16:
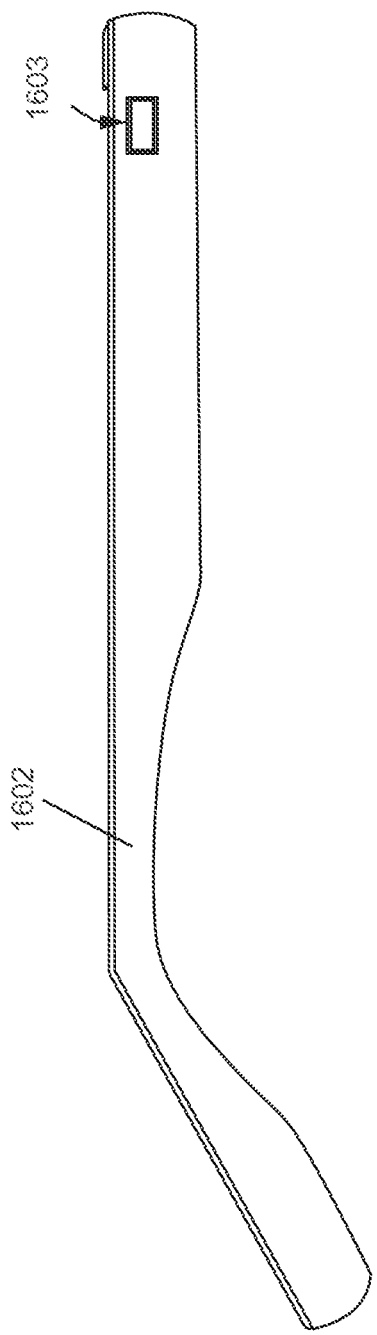
FIG. 16 is a side plan view of an example position for an accelerometer in an embodiment of a food intake monitor for use with a pair of eyeglasses as disclosed herein.

The accelerometer embodiments of a food intake monitor associated with eyeglasses as shown in FIGS. 15 and 16 allow for accelerometer-based devices that capture head or other body movements, which help in developing to identify eating from other activities and improve the reliability of food intake detection. The use of a 3D accelerometer (1508, 1603) attached to the frame (1602) of regular glasses avoids direct sensor attachment to the body and issues associated with incorrect sensor placement and poor body contact. Such attachment also ensures that the device can potentially be removed and reattached to a wide variety of regular glasses and no expertise is required to wear the glasses as might be needed for other sensor attachments.

Figure 17:
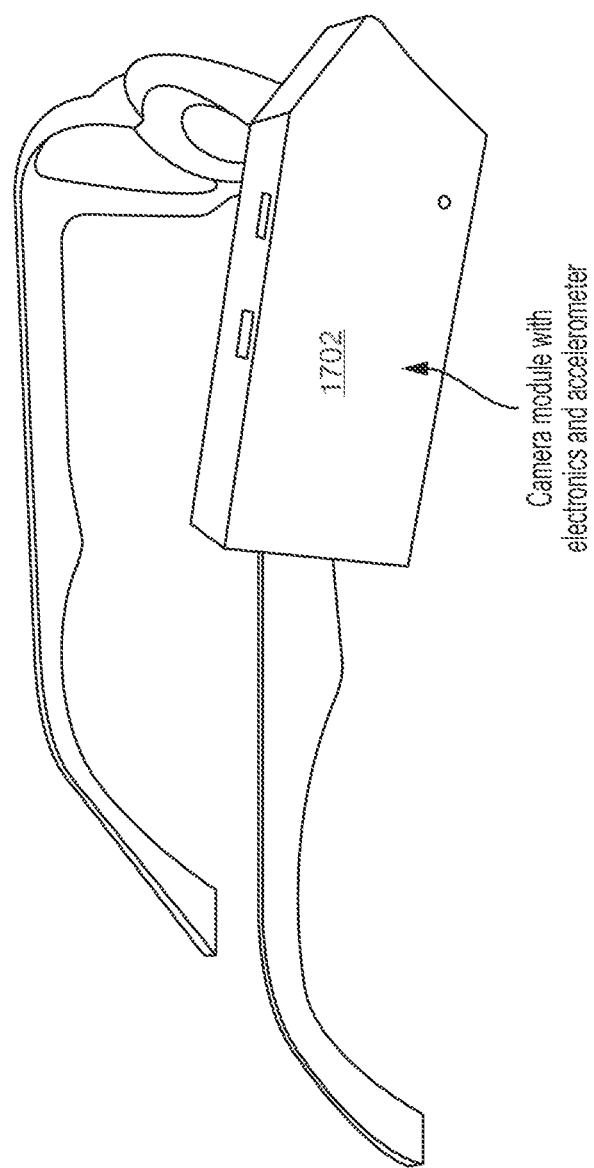
FIG. 17 is a side plan view of an example position for a camera in an embodiment of a food intake monitor for use with a pair of eyeglasses as disclosed herein.
Figure 18:
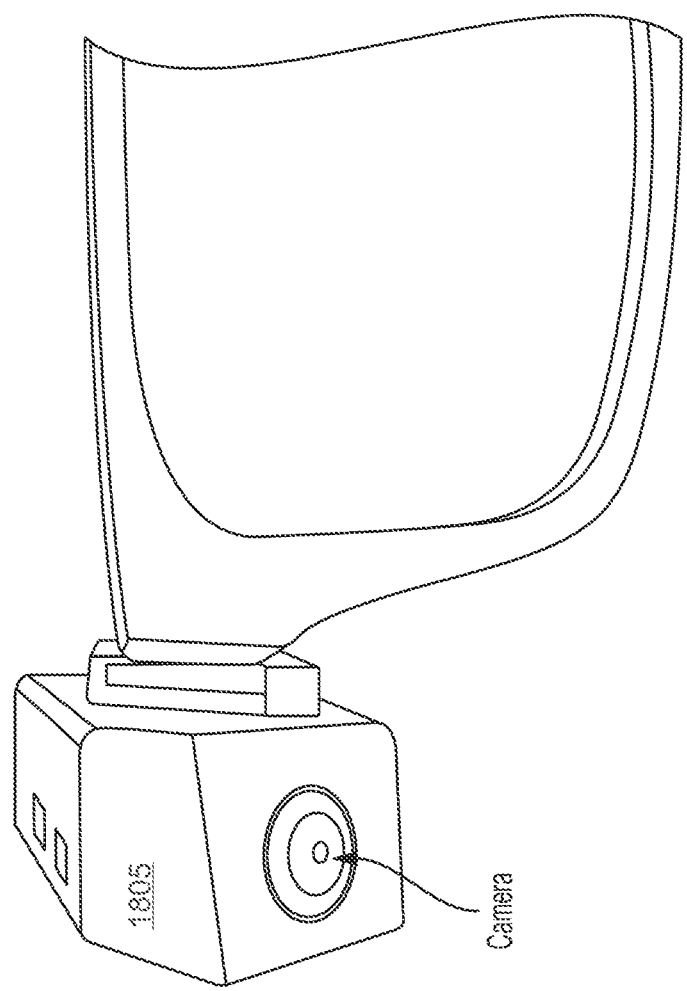
FIG. 18 is a front plan view of the embodiment of a food intake monitor with a camera according to FIG. 17.
Figure 19:
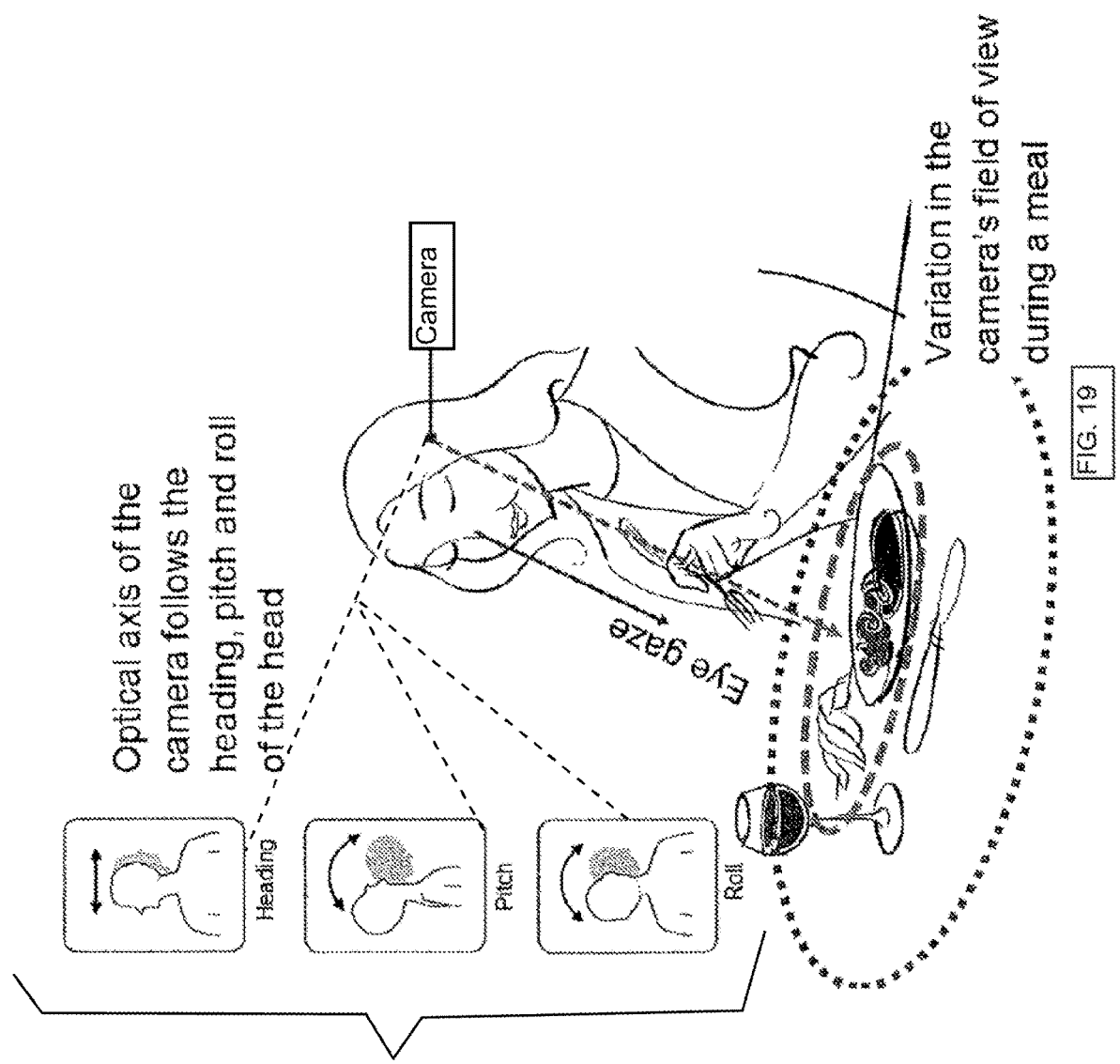
FIG. 19 is a schematic view of a food intake monitor as described herein and data gathering for images taken with a camera relative to a user's line of sight.
Figure 20:
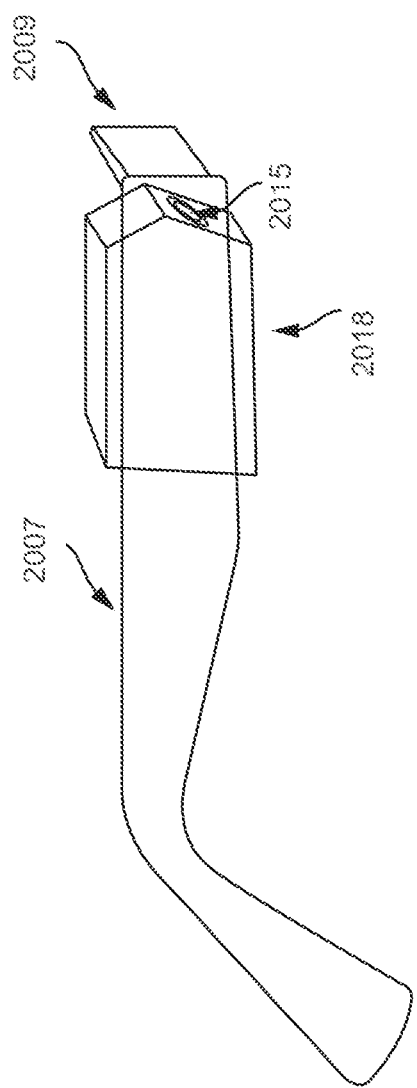
FIG. 20 is a side plan view of an example position for a camera in an embodiment of a food intake monitor for use with a pair of eyeglasses as disclosed herein.
Figure 21:
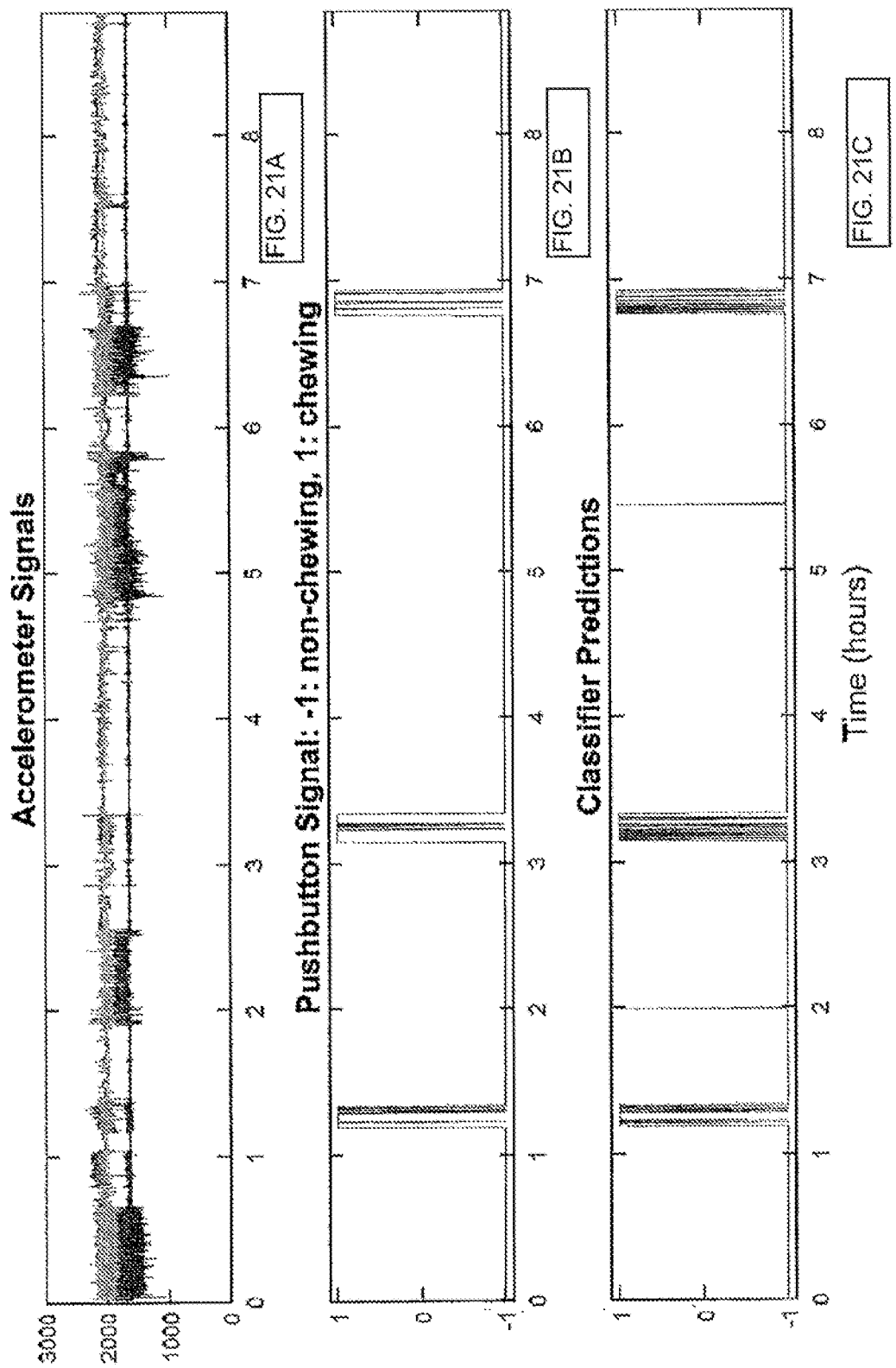
FIGS. 21A-21C are data plots for sensor outputs gathered from a food intake monitoring system according to this disclosure.
Figure 22:
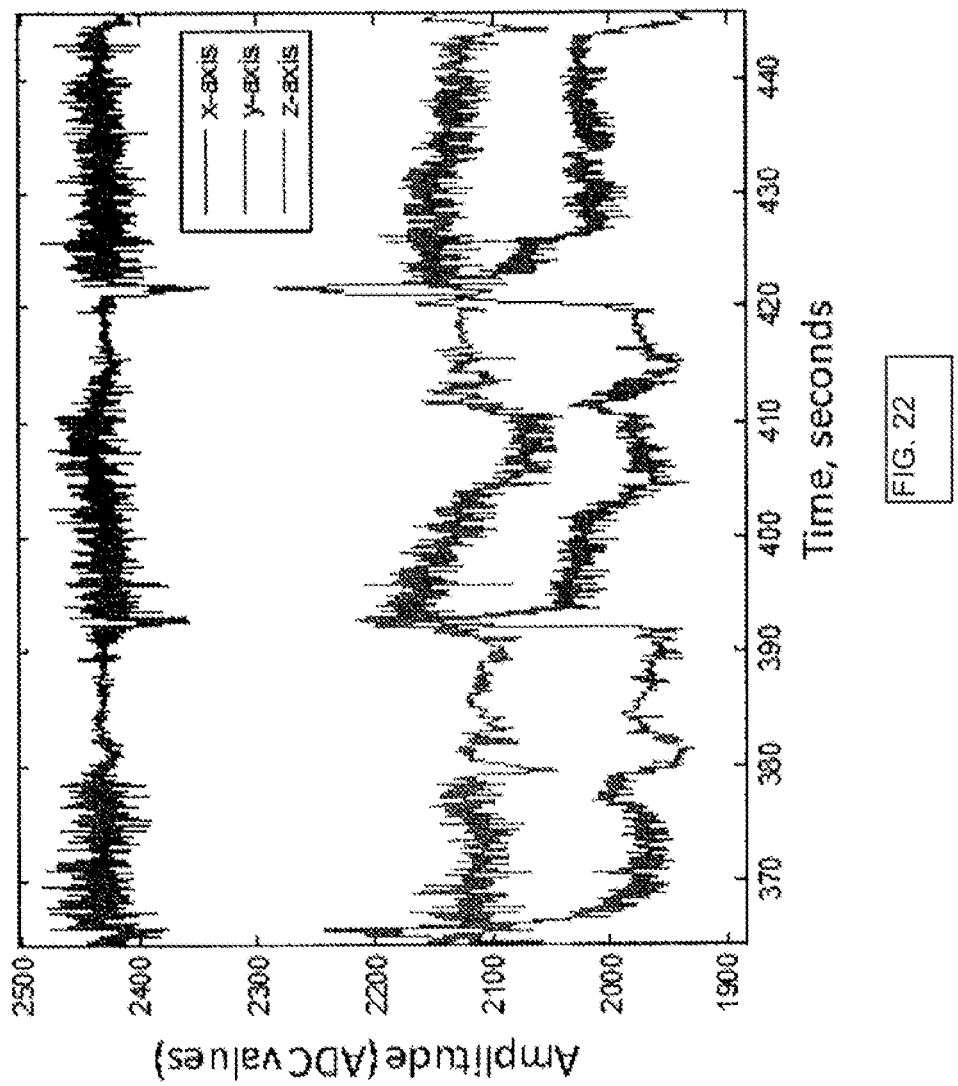
FIG. 22 is a set of plots for data output from an accelerometer incorporated into a food intake monitor as disclosed herein.

For example, as discussed above in some implementations, the sensor is disposed within a clip-on device of FIG. 14, which is coupled to one of the temple portions of the eyeglasses. The clip-on device (1405) may also include a camera (1407), which may be used for taking pictures of food items whenever eating is detected. One or more clip-on devices may be coupled to the eyeglasses (e.g., one clip-on device on each temple portion). In other implementations, the accelerometer (1409) and a camera (1407) may be embedded into the temple portion of the eyeglasses. In some implementations, the electronics of the whole sensor system is fully self-contained within the clip-on or even the temple of the glasses as shown in FIG. 15. FIGS. 17-18 illustrate views of the camera (1702, 1805) that may be included in the system. FIG. 19 is a graphic illustrating positioning of cameras within a food intake monitor and one way of collecting visual information regarding food being ingested by a user. The food, upon being subject to digitized formatting, may be identified by algorithms incorporated into associated computer hardware in communication with the camera. FIG. 20 shows that the temple (2007) connected to a pair of glasses by a hinge (2009) allows for sufficient support and space considerations to provide the above referenced sensors, microcontroller (2018), and camera (2105). These electronic components may include data communication connections among each other and associated transceivers for communicating with other servers over various networks. FIG. 21 illustrates one signal analysis session of a food intake monitor implementation of a clip on device such as that of FIG. 15, in which a pair of eyeglasses has at least one temple (1503) supporting or encasing an accelerometer (1508) for detecting temporalis muscle activity. The accelerometer is disposed on a circuit board within the clip-on device (1505). The circuit board also includes relevant electronics (e.g., a processor, a Bluetooth transceiver, etc.). The graphs of FIG. 21 herein illustrate exemplary signals from the accelerometer correlated with signals from a pushbutton device used to indicate chewing and non-chewing conditions. In other words, the data from the accelerometer (1508) as shown in FIG. 21A is gathered automatically via a wearer's eyeglasses clip-on device (1505) and that data is used by a computerized controller or processor to indicate chewing and non-chewing conditions. During the periods in which the accelerometer (1509) collects data from the eyeglasses, a user wearing the eyeglasses is asked to directly and manually note food intake sessions with a push button device. The push button data of FIG. 21B indicates the user's tracking of chewing and non-chewing conditions. The output of the food intake monitor and associated computers are shown as classifier predictors of FIG. 21C and show a high correlation between the accelerometer data indicated chewing and the user's push button data. This accuracy is due in part to the use of a three axis accelerometer that is programmed to track periodic signals of acceleration on all three axes as shown in FIG. 22.

Additional implementations of the temporalis muscle activity sensor are described and shown in the examples below. In one embodiment, a microcontroller connected to a food intake monitoring system incorporates a high-pass filter with a cutoff frequency of 0.1 Hz. This circuit was used to remove the DC component from the accelerometer output signal, and the signals were normalized to compensate for inter-subject variations. For feature computation, signals were divided into non-overlapping fixed time segments/window called decision epochs. Epoch duration determined the time resolution of the chewing detection.

Figure 23:
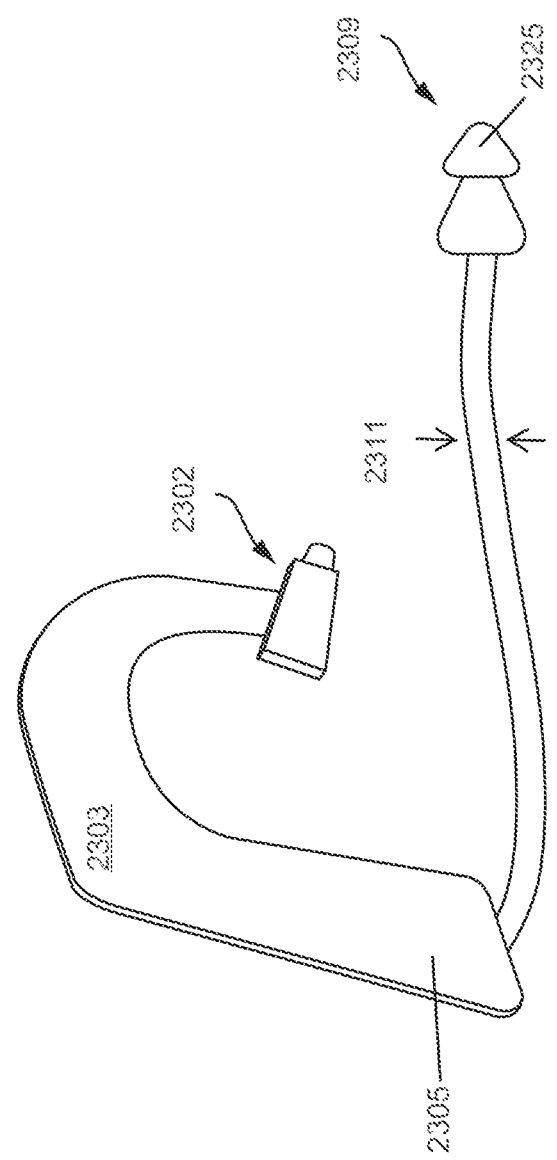
FIG. 23 is a schematic view of a food intake monitoring system for positioning about a wearer's ear as disclosed herein.

Another embodiment of this disclosure is set forth in FIG. 23 and shows an overall system for use with the methods and computer program products described herein to identify food intake and perform computerized statistical analysis as set forth in other embodiments discussed in this disclosure. In this embodiment, the pressure sensor device may incorporate numerous hardware components forming a system for identifying, measuring, recording, and tracking food intake both in terms of items ingested and calories therein. Each device includes an earpiece housing (2305) (e.g., a Bluetooth communication earpiece), an ear bud (2309), an air tube (2311), and an air pressure sensor (2325) disposed within the earpiece housing. The air tube (2311) extends between the ear bud and the air pressure sensor. One or more other electronic and data processing components are also disposed within the earpiece housing (2305). For example, the housing (2305) may also include an accelerometer. The implementation of FIG. 23 shows an earpiece housing with a camera (2302), but similar implementations may utilize an earpiece housing without a camera.

Figure 24:
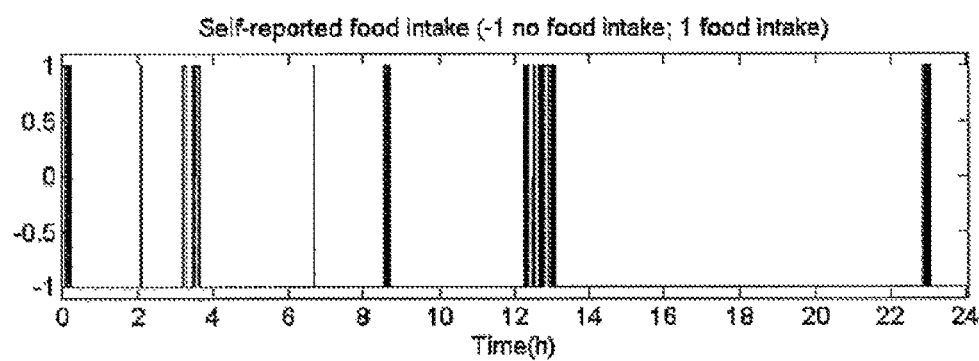
FIG. 24 is a data plot of self-reported food intake via a push button sensor manually operated to collect control data as set forth in this disclosure.
Figure 25:
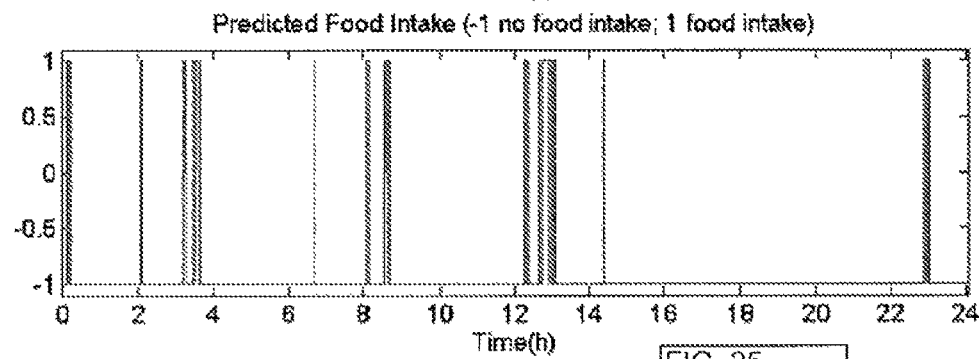
FIG. 25 is a data plot of a food intake monitor's predicted episodes of food intake for comparison with the control data of FIG. 24.
Figure 27C:
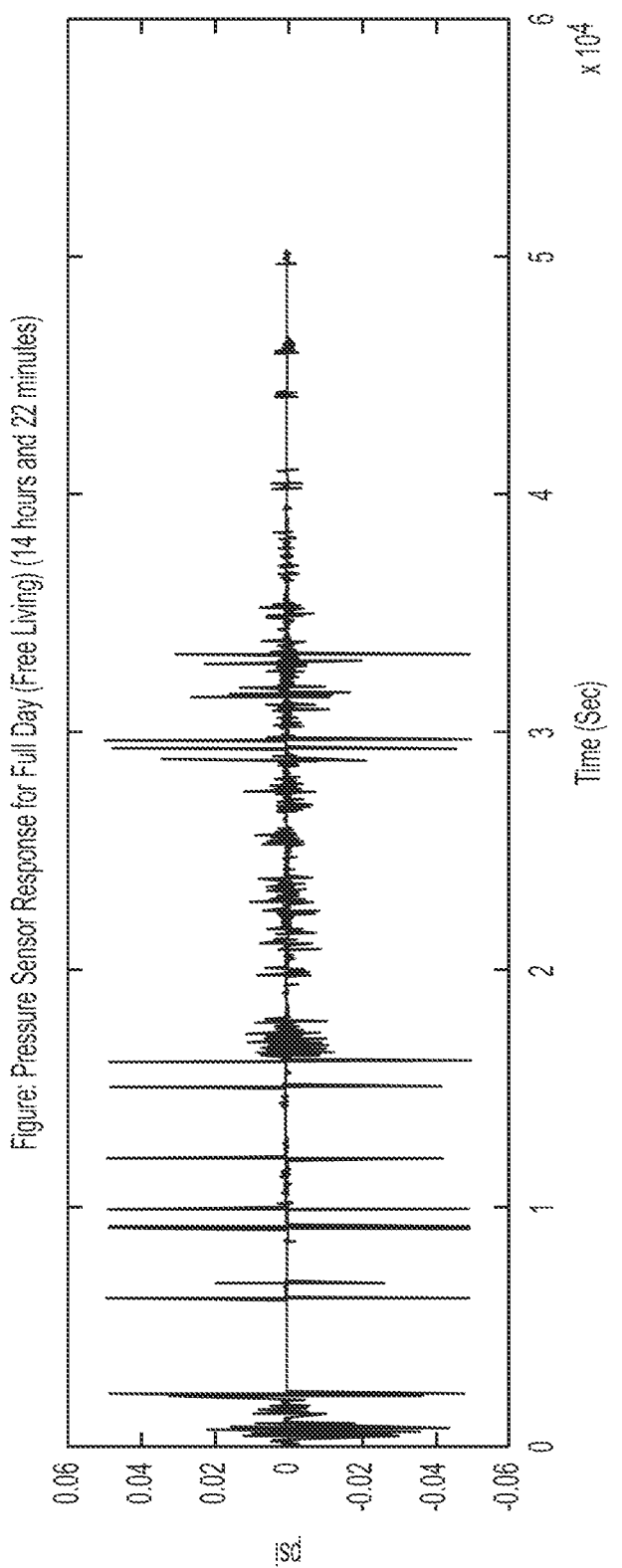

In all, as shown in FIGS. 24 and 25, self-reported food intake (FIG. 24) and predicted food intake (FIG. 25) show approximately 89 percent accuracy of food intake detection with the embodiments of food intake monitors as described herein. The tests related to these results may be described as utilizing food intake monitoring equipment shown in FIGS. 26A-26C. As illustrated in the figures, the food intake monitor of this embodiment utilizes an earpiece housing (2305) designated as a main device that incorporates sensors (2609) (e.g., a Bluetooth communication earpiece), an ear bud (2617), an air tube (2613), and an air pressure sensor disposed within the earpiece housing (2619). The air tube (2613) extends between the ear bud and the air pressure sensor within the housing (2619). One or more other electronic and data processing components are also disposed within the earpiece housing (2619). For example, the housing (2619) may also include an accelerometer. The implementation of FIG. 26 shows an earpiece housing with a camera (2621), but similar implementations may utilize an earpiece housing without a camera. As illustrated in FIG. 26A, the housing (2619) may be smaller if power components such as a battery are incorporated into a companion device (2608) worn by the user via a neck connector (2607). FIG. 26C shows that the ear bud (2617) may be custom molded without any hole for air or sound entry as in the continuously smooth ear bud (2630) or may incorporate the air tube via an associate air hole (2630) as in the pre-formed ear bud (2630). FIGS. 27A, 27B illustrate signal responses of air pressure sensors as shown in FIGS. 26A-26C for different kinds of activities, alongside a user's push-button response to show activities conjoined with eating activity. As illustrated, the devices of FIGS. 26A-26C may be used to distinguish normal daily activities that may occur while eating/chewing is also occurring. The devices used as food intake monitors shown in FIGS. 26A-26C output signals that may be collected and used by a processor to identify whether a person is eating, even if other motion occurs at the same time. The respective sensor responses, user push-button control data (defining periods that the wearer of the sensors identified as definitely eating), and prolonged data over a longer period (14 hours and 22 minutes of wake time) are illustrated in FIGS. 27A-27C.

Figure 29A:
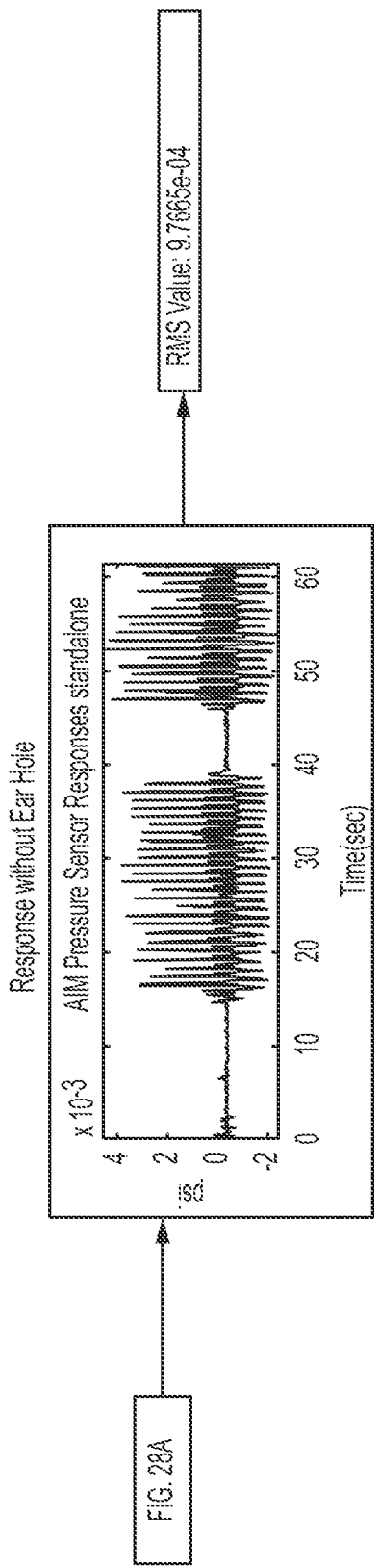
FIGS. 29A-29C are data plots of pressure sensor response data corresponding to respective custom ear bud designs illustrated in FIGS. 28A-28C.
Figure 29B:
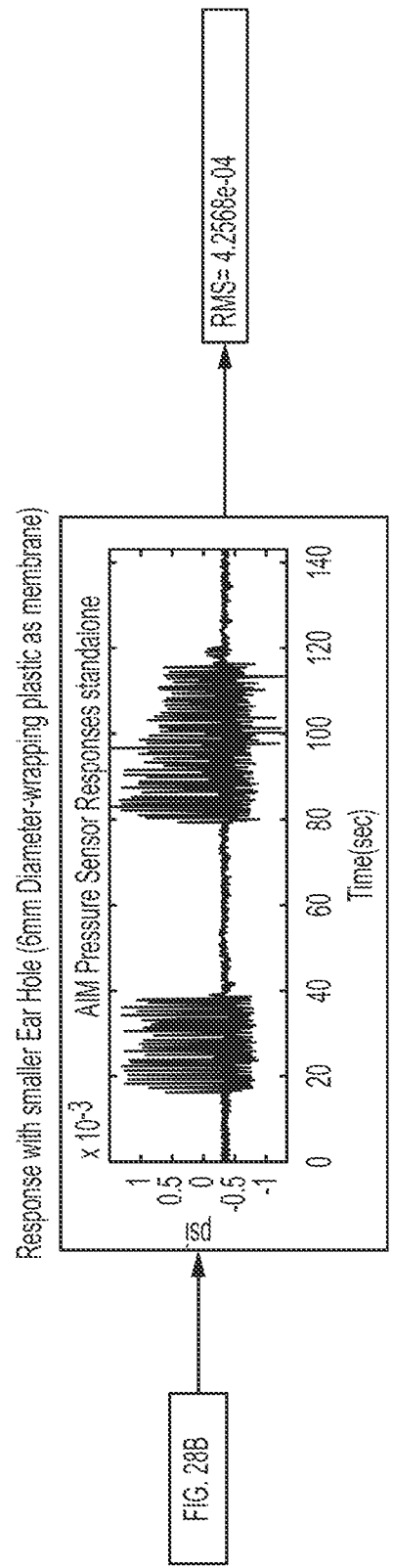
Figure 29C:
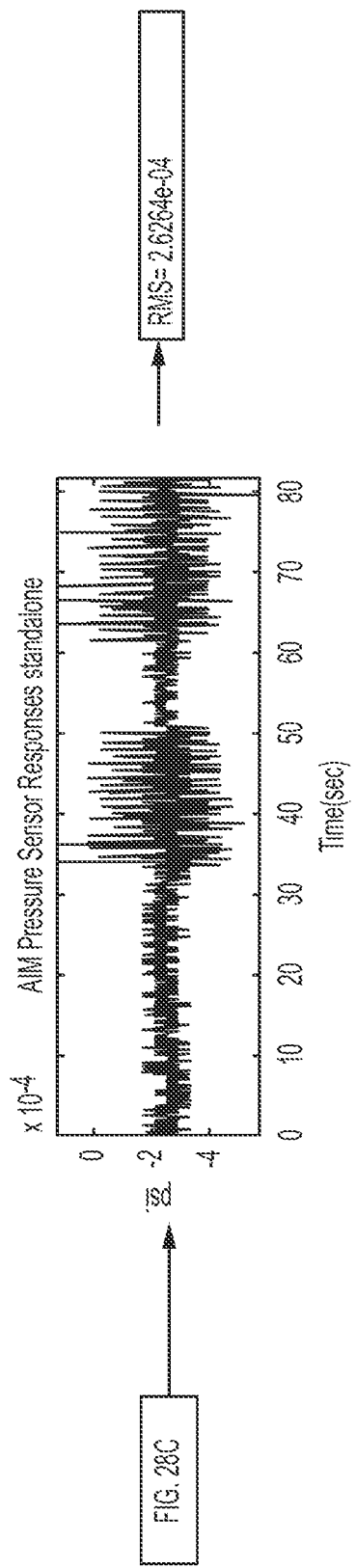

The above described testing scenarios have also been studied in accordance with numerous kinds of custom ear bud designs, wherein the ear buds include at least the pressure sensor described herein. In one embodiment, as shown in FIG. 28A, the ear bud (2630) is a continuously uniform ear bud encompassing at least the above described pressure sensor design. In the ear bud (2630) the only opening within the surface of the ear bud (2630) is that opening (2823A) necessary to accommodate the corresponding air tube (2824) that would fit therein. Otherwise, the embodiment of an ear bud, incorporating a pressure sensor as described herein, having no additional openings for air or sound travel to the ear drum, is within the scope of this disclosure. FIG. 26B shows an ear bud (2830) that defines a side opening (2829) of a first dimension for air and sound travel into the ear canal even when the ear bud incorporates a pressure sensor in the ear bud. FIG. 26C shows that a larger side opening (2831) embodiment of the ear bud (2840) is also within the purview of this disclosure. For example, in one non-limiting sense, FIG. 28B incorporates a side opening (2829) of six millimeters in addition to an air tube opening (2823B) in the ear bud (2830), and FIG. 28C shows a side opening (2831) of twelve millimeters in addition to an air tube opening (2824) in the ear bud (2840). For pressure calibration and pressure sensor accuracy within the ear buds (2830, 2840), the side opening (2829) and larger side opening (2831) may be covered with a plastic membrane that is selected for thickness, porosity, air transmissivity, and sound transmissivity such that a corresponding air pressure sensor within the ear buds (2830, 2840) may be calibrated accordingly (i.e., according to pressure within the custom ear bud with no holes as in FIG. 28A or according to standard atmospheric air pressure for the devices with a side opening shown in FIGS. 28B and 28C. FIGS. 29A-29C show the air pressure sensor response for corresponding food intake monitoring designs utilizing ear bud designs of FIGS. 28A-28C.

As noted above, one distinguishing characteristic, that does not limit the scope of this

| Activities Number | Activities Description | Time |
|---|---|---|
| 1 | Sit silent: sit in a comfortable position | 5 min |
| 2 | Sit while talking: read a document aloud | 5 min |
| 3 | Eat a meal: eat a meal | 20-40 min |
| 4 | Walking while silent: walk on a treadmill at a self-selected comfortable speed | 5 min |
| 5 | Walking while talking: walk on a treadmill at a self-selected comfortable speed and talk with the research assistant | 5 min |

-continued

| Activities Number | Activities Description | Time |
|---|---|---|
| 6 | Walking while eating: eat a chocolate bar while walking on the treadmill | 10 min |
| 7 | Sit silent: sit in a comfortable position | 5 min |
| 8 | Activities of daily living: shelving/stacking items | 5 min | disclosure, lies in the food intake monitors of FIGS. 26A-C and 28A-C having accuracy in light of ambient conditions that may vary for a user. FIG. 30 is another view of data resulting from laboratory testing of the food intake monitors utilizing the pressure sensors (FIGS. 26 and 28) to detect chewing and ingestion during other activities as noted, as confirmed by a test subject clicking a push button tool during periods of chewing as shown (i.e., the spikes of data in FIG. 30B result in a user confirming food intake by manually activating a push button). FIG. 30 further identifies the pressure sensor output of the food intake monitors of FIGS. 26A-26C as being useful for monitoring food intake in the presence of conditions that may be considered "noisy" such as walking, talking, etc. Tables of data showing test results of the food intake monitors of FIGS. 26A-26C and the custom ear buds of FIGS. 28A-28C are consolidated from FIGS. 30A and 30B as follows:

Table 1:

The test equipment shown in FIGS. 26A-26C and 28A-28C was also subject to power and performance confirmation in terms of how many frames of data the camera could gather for processing along with pressure sensor data and achieve the results below for the above noted conditions:

TABLE 2

| Number of Frames | With 150 mAh Battery | Expected (1000 mAh) |
|---|---|---|
| 10 | 5 hr and 12 min | 33 hours (approximately) |
| 15 | 3 hr and 4 min | 20 hours (approximately) |

TABLE 3

| Number of Frames | With 1000 mAh Battery Connected Battery | Longevity |
|---|---|---|
| 15 | 1000 mAh | 24.2 hours |

Figure 31A:
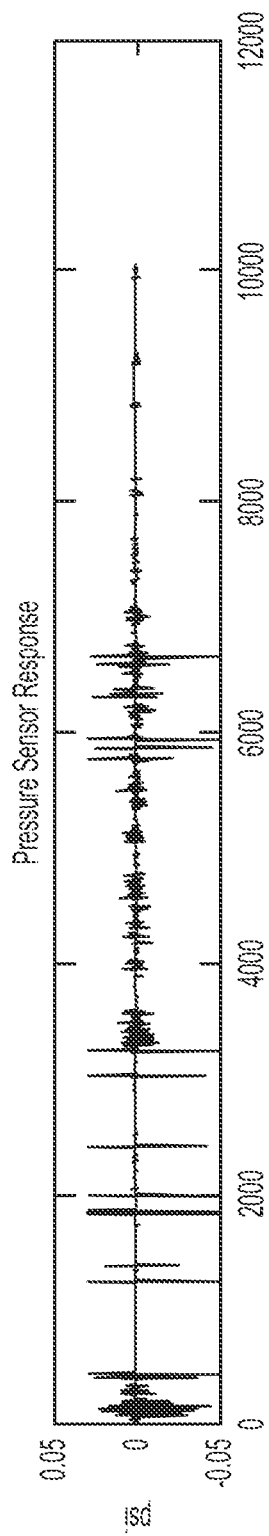
FIGS. 31A-31I are data plots of pressure sensor outputs, push button control outputs, and predicted chewing episodes from food intake monitors configured according to this disclosure.
Figure 31B:
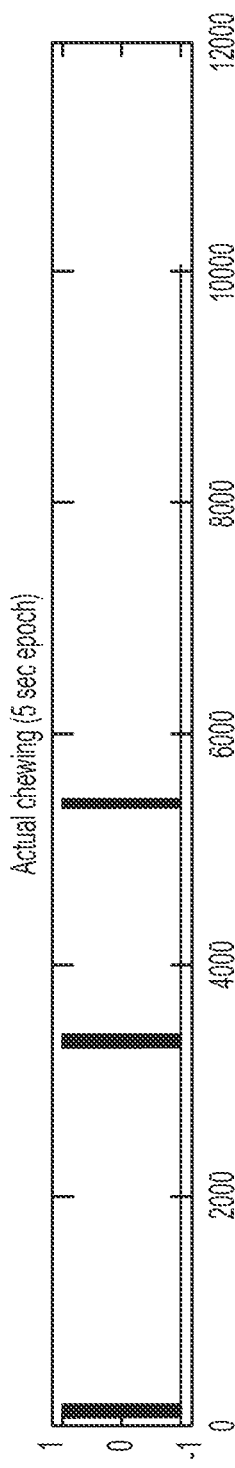
Figure 31C:
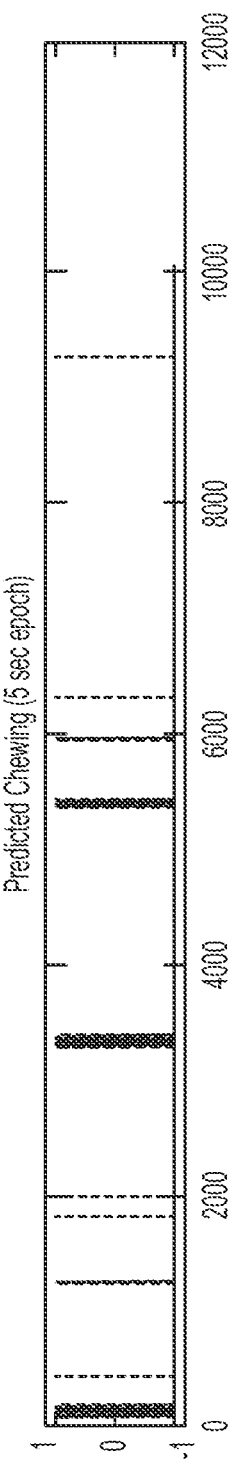
Figure 31D:
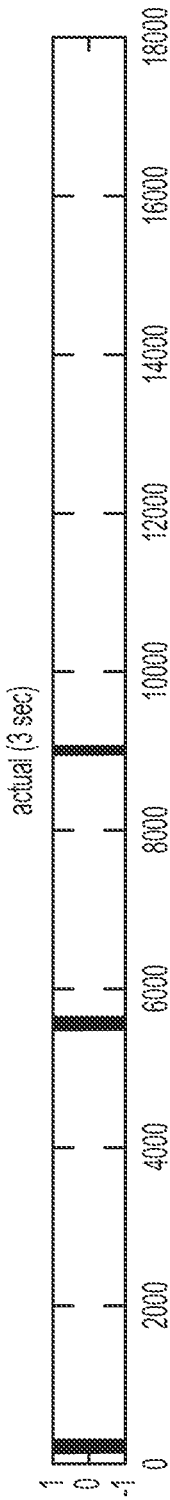
Figure 31E:
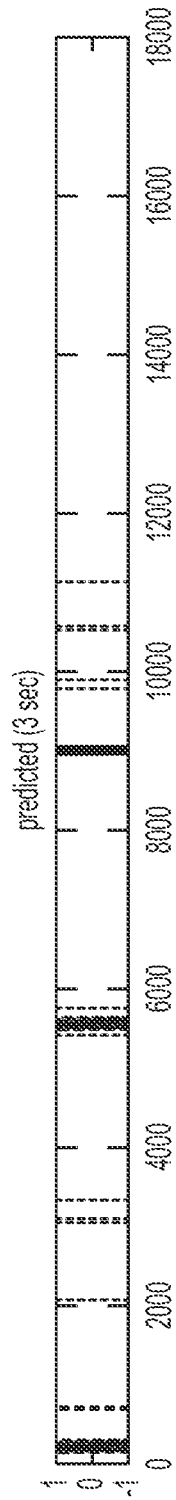
Figure 31F:
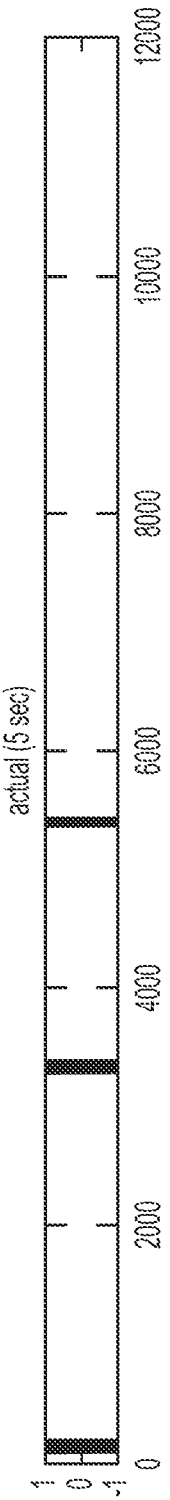
Figure 31G:
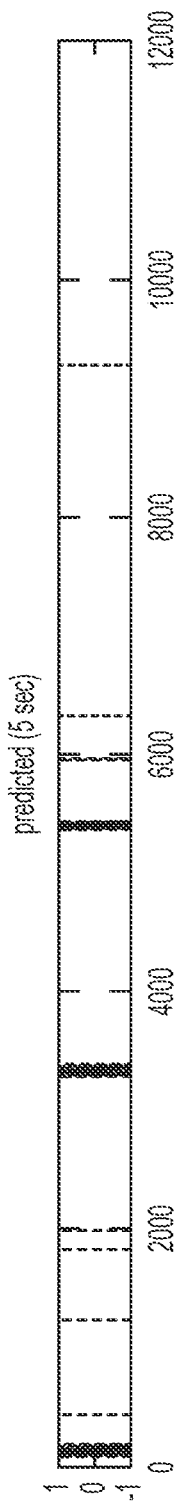
Figure 31H:
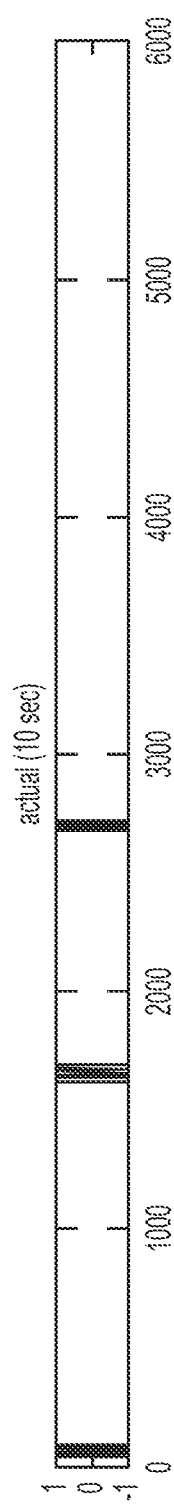
Figure 31I:
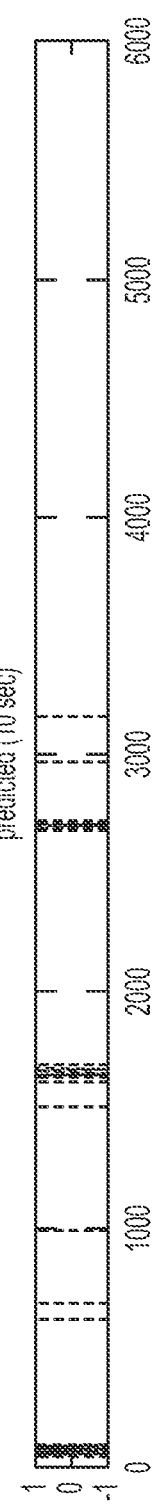

In accordance with the above noted tables of data and the equipment of FIGS. 26 and 28 herein, one test of this disclosure incorporated five different subjects using the food intake monitors of FIGS. 26 and 28B and tested with the push button control devices for the results shown in Tables 4-9 herein. For Tables 4-9 below and FIGS. 31A-31F herein, a 6 mm diameter customized ear bud with plastic membrane was selected for use. The pressure sensor response of FIG. 31A was the result of the pairs of plotted signal data from the air pressure sensor of the associated ear buds and each user's manual push button control data (31B, 31C) ; (31D, 31E) ; (31F, 31G) ; (31H, 31I). Each of the Tables 4-9 show the results of the predicted food intake data from a pressure sensor embodiment of FIG. 28B identifying chewing (FIGS. 31C, 31E, 31G, and 31I) with actual data gathered from the user's push button control showing definite episodes of chewing (31B, 31D, 31F, and 31H). The tabulated results are shown below. It is to be noted that the data has been subject to a support vector machine according to identified epochs for data comparison. The system embodied in FIGS. 26 and 28 includes the above described physical components for monitoring food intake into a body and may be connected, via a data network or by hard wire connection, to a central processing unit connected to computer memory, a data buffer, and an image buffer. The disclosure above is reinforced by reminding that certain other embodiments of this disclosure may include a jaw sensor configured to detect jaw motion and transmit a plurality of cycles of jaw sensor data to the data buffer for storage in the time domain, wherein the central processing unit accesses the data buffer to determine periodic patterns in the jaw sensor data and classifies at least one epoch of time as a period of at least one of the cycles of jaw sensor data. An inertial measurement unit, such as the above noted accelerometer, may be configured to detect body motion and to transmit body motion data to the memory for storage in accordance with the time synchronization of corresponding finite epochs of time equal to the period and start/stop times of the cycle of the jaw sensor data. Of course, a camera may be configured to take images of food and to transmit the images to the image buffer for storage in the time domain. The central processing unit is configured to execute computer implemented instructions configured to save a record of food intake in the memory by:

(i) determining a respective frequency of deglutition data for the finite epochs of time;

(ii) comparing the respective frequencies of deglutition with respective durations of the corresponding finite epochs of time and selecting a frequency resolution and a temporal resolution of a food intake monitoring analysis;

(iii) using the frequency resolution to compare each respective frequency of deglutition with a baseline spontaneous swallowing frequency associated with the body, such as the user's push button data described above; and (iv) using the temporal resolution to select a lag factor that determines a number of neighboring finite epochs of time to be added to at least one finite epoch of time to determine a total epoch of time in which the patterns of the jaw motion are associated with food intake;

(v) using the frequency of deglutition comparison with the baseline and the patterns of the jaw sensor data during the total epoch of time to confirm food intake.

TABLE 4

Classifier performance for different epoch
(20 Features from pressure sensor signal)

| Epoch | Precision | Sensitivity | Specificity | Accuracy | Fscore |
|---|---|---|---|---|---|
| 1 Sec | 0.93323 | 0.82707 | 0.98747 | 0.88015 | 0.87603 |
| 2 Sec | 0.90197 | 0.8562 | 0.98106 | 0.87909 | 0.87848 |
| 3 Sec | 0.93023 | 0.87045 | 0.9869 | 0.90034 | 0.89924 |
| 5 Sec | 0.9268 | 0.8563 | 0.9849 | 0.8916 | 0.89 |
| 10 Sec | 0.92582 | 0.78627 | 0.9857 | 0.85605 | 0.84828 |
| 15 Sec | 1 | 0.76036 | 1 | 0.88018 | 0.85948 |
| 20 Sec | 0.88 | 0.85287 | 0.96703 | 0.86644 | 0.8614 |

TABLE 5

Classifier performance for different epoch
(20 Features from pressure sensor signal)

| Epoch | Precision | Sensitivity | Specificity | Accuracy | Fscore |
|---|---|---|---|---|---|
| 1 sec | 0.79813 | 0.86923 | 0.96621 | 0.83368 | 0.82295 |
| 2 sec | 0.85841 | 0.90029 | 0.97723 | 0.87935 | 0.8717 |
| 3 Sec | 0.88596 | 0.90452 | 0.98193 | 0.89524 | 0.88911 |

TABLE 5-continued

Classifier performance for different epoch
(20 Features from pressure sensor signal)

| Epoch | Precision | Sensitivity | Specificity | Accuracy | Fscore |
|---|---|---|---|---|---|
| 5 Sec | 0.88078 | 0.90812 | 0.98214 | 0.89445 | 0.88757 |
| 10 Sec | 0.81701 | 0.86585 | 0.97351 | 0.84143 | 0.82026 |
| 15 sec | 0.87969 | 0.93147 | 0.98478 | 0.90558 | 0.89376 |
| 20 Sec | 0.79718 | 0.93123 | 0.9751 | 0.86421 | 0.82734 |
| 30 sec | 0.90909 | 0.90347 | 0.98529 | 0.90628 | 0.88289 |

TABLE 6

Classifier performance for different epoch using pressure signal
and accelerometer signal (10 Features out of 80 features selected
by mRMR feature selection)

| Epoch | Precision | Specificity | Sensitivity | Accuracy | Fscore |
|---|---|---|---|---|---|
| 1 sec | 0.76007 | 0.87358 | 0.95953 | 0.81682 | 0.80678 |
| 2 sec | 0.72599 | 0.86365 | 0.95484 | 0.79482 | 0.77462 |
| 3 Sec | 0.8089 | 0.89041 | 0.96737 | 0.84965 | 0.8444 |
| 5 Sec | .8876 | 0.89872 | 0.98091 | 0.89316 | 0.89129 |
| 10 Sec | 0.86808 | 0.87788 | 0.97946 | 0.87298 | 0.8643 |
| 15 sec | 0.94711 | 0.93659 | 0.99104 | 0.94185 | 0.93694 |
| 20 Sec | 0.87774 | 0.93384 | 0.98378 | 0.90579 | 0.8924 |
| 30 sec | 0.87001 | 0.83314 | 0.97657 | 0.85158 | 0.8126 |

TABLE 7

Chew count algorithm is built based on segmentation and
linear regression. 5 subjects with chew counts;

$$error = \frac{Actual_{count} - Predicted_{count}}{Actual_{count}} \times 100\%$$

| Subjects | Actual Count | Predicted Count | Error (%) |
|---|---|---|---|
| 1 | 328 | 346 | −5.48% |
| 2 | 353 | 379 | −7.36% |
| 3 | 433 | 485 | −12.01% |
| 4 | 383 | 411 | −7.31% |
| 5 | 519 | 577 | −11.17% |

TABLE 8

| Epoch | Precision | Sensitivity | Specificity | Accuracy | Fscore |
|---|---|---|---|---|---|
| 3 Sec | 0.84914 | 0.78175 | 0.99788 | 0.81544 | 0.81405 |
| 5 Sec | 0.90411 | 0.825 | 0.99859 | 0.86455 | 0.86275 |
| 10 Sec | 0.8125 | 0.78 | 0.99635 | 0.79625 | 0.79592 |

TABLE 9

| Subject | Actual Count | Predicted Count | Error (%) |
|---|---|---|---|
| 1 | 1327 | 1578 | −18.91 |

Other related embodiments of this disclosure may include a hand gesture sensor 212 and may detect proximity to the mouth by using an RF strength measurement between a transmitter located on one of the user's arms and a receiver located in the headset or frames of the glasses; or detect the motion of bringing one's hand to the mouth through the means of inertial measurement unit that is placed on an arm, such as a wrist unit or a unit integrated into clothing. The hand gesture sensor may also detect hand proximity through passive capacitive coupling with the hand, or coupling from AC potentials injected at the device location. Several of the hand gesture detection methods can be combined to increase reliability of detection or to minimize number of wearable pieces.

Various types of microphones may be used as swallowing sensors 204. For example, a piezoelectric bone-conduction microphone may be used with high dynamic range and low power consumption. The sensor may be modified to be placed on the mastoid bone behind the ear or used as an ear probe. As another example, a piezoelectric noise-canceling microphone may be used, which has relatively small dimensions, a high dynamic range, and low power consumption. A third exemplary model may be a modified throat microphone usually used for hands-free radio communications. The throat microphone may be designed to pick up vibration signals from the surface of the skin, rather than waves of sound pressure.

As such it may be highly insensitive to external noise, but sensitive to low-level sounds providing a dynamic range of, for example, 58 db and low power consumption of, for example, 0.5 ma at 3V. The microphone may be worn on an elastic band around the neck.

An exemplary jaw sensor may include a film piezoelectric sensor encased in a thin strip of elastic polymer material that regains shape after being deformed. The sensor may detect mastication (chewing) by identifying specific motion of the lower jaw. Essentially, it detects changes in skin curvature created by motion of the posterior border of the mandible's ramus. The surface of the sensor may be, in one implementation, polished or treated with a low friction material to avoid abrasion. The sensor may be attached to the skin by an adhesive or held in contact with the skin by applying mechanical force from the wearable device. Exemplary implementations include a behind-the-ear module or both behind-the-ear and laryngeal modules being worn by a subject.

Data from the sensors may continuously transmit to the pocket or wrist storage unit that accumulates data in memory, such as on a Secure Digital (SD) card. The storage unit may be a separate component or included in a personal computer, cell phone, smart phone, watch, or the like.

The combination of the signals from one or more of these sensors is used by a microcontroller to detect food intake. The food intake may be characterized by the number of chews and chewing frequency. A speaker built into the earbud, harness, or enclosure may be used to deliver situation specific feedback, such as "chew more slowly" or other responses. Alternatively, a radio frequency (RF) link to an external computing device, such as a Smartphone, may be used to deliver the feedback. The RF link may also be used to aggregate historic eating data on the external computing device and/or on a cloud-based computing device, perform the calculation of energy and nutrient content, and deliver the eating data and/or calculated data in a visual and textual form to the user.

In some implementations, a hand gesture sensor 212 may be added to identify the hand-to-mouth motion associated with eating. The timing and duration of food intake instances may be measured and monitored along with the number of bites, chews and swallows. A wireless module may include one or more of an accelerometer to capture body acceleration and may be integrated into, for example, a watch. A push button may also optionally be included to self-report food intake by the user to initially calibrate the system to a particular individual.

Examples of signal processing by central processing unit 208 consistent with one or more implementations will now be described. The signal processing may be done locally by a processor integrated into the wearable device, a processor on a handheld device (e.g., a cell phone), a remote server or a combination of these configured in such manner as to extend the battery life of the wearable device. Initial signal processing of swallowing sensor data may include preamplification and low pass or band pass filtering with cutoff frequency of, for example, 3500 Hz. Preamplification cascade may allow for impedance matching and amplification of weak signals from the sensor before subjecting them to any further processing. The peak frequency detected by the swallowing sensor varies individually with subject and food type. In one example, the low pass filtering with a cutoff at 3500 Hz may be used to pass the spectrum of a swallow sound, while rejecting excessive high frequency noise and preventing aliasing during analog-to-digital conversion.

The dynamic range of signal from the swallowing sensor may be in the range of, for example, 40-60 dB, which may be insufficient to reliably capture the signals originating from swallowing without saturating the amplification circuits during normal speech. Therefore, the signal from the sensor may be pre-amplified by an Automatic Gain Control (AGC) amplifier.

The signal from the output of the variable gain amplifier may be sampled by, for example, a Successive-Approximation-Register (SAR) analog-to-digital converted at the sampling frequency of 10000 Hz, which provides accurate sampling of high frequency components in the filtered sensor signal and avoids aliasing. The preamplification coefficient can be scaled up to 40 dB by a variable-gain amplifier, giving average resolution of about 18-19 effective bits. Additional signal processing may be employed to enhance resolution. The sampled signal may be compressed using lossless and fast adaptive Huffman coding and transmitted to the pocket/wrist module, a cell phone, storage 210, or any other device. Gain values for automatic gain control may be stored along with the sampled analog signal to serve as a predictor. In addition or alternatively, the sample signals may be communicated wirelessly, such as through a WiFi or Bluetooth connection, to a nearby electronic device.

Central processing unit 208 may take the signal from the jaw motion sensor and low pass filter it with a cut-off frequency, such as 30 Hz-300 Hz. The signal may be sampled by an analog-to-digital converter at the sampling rate of, for example, 1000 Hz. The sensor data may also be transmitted to the portable device (e.g. smartphone) or remote server and used in pattern recognition of mastication, or processed directly on the wearable device.

Figure 2B:
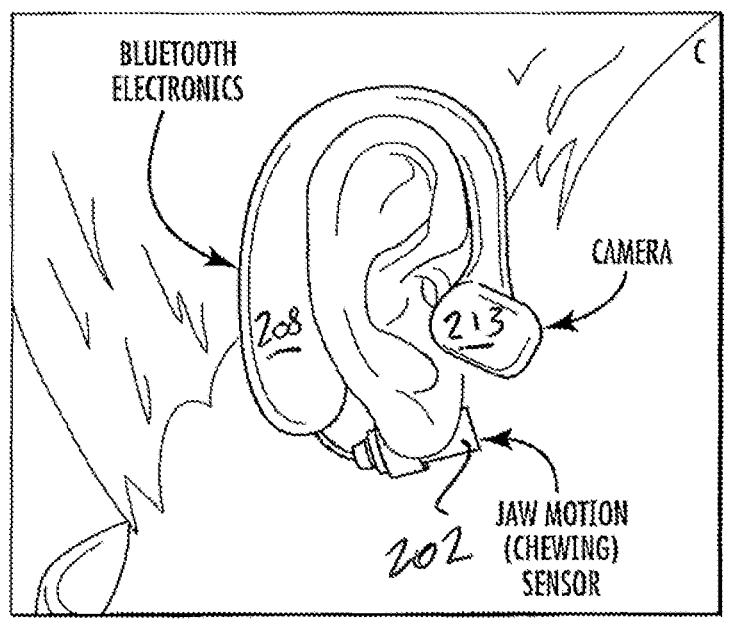
FIG. 2B illustrates exemplary components for monitoring ingestive behavior according to the implementation shown in FIG. 1A.

FIG. 2B illustrates another implementation with a camera may be integrated into the system to take images of food. The camera may be used in addition to, or instead of, any of the sensors discussed with reference to FIG. 2A previously. Adding a camera may allow more precise calculation of the type of food being consumed and reduce or eliminate false positives in food intake detection by allowing for visual validation of each intake episode. The direction of the camera's optical axis should follow the natural line of gaze, as it is typical to look at the foods being eaten during the picking up or biting the foods. The camera can be integrated into the over-the-ear or behind the ear headset, or inside of a glasses frame.

To save battery power the camera is kept in powered down mode and only is turned on for brief moments of time to take pictures every 1-100 s. Internal temporary image buffer keeps the history of several previous images to accommodate for the fact that the image has to be taken prior to detected jaw motion due to food intake. Once food intake is detected, the appropriate image is taken out of temporary memory buffer and saved or transmitted for processing. Image capture can also be triggered by hand gestures. The relative timing of the food intake detection events and frequency and timing of the image capture can be probabilistically optimized to maximize the likelihood of capturing the foods while minimizing camera's power consumption. The goal is to minimize frequency with which images are taken and keep the camera in low-power (sleep) state while maximizing probability of capturing a clear image of the food being eaten.

The camera may utilize the inertial measurement unit 206 to take clear pictures. The inertial measurement unit may be used to identify moments of least head motion and capture still images without motion blur. The images may be retaken if the inertial sensor readings suggest possibility of a blurred image. The inertial measurement unit may also be used to estimate field of vision during a meal and capture images covering the full scene. The head motion during a typical meal or snack has a limited and well-defined range of motion covering the full scene containing the foods. Use of inertial measurements will allow reconstruction of the relative location of the camera's optical axis and capture of images covering the whole field of view and recovering the scene at the analysis stage.

Additional image processing from the camera may include image filtering, scene reconstruction from partially occluded images and depth estimation from camera motion. The captured images may contain images of low quality, or images of the items not related to the foods being eaten. Since a redundant number of images is captured, such images may be discarded by filtering algorithms. Images captured by the wearable camera may also be partially occluded and contain various views of the scene. Automatic computer algorithms may use the still image sequence and inertial sensor readings to reconstruct the full scene and recover distances to the objects and object sizes.

Using imagery allows, automatically, without any participation from the wearer, images to be captured, stored, and wirelessly transmitted when the food intake is detected, thus capturing composition and energy density of the food. A nutritionist or an automatic computer algorithm may use these images to obtain energy density and portion size estimates. The energy density and portion size estimates with or without swallowing, chewing and hand gesture based estimates of ingested mass can then be used to estimate the energy consumed at each snack and meal.

The images may be used to identify foods and determine portion size based on container, plate, and cup sizes. The information may be automatically entered into tracking software and use a reference database containing the total energy, macro- and micro-nutrient content of all USDA food items. The outcome of image analysis will be numeric estimates of mass ($M_{IMG}$), energy content ($EC_{IMG}$) and energy density ($ED_{IMG}$) for each food item. Total energy intake may be computed as $EI=\Sigma_{i=1}^{N} ED_{IMG}^{i}(M_{IMG}^{i}+M_{HG+CH}^{i})/2$, where N is the number of food items.

Figure 3:
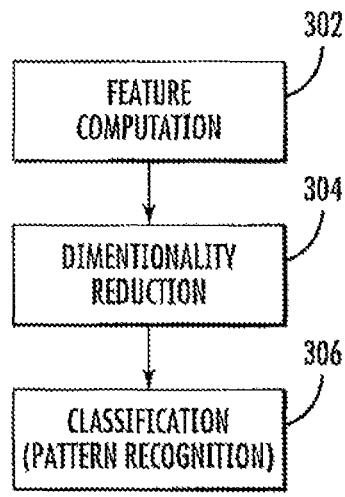
FIG. 3 illustrates an exemplary flowchart for signal processing.

FIG. 3 illustrates an exemplary flowchart for signal processing of swallowing sensor signal after initial signal processing. One example of pattern recognition for deglutition may utilize a time-frequency decomposition method, such as Short-Time Fourier Transform (STFT) for feature extraction, Principal Component Analysis (PCA) for reduction of dimensionality and Multi-Layer Perceptron (MLP) artificial neural network for classification. In this example, the signal may be split into short intervals (epochs) with the size in the range of, for example, 50 to 30000 ms. Duration of an epoch may determine the balance between frequency and temporal resolution of the swallowing signal analysis.

At step 302, feature computation including the short-time Fourier Transform may be calculated for each epoch:

$$X_m(k) = \sum_{n=0}^{N-1} w(n)x(n+mN)e^{-jw_k n},$$

where $X_m(k)$ is the SFTF for the epoch m; N is the size of an epoch in samples; $w(n)=0.5+0.5\cos(2\pi n/N)$ is the Hanning windowing function to reduce spectral leakage. Next, k Power Spectral Density coefficients are calculated for each epoch. Together with the optional AGC gain value, they may form the initial predictor vector v. The number of elements in v may also be reduced by a dimensionality reduction method (step 304) such as PCA, forming a reduced predictor v'.

The pattern recognition (classification) step 306 may use a MLP neural network with vectors $v'_i$, (i=1,m) as inputs. The MLP accepts the input vector, propagates the vector through its artificial neurons and produces a label of '0' or '1' on its output. The label indicates whether the epoch in question contains a swallow or not. The classification label is then passed for further processing that is used to detect and characterize food intake from chewing and/or swallowing and hand gesture sequences. The MLP network may be implemented using floating point or fixed point precision arithmetic, with the use of former targeting power savings on processors without hardware acceleration for floating point operations. The MLP network has to be trained prior to its use. Training of the network can be performed on the "gold standard" data collected from a population of individuals (performed once during the design stage) and further adapted to individual patterns using self-report data.

The training of the MLP may follow the Levenberg-Marquadt or other algorithms. Training may be performed once on a dataset collected from a population, thus resulting in a neural network classifier that does not need individual calibration before use. The MLP network may also be trained from data collected on a given individual, thus resulting in individually-calibrated recognition model.

A second exemplary pattern recognition technique for deglutition may use a discretized version of Continuous Wavelet Transform (CWT) for feature extraction, PCA for reduction of dimensionality, and Dynamic Time Warping (DTW) with nearest neighbor classification. To extract features, a discretized version of CWT algorithm may be used on epochs.

$$CWT_x^\psi(\tau, s) = \Psi_x^\psi(\tau, s) = \frac{1}{\sqrt{|s|}} \sum_{t=1}^{N} x(t)\psi^*\left(\frac{t-\tau}{s}\right),$$

where $\tau$ represents translation, s represents scale, and $\psi^*(t)$ is the mother wavelet. A Morlet mother wavelet may be used, which is defined as $$\psi^*(t) = e^{jat}e^{-t^2/2s},$$

where a is a modulation parameter. Wavelet coefficients and optional AGC gain form the initial vector predictor vectors $v_m$. Principal component analysis may be applied in the same manner as for the SFTF/MLP method and reduced-dimensionality feature vectors $v'_m$ are formed.

Classification of the swallowing sounds may follow the Dynamic Time Warping technique. In one example, the classification scheme is built around N (10-1000) clear recordings of the swallowing sound that serves as the perfect class instances. A fuzzy expert system may use gain, amplitude and duration of signals to roughly identify potential swallows on the recordings. The DTW procedure may be applied to the test regions on the recording to compare them to the reference sounds and establish the measure $D(X, R_i)=\min \forall \phi \Sigma_{k=1}^T d(\phi_x(k), \phi_{R_i}(k))f(k)/m_\phi$, where X is the test sound, $R_i$ is the $i^{th}$ reference sound, $\phi$ is a warping path, T is the path length, d is the distance measure between features of X and $R_i$, f is the slope weight, $M_\phi$ is the global path weight.

The result of DTW procedure is N metrics $D(X,R_i)$, establishing how close the test sound is to the reference sounds. These metrics classify the test sound as a swallow sound if $\min \forall i\ D(X,R_i)<e$, where e is the experimentally determined detection threshold.

Pattern recognition of swallowing may also employ machine learning techniques tailored to minimization of power consumption in the wearable device such as decision trees, random forests, logistic discrimination, Bayesian networks and other techniques that present relative light computational load to the processor. The pattern recognition may be split between the processor of the wearable device, performing first level detection with potentially high level of false positives at a low computational (and energy cost) and storing/wirelessly transmitting such epochs for more computationally intensive, but more accurate processing on the smart phone or in the cloud.

A set of useful characteristic such as number of swallows, swallowing frequency, variation of the swallowing sequence in time may be useful to analyze ingestive behavior of a person (potentially in combination with chewing metrics and hand gesture metrics): detect periods of food intake, identify solid and liquid intake, detect number of unique foods in a meal, and estimate mass and caloric intake.

The pattern recognition technique for detection of mastication may operate on the time series data acquired by the jaw motion sensor and be based on the fact that masticatory movements are characteristically periodical.

Figure 4:
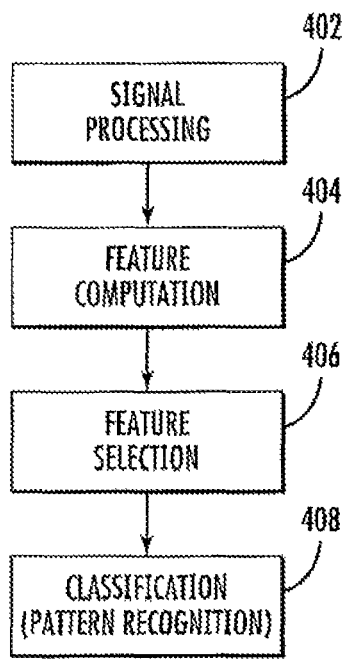
FIG. 4 illustrates a second exemplary flowchart for signal processing.

FIG. 4 illustrates another exemplary implementation for detection of mastication. At step 402, the signal from the jaw motion sensor may be band-pass filtered to remove high-frequency noise and low-frequency drift of the zero axis. At step 404, a feature vector $f_i \in \mathfrak{R}^d$ representing each epoch (for i=1,2, . . . , N; where N is the total number of epochs) may be created by combining a set of 25 scalar features extracted from the filtered and unfiltered signal of each epoch in linear and logarithmic scale. This set of 25 features may include time domain and frequency domain features shown in Table I.

TABLE 10

SCALAR FEATURES USED TO EXTRACT
INFORMATION FROM CHEWING SIGNAL

| Feat # | Description # |
|--------|---------------|
| 1 | RMS |
| 2 | Entropy (signal randomness) |
| 3 | Base 2 logarithm |

TABLE 10-continued

SCALAR FEATURES USED TO EXTRACT
INFORMATION FROM CHEWING SIGNAL

| Feat # | Description # |
|---|---|
| 4 | Mean |
| 5 | Max |
| 6 | Median |
| 7 | Max to RMS ratio |
| 8 | RMS to Mean ratio |
| 9 | Number of zero crossings |
| 10 | Mean time between crossings |
| 11 | Max. time between crossings |
| 12 | Median time between cross. |
| 13 | Minimal time between cross. |
| 14 | Std. dev. of time between crossings |
| 15 | Entropy of zero crossings |
| 16 | Number of peaks |
| 17 | Entropy of peaks |
| 18 | Mean time between peaks |
| 19 | Std. dev. of time between peaks |
| 20 | Ratio peaks/zero crossings number |
| 21 | Ratio zero crossings/peaks number |
| 22 | Entropy of spectrum |
| 23 | Std. dev. of spectrum |
| 24 | Peak frequency |
| 25 | Fractal dimension (uniqueness of the elements inside an epoch) |

An initial feature vector $f_i$ may be created merging several feature subsets that were formed by calculating the 25 scalar features form the filtered and unfiltered epoch and by different feature combinations:

$$f_i = \{f_{filt}, f_{unfilt}, f_{filt/unfilt}, f_{unfilt/filt}, f_{filt \cdot unfilt}\} \quad (3)$$

where $f_{filt}$ and $f_{unfilt}$ it represent feature subsets extracted from the filtered and unfiltered epochs respectively; $f_{filt/unfilt}$ and $f_{unfilt/filt}$ represent two feature subsets obtained by calculating the ratio between each feature of the $f_{filt}$ and $f_{unfilt}$ subsets and vice versa; and $f_{filt \cdot unfilt}$ represents another subset of features obtained by calculating the product between each feature of the $f_{filt}$ and $f_{unfilt}$ subsets. These combinations yield an initial feature vector with 125 dimensions.

A scale equalization may be performed to features in the $f_{filt}$ and $f_{unfilt}$ it subsets using the natural logarithm. Ratio and product between resulting feature subsets may be calculated to create a log-scaled feature vector with 125 dimensions:

$$f_{log\ i} = \{f_{log\ filt}, f_{log\ unfilt}, f_{log\ filt/log\ unfilt}, f_{log\ unfilt/log\ filt}, f_{log\ filt \cdot log\ unfilt}\} \quad (4)$$

Finally, both the linear and log-scaled feature vectors may be concatenated into a single 250-dimension feature vector $F_i \in \mathfrak{R}^{250}$ representing each epoch $$F_i = \{f_i, f_{log\ i}\} \quad (5)$$

To account for the time-varying structure of the chewing process, features from neighboring epochs may be added to the original epoch feature vector according to the number of lags selected L. Different lag values may be applied: 0-10. If the number of lags is greater than zero, then features from L previous and L subsequent epochs are included in the final feature vector $\tau_i$:

$$\tau_i = \{F_{i-L}, \ldots, F_{i-1}, F_i, F_{i+1}, \ldots, F_{i+L}\} \quad (6)$$

At step 406, most important features may be selected using forward feature selection procedure or other feature selection algorithm. Features that contribute the most to detection of mastication are identified (selected) at this step. Step 406 may only be needed during the initial training of the algorithm for detection of mastication. In one example, features that were selected in step 406 may be computed in step 404 after training, thus saving the power required for computation.

At step 408, the feature vectors are processed by a pattern recognition algorithm (classifier) such as Support Vector Machine, Artificial Neural Network, Decision tree, Random Forest or other. The classifier may be trained on population data to enable detection of mastication without individual calibration, or trained on individual data to provide individual-specific recognition model. A combination of these may also be used, with initial model being trained on population data and further refined on individual data. The outcome of pattern recognition is that each recognized instance of deglutition and mastication are clearly identified by a binary label (0 or 1) on a timeline. A set of useful characteristic such as duration of mastication, number of chews, and chewing rate measured over recognized mastication sequences may be useful to analyze ingestive behavior of a person.

In another implementation, a classification algorithm may use signals from mastication and/or deglutition sensors as predictors and identify periods of food consumption. The pattern recognition stage may be approached by means of a statistical method of logistic regression. The logistic regression provides not only common statistics (such as p-value) but also gives values of significance for each of the predictors and therefore indicates the relative importance of observing mastication or deglutition to characterize food consumption. Other benefits of logistic regression include small sample size to approximate normality and the fact that it cannot predict outside of the actual probability.

Logistic regression may be performed on two predictors $x_m$ and $x_d$ which denote duration of mastication and frequency of deglutition within a time window of fixed length T respectively. Instead of assuming linear model on the response variable $Y_i = \beta X_i + \varepsilon_i$ in logistic regression it is applied to so "logit" function. That is:

$$\ln \frac{p_i}{1 - p_i} = \beta x_i + \varepsilon_i,$$

or logit $p_i = \beta x_i + \varepsilon_i$, where $\beta X_i$ is a linear part with regular notation of components, i.e. $\beta = (\beta_0, \beta_1, \ldots, \beta_k)$ denotes a vector of coefficients and $x_i = (1, x_{i1}, x_{i2}, \ldots, x_{ik})$ denotes a vector of data values, and $p_i$ is $P(Y_i = 1)$. The model may then be designed to predict probability that the central point of the current window indicates food consumption, i.e. Y=1. The above formula is equivalent to $$P(Y_i = 1 \mid x_i) = p_i = \frac{e^{\beta c_i + \varepsilon_i}}{1 + e^{\beta c_i + \varepsilon_i}}.$$

To find optimal set of coefficients $\beta$ the likelihood function $$L(\beta) = \prod_{i=1}^{N} p_i^{Y_i} (1 - p_i)^{1 - Y_i}$$

may be maximized. The conditions to solving this maximization problem can be translated into the following set of equations obtained by differentiating the above equation with respect to $$\beta: \sum_{i=1}^{N} [Y_i - p(x_i)] = 0 \text{ and}$$

$$\sum_{i=1}^{N} x_{ij}[Y_i - p(x_i)] = 0, \ j = 1, 2, \ldots, p.$$

The following model provides an exemplary description of the prediction of the probability of food consumption p at central point with predictors specified above: Logit $p=\beta_0+\beta_1 x_m+\beta_2 x_d+\varepsilon$.

Several measures are applied to evaluate the goodness-of-fit, predictive power and the significance of the model. The quality of the model as a whole is represented by the difference between the null and residual deviances: $G_M=D_0-D_M$. The test of significance of $G_M$ (which under the null hypothesis is $G_M \sim \chi_k^2$) is essentially the test of: $H_0$: $\beta_1=\beta_2=\beta_3=\ldots=\beta_k=0$ versus $H_1$: at least one of $\beta$ is not equal to 0. The p-value, which is the probability that the large test statistic ($G_M$) has occurred due to a chance, i.e. p-value=P($\chi_k^2 > G_M | H_0$), can be obtained by using most statistical packages. The test of significance for any particular $\beta_j$ employs Wald test statistics which is under the null hypothesis $H_0$: $\beta_j=0$ follows standard normal distribution:

$$W_j = \frac{b_j}{S\hat{E}(b_j)},$$

where $S\hat{E}(b_j)=[\hat{Var}(b_j)]^{1/2}$. The variances and covariances of estimated coefficients are obtained from the inverse of this matrix $Var(\beta)=I^{-1}(\beta)$, where $I(\beta)$ is observed information matrix, calculated as partial derivatives matrix of second order of the log-likelihood function.

In another implementation, methods that are computationally simpler than logistic discrimination can used to detect food intake based on the detection of mastication and deglutition. For example, presence of mastication can be used as an indicator of food intake or frequency of deglutition exceeding the baseline (spontaneous swallowing frequency) by a certain proportion may be used to detect food intake. Other machine learning techniques such as decision trees, random forests or others can be used to detect food intake as well.

The detection of food intake is complicated by the fact that activities of a free-living individual are complex and unpredictable. The sensor signals may be affected by activities other than food intake and therefore be confused for intake. For example, steps taken during walking may result in acoustical signals similar to those of swallowing sounds and therefore be confused for swallowing. To alleviate the problem and to increase reliability of food intake detection, the device may employ other sensors that help in differentiating food intake from other activities. Such sensors may include the hand gesture sensor, the inertial measurement unit and others. The information provided by these sensors may be used as stand-alone (e.g. number of hand gestures is indicative of ingested volume) or in combination with jaw motion and swallowing sensors (sensor fusion).

Figure 6:
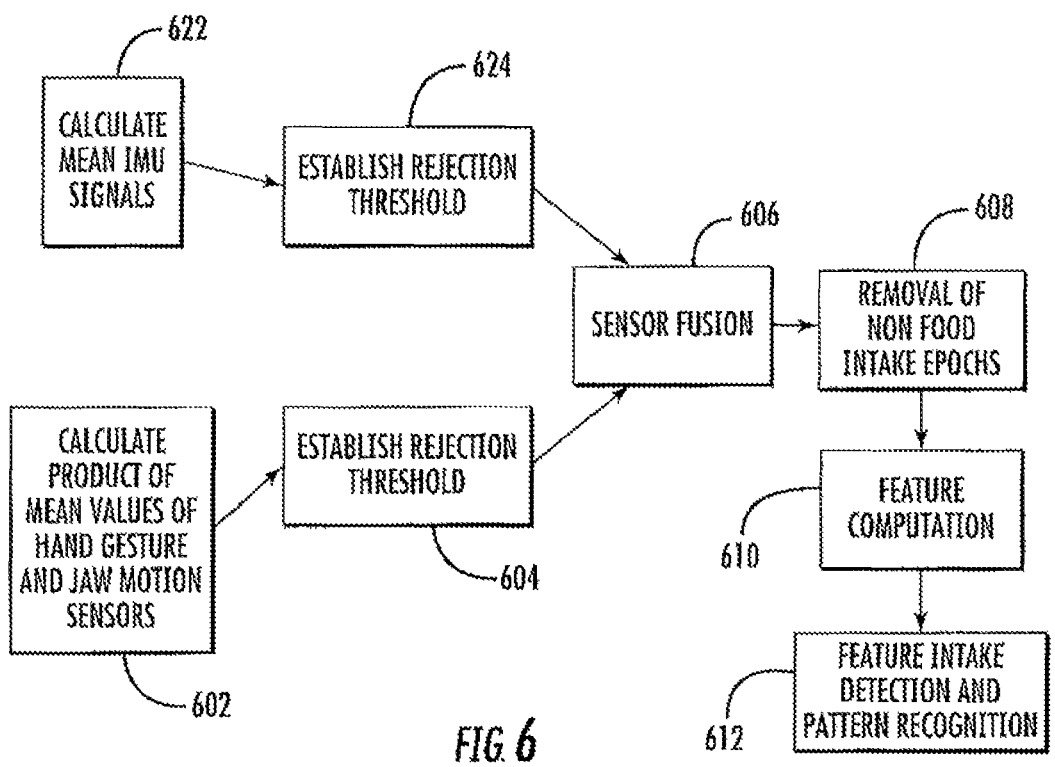
FIG. 6 illustrates a third exemplary flowchart for signal processing.

FIG. 6 illustrates an exemplary processing algorithm for detecting food intake by performing sensor fusion of jaw motion, hand gesture and inertial measurement unit signals.

The hand gesture sensor 212 on FIG. 2 may record signals indicating a gesture of bringing food to the mouth. The hand gesture senor may detect such gestures by measuring proximity of the hand to one's mouth by the means of RF or capacitive sensor, identifying orientation of the wrist in Earth's gravity field by the means of inertial measurement unit located on the wrist, detecting motion trajectory of the wrist during the gesture or combination of these measures. The outcome of hand gesture detection is an analog or digital signal HG(t) indicating hand-to mouth gestures.

The signal HG(t) may be fused with the jaw sensor signal JM(t) indicating jaw motion. The fusion may be performed to increase reliability of food intake detection and accurately differentiate food intake from other activities of daily living. The product between the absolute values of JM(t) and HG(t) may be computed at step 602 as: $SF_1(t)=|JM(t)|\cdot|HG(t)|$. $SF_1(t)$ may be divided into non-overlapping epochs $e_i$ of 30 s duration with $i=1,2,\ldots$, Ms total number of epochs for each subject S. The size selected for the epoch may present the best trade-off between the frequency of physiological events such as bites, chewing and swallowing and time resolution of food intake monitoring. The Mean Absolute Value (MAV) of the signal $SF_1(t)$ within $e_i$ may be computed as:

$$MAV_{e_i} = \frac{1}{N}\sum_{k=1}^{N}|x_k|$$

$x_k$ is the k-th sample in an epoch $e_i$ of $SF_1(t)$ containing a total of N samples. The self-report signal, PB(t), may also be divided into 30 s epochs and used to assign a class label $c_i \in \{\text{'food intake' (FI), 'no food intake' (NFI)}\}$ to each $e_i$ during training of the sensor fusion algorithm to determine the rejection threshold $T_1$. The self-report signal may not be needed during normal operation of the food detection algorithm, but only used to collect data for training of the algorithms. An epoch may be labeled as food intake if at least 10 s of self-report within the i-th epoch was marked as food intake; otherwise it was labeled as not food intake. Other durations than ten seconds may be chosen.

$SF_1/(t)$ epochs would have higher MAV during food intake due to the presence of hand-to-mouth gestures (associated with bites and use of napkins) and jaw motion activity (chewing) during eating. For that reason, a threshold level $T_1$ may be set to remove epochs in $SF_1/(t)$ belonging to activities that do not present a combination of jaw motion and hand gestures (i.e. sleeping, sitting quietly, working on a computer, watching TV, etc.).

Figure 5:
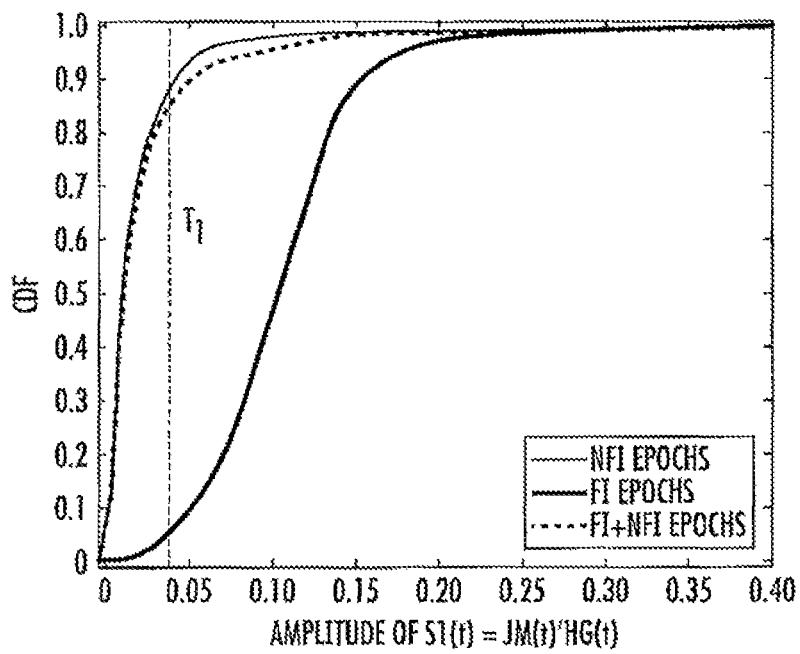
FIG. 5 illustrates an exemplary graph for monitoring food intake.

FIG. 5 illustrates the cumulative distribution function (CDF) of the MAV for food intake and not food intake epochs in $SF_1/(t)$ for one subject. The CDF represents the probability that an epoch will have a MAV less than or equal to a certain number in the x-axis. The CDF for not food intake epochs grows faster than the CDF for food intake epochs, meaning that there is a high probability to find a not food intake epoch with low MAV but a low probability to find a food intake epoch with the same MAV and vice versa. A common threshold value, $T_1$, may be determined from the population data at step 604 and the indexes of the i-th epochs having a MAV below $T_1$ may be stored in a vector $Idx_{SF1}$ indicating epochs that are not likely to be food intake. Determination of the threshold value $T_1$ from the population data may only be necessary during algorithm development and the established value of $T_1$ may be then used for anyone without a need for individual calibration or population value of $T_1$ may be used as initial estimate of threshold and then further adjusted from individual data.

Inertial measurement unit 206 on FIG. 2 may detect body motion signals. Data from sensor 206 can be used to identify when an individual is asleep to avoid recording false positives during rest. Further, individuals typically do not eat during rigorous exercise. Therefore, false positives associated with jaw motion and hand gesture signals while an individual breathes heavily and jogs, for example, can be avoided by measuring body acceleration to indicate ongoing exercise.

At step 622, the mean of the signals from the inertial measurement unit (such as 3-dimensional accelerations $ACC_X(t)$, $ACC_Y(t)$ and $ACC_Z(t)$) may be computed as:

$$SF_2(t) = 1/3 \cdot (|ACC_X(t)| + |ACC_Y(t)| + |ACC_Z(t)|)$$

$SF_2$(t) may be divided into Ms non-overlapping epochs of 30 s duration and a class label $c_i$ may be assigned to each epoch $e_i$ as in the algorithm for processing of hand gesture signal. Since most of the individuals consume foods in a sedentary position, $SF_2(t)$ epochs have higher MAV during activities involving body motion (i.e. walking, running, etc.) than during food intake. Thus, a common threshold value $T_2$ may be found for all subjects in the dataset at step 624 and the indexes of the i-th epochs in $SF_2(t)$ with a MAV above $T_2$ may be stored in a vector $Idx_{SF2}$ for further processing. Determination of the threshold value $T_2$ from the population data may only be necessary during algorithm development and the established value of $T_2$ may be then used for anyone without a need for individual calibration or population value of $T_2$ may be used as initial estimate of threshold and then further adjusted from individual data.

At step 606, sensor fusion may be performed by grouping a new vector $Idx_{SF} = \{Idx_{SF1} \cup Idx_{SF2}\} \in \Re^{D_S}$ with $D_S < M_S$ total number of epochs for each subject S. Finally, at step 608 the signals JM (t), HG (t), $ACC_x(t)$, $ACC_x(t)$, $ACC_z(t)$, and PB(t) for each subject may be divided into Ms non-overlapping epochs of 30 s duration, which were synchronized in time with $SF_1$ (t) and $SF_2$ (t) epochs. Thus, the epoch indexes stored in $Idx_{SF}$ were used to label the sensor signals epochs as non-food intake and remove them from the dataset used in the pattern recognition task. As a result, a total of $D_S$ epochs may be removed from the initial $M_S$ epochs as non-food intake epochs. The remaining epochs need to be processed by feature computation and pattern recognition steps to identify food intake epochs.

Time and frequency domain features may be extracted at step 610 from the remaining epochs of the sensor signals and combined to create a feature vector $f_i \subset \Re^{68}$ that represents an interval, such as 30 s. Each vector $f_i$ may be formed by combining features from sensor signals as: $f_i = \{f_{JM}, f_{HG}, f_{ACC}\}$, where $f_{JM} \in \Re^{38}$, $f_{HG} \in \Re^9$, and $f_{ACC} \in \Re^{21}$ represented the subsets of features extracted from JM(t), HG(t), and the inertial measurement unit (such as ACC(t)) signals respectively.

The subset $f_{JM}$ may include time and frequency domain features extracted from each epoch of the jaw motion signal, as shown in Table II below). Frequency domain features may be computed from different ranges of the frequency spectrum of JM(t) within each epoch. The subset $f_{HG}$ may include time domain features extracted from the hand-to-mouth gestures observed within each epoch (Table III).

The subset $f_{ACC}$ contained time domain features computed from the accelerometer signals from each axis (Table IV). Features may include MAV, SD and the median value of the signal as well as number of zero crossings, mean time between crossings and entropy of the signal within the epoch. The means of the MAV, SD and entropy across the 3 axes may be computed to obtain a total 21 features.

TABLE 11

FEATURES EXTRACTED FROM THE JAW MOTION SIGNAL

| # | Description |
|---|---|
| 1 | Mean Absolute Value (MAV) |
| 2 | Root Mean Square (RMS) |
| 3 | Maximum value (Max) |
| 4 | Median value (Med) |
| 5 | Ratio: MAV/RMS |
| 6 | Ratio: Max/RMS |
| 7 | Ratio: MAV/Max |
| 8 | Ratio: Med/RMS |
| 9 | Signal entropy (Entr) |
| 10 | Number of zero crossings (ZC) |
| 11 | Mean time between ZC |
| 12 | Number of peaks (NP) |
| 13 | Average range |
| 14 | Mean time between peaks |
| 15 | Ratio: NP/ZC |
| 16 | Ratio: ZC/NP |
| 17 | Wavelength |
| 18 | Number of slope sign changes |
| 19 | Energy of the entire frequency spectrum[1] (spectr_ene) |
| 20 | Energy spectrum in chewing range[2] (chew_ene) |
| 21 | Entropy of spectrum chewing range (chew_entr) |
| 22 | Ratio: chew_ene/spectr_ene |
| 23 | Energy spectrum in walking range[3] (walk_ene) |
| 24 | Entropy of spectrum walking range (walk_entr) |
| 25 | Ratio: walk_ene/spectr_ene |
| 26 | Energy spectrum in talking range[4] (talk_ene) |
| 27 | Entropy of spectrum talking range (talk_entr) |
| 28 | Ratio: talk_ene/spectr_ene |
| 29 | Ratio: chew_ene/walk_ene |
| 30 | Ratio: chew_entr/walk_entr |
| 31 | Ratio: chew_ene/talk_ene |
| 32 | Ratio: chew_entr/talk_entr |
| 33 | Ratio: walk_ene/talk_ene |
| 34 | Ratio: walk_entr/talk_entr |
| 35 | Fractal dimension |
| 36 | Peak frequency in chewing range (maxf_chew) |
| 37 | Peak frequency in walking range (maxf_walk) |
| 38 | Peak frequency in talking range (maxf_talk) |

[1]Frequency range: 0.1-500 Hz;
[2]Chewing range: 1.25-2.5 Hz;
[3]Walking range: 2.5-10 Hz;
[4]Talking range: 100-300 Hz.

TABLE 12

FEATURES EXTRACTED FROM THE HAND GESTURE SIGNAL

| # | Description |
|---|---|
| 1 | Num. of HtM gestures within epoch (num_HtM) |
| 2 | Duration of HtM (D_HtM) |
| 3 | MAV of HtM |
| 4 | Stardard Deviation of HtM |
| 5 | Maximum value (Max_HtM) |
| 6 | Wavelength (WL) |
| 7 | Ratio: WL/Duration HtM |
| 8 | Ratio: D_HtM/num_HtM |
| 9 | Ratio: MAV_HtM/D_HtM |

TABLE 13

FEATURES EXTRACTED FROM THE ACCELEROMETER SIGNALS

| # | Description |
|---|---|
| 1 | MAV of $ACC_x$ ($MAV_x$) |
| 2 | SD of $ACC_x$ (SDx) |
| 3 | Median of ACCy |
| 4 | Num. of zero crossings (ZC) for ACCx |

TABLE 13-continued

FEATURES EXTRACTED FROM
THE ACCELEROMETER SIGNALS

| # | Description |
|---|---|
| 5 | Mean time between ZC for ACCx |
| 6 | Entropy of ACCx (Entr$_x$) |
| 7 | MAV of ACCy (MAVy) |
| 8 | SD of ACCy (SDy) |
| 9 | Median of ACCy |
| 10 | Num. of zero crossings for ACCy |
| 11 | Mean time between ZC for ACCy |
| 12 | Entropy of ACCy (Entr$_y$) |
| 13 | MAV of ACCz (MAVz) |
| 14 | SD of ACCz (SDz) |
| 15 | Median of ACCz |
| 16 | Num. of ZC for ACCz |
| 17 | Mean time between ZC for ACCz |
| 18 | Entropy of ACCz (Entr$_z$) |
| 19 | Mean of {MAVx, MAVy, MAVz} |
| 20 | Mean of {SDx, SDy, SDz} |
| 21 | Mean of {Entr$_x$, Entr$_y$, Entr$_z$} |

Finally, each feature vector $f_i$ may be associated with a class label $t_i \in \{1,-1\}$, where $t_i=1$ and $t_i=-1$ represented food intake and not food intake, respectively. The same rule used in the Sensor Fusion step was used here to assign class labels to each $f_i$ vector. A dataset containing the pairs $\{f_i, t_i\}$ may be presented to a classification algorithm at step 612 for training and normal operation. The classification algorithm may one from the algorithms described above (for example, an Artificial Neural Network) or other type of machine learning algorithm.

The exemplary algorithm presented in FIG. 6 may also be adjusted for real-time recognition of food intake that follows the same or similar sequence of processing steps. The major difference is that in real-time processing a single epoch representing the sensor signals should be classified either as food intake or no food intake. Therefore, thresholds $T_1$ and $T_2$, the type of signal features to be used in classification, type and parameters of the classification algorithms as well as training of the classification algorithm have been established before use in real time.

Real time recognition of food intake enables novel, previously not possible interventions for corrections of unhealthy ingestive behaviors, such as behaviors leading to weight gain (snacking, night eating, weekend and holiday overeating) and behaviors exhibited in eating disorders such as self-limiting of food intake in cachexia due to chronic illness as well as conditions such as anorexia nervosa or binging and purging in bulimia. Feedback may be provided in real time, during the progression (or lack thereof) of an ingestive event. For example, based on the sensor signals, the amount of food that has been consumed may be calculated and a user may be warned when their food consumption for that meal or for the day has reached an optimal amount. In one implementation, an audible or visual notification may be provided on a smart phone. In another implementation, the feedback may be provided on actuator 214 of FIG. 2, such a wearable display or acoustical actuator (speaker/headphone/vibrator). As a result, users may easily track their food intake for the day. Other individuals may be notified that their food intake throughout the day has not been high enough, indicating they should eat more to gain weight. The wearable food monitoring system therefore has a wide application to individuals trying to maintain, gain, or lose weight.

Figure 7:
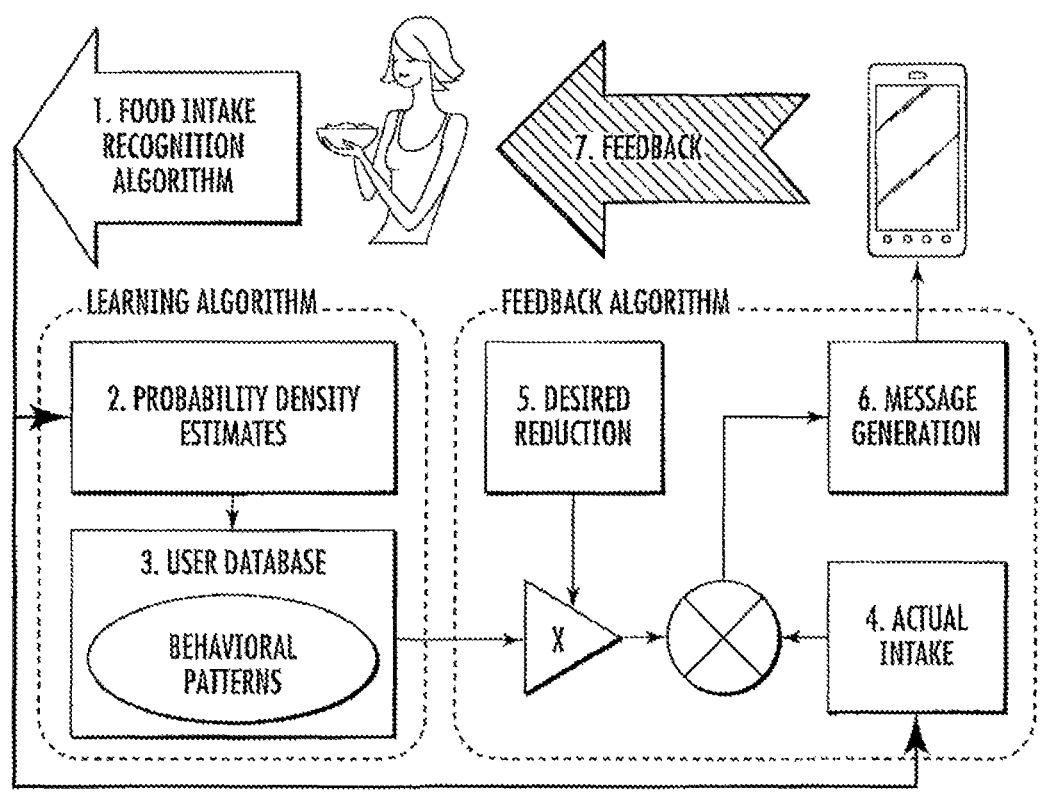
FIG. 7 illustrates an exemplary flowchart for monitoring food intake.

One exemplary algorithm for moderation of excessive food intake is shown on FIG. 7. Total energy intake of an individual during a day can be expressed as: $EI=\int \overline{D}*M(t)dt$, where $\overline{D}$ is the average energy density of that individual's diet, M(t) is mass of intake over time and t is time ($0 \le t < 24$ h). The mass of intake over time can be estimated by the system as a linear function of number of food intake epochs $N_E$, number of chews $N_{CH}$, and number of hand-to-mouth gestures $N_{HTM}$: $M(t)=a_1N_E(t)+a_2N_{CH}(t)+a_3N_{HTM}(t)+ \ldots +b$, where $a_1 \ldots a_N$ are weight coefficients for each of the contributing factors and b is the intercept. Thus, to reduce someone's energy intake by a factor $r<1$ without a change in diet composition, it is sufficient to produce feedback that will result in a proportional reduction of eating time, number of chews, and number of hand gestures.

$$rEI=\int \overline{D}*(a_1rN_E(t)+a_2rN_{CH}(t)+a_3rN_{HTM}(t)+ \ldots +rb) \, dt$$

Metrics of ingestive behavior measured by the system may be functions of time (that is, behavioral patterns of ingestion) which means that the feedback will also be a function of time and will proportionally reduce EI from the eating episodes during the day. The reduction factor r may be set at a sufficiently comfortable level to avoid the feeling of hunger or dissatisfaction, for example, by reducing daily caloric intake by 10%-20%. The individual behavioral patterns can be learned by statistical modeling techniques as described next.

Individual behavioral patterns of ingestion can be extracted from the metrics computed from the food monitor data, such as various combinations of: number of swallows, swallowing frequency, relative increase in swallowing frequency in relation to baseline, number of chews, chewing rate, intensity of chewing, number of hand gestures, hand gesture rate and timing of hand gestures, number of detected food intake epochs and so on. In one exemplary implementation, Gaussian kernel smoothing may be used to obtain non-parametric probability density estimates (PDEs) for time distribution of number of chews $N_{CH}(t)$, number of hand-to-mouth gestures $N_{HTM}(t)$, number of food intake epochs $N_E(t)$ over 24 hours using a history of ingestion over several days (step 2 on FIG. 7). Next, $\overline{cEI}(t)$—an estimate of typical cumulative EI at time t will be derived using smoothed PDEs and modeling equations that use metrics (such as number of chews, etc.) and/or wearable camera images to estimate nutrient and caloric intake. The estimate of $\overline{cEI}(t)$ will be computed following several days of observation, stored in a database (step 3 on FIG. 7) and used by the feedback algorithm. This estimate represents typical daily patterns of ingestion. The estimate can be recomputed periodically to account for changes in ingestive behavior over time.

The feedback algorithm will generate actionable feedback if the current meal/snack is approaching or is exceeding desired energy intake First, every time t when food intake is detected, an estimate of actual cumulative energy intake since the beginning of the day $\overline{aEI}(t)$ may be updated from real-time system data (step 4 on FIG. 7). When food intake is detected after at least 15 minutes of no intake it will be considered a start of a new eating episode and value of $\overline{aEI}(start)$ will be recorded. Second, a desired cumulative intake at time t will be computed from learned behavioral patterns and a desired reduction coefficient r (where $r<1$) specified by the researcher as $\overline{dEI}(t)=r*\overline{cEI}(t)$. Third, a relative difference between actual and desired cumulative EI $\Delta EI(t)=(\overline{aEI}(t)-\overline{aEI}(start))/(\overline{dEI}(t)-\overline{aEI}(start))$ will be used to evaluate user's progress toward allowed energy intake and generate feedback messages that will be sent to, for example, the user's phone.

Figure 8:
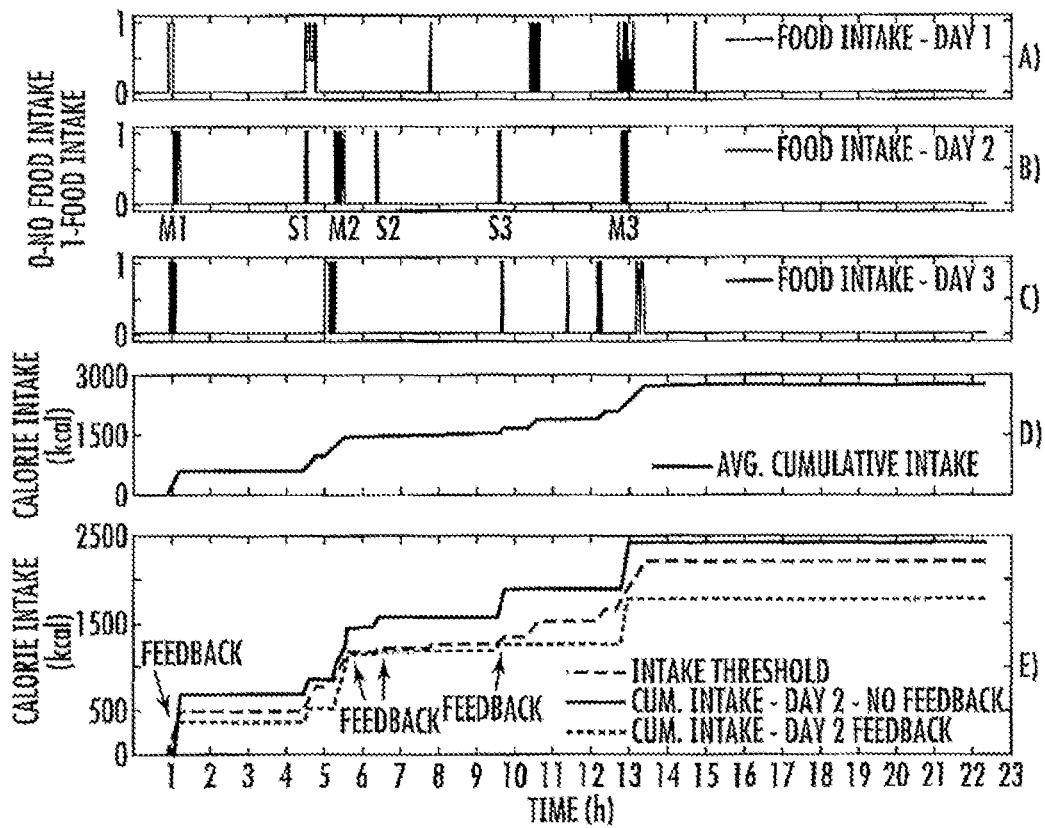
FIG. 8 illustrates examples of implementing the feedback algorithms on AIM data.

FIG. 8 illustrates the operation of learning and biofeedback algorithms. Graphs a)-c) show detected food intake for three days of observation (only $N_E(t)$ is shown). Graph d) shows learned average cumulative intake $\overline{cEI}(t)$. Graph e) shows desired intake curve $\overline{dEI}(t)$ as dashed line (r=0.8, reduction in intake of 20%), original intake for day 2 as solid line and intake after receiving feedback as dotted line. In this example, the algorithm delivers feedback in 4 out 6 eating episodes (only "stop eating" is shown). Meal 1 (M1) is reduced in size. Snack 1 (S1) is allowed as is. M2, S2 and S3 are reduced in size. M3 is allowed as is. Assuming the initial cumulative energy intake of 2400 kcal, the total estimated reduction after feedback is 500 kcal (from 2400 to 1900 kcal). In practical terms, the algorithms allow a certain amount of energy intake for each eating episode. For example, by learning typical ingestive patterns $\overline{scEI}(t)$, we know that a person usually consumes 1250 kcal in all eating episodes by the end of lunch time. If we set a reduction goal of 80% (r=0.8) then the target is consuming no more than 1000 kcal by the end of lunch time $\overline{dEI}(t)$. If this person had a 400 kcal breakfast and no snacks, then the algorithm will estimate the size of energy intake allowed for lunch as 600 kcal and feedback will be provided as the user is approaching the allowed energy intake. If the previous intake was 450 kcal, then the allowed energy intake will be estimated as 550 kcal and so on.

Various feedback messages may be used depending on the energy intake levels compared to desired levels. For example, the following feedback messages may be generated on a smart phone or wearable acoustical or tactile actuator. At $\Delta EI(t)=0.5$ (actual intake for an eating episode is at 50% of allowed EI)—one short beeps. At $\Delta EI(t)=0.75$—two short beeps (louder and higher tone). At $\Delta EI(t)=0.9$—three short beeps and vibration. At $\Delta EI(t)=1.0$—stop eating tune, vibration and screen message until snooze. At every 0.1 increase (1.1, 1.2, etc.)—stop eating tune, vibration and screen message until snooze. In general, the feedback may be provided as audio/tactile/visual alerts on a smart phone and/or wearable display, acoustical or tactile actuator indicating the action to be taken.

In other exemplary implementation, real-time feedback may be provided about rate of ingestion with goal either to slow down or to speed up the rate. The rate of ingestion may be characterized either as swallowing rate, chewing rate, hand gesture rate or a combination of these metrics. Real-time feedback may be provided during the meal to keep the ingestion rate at an optimal point for achieving satiety and reducing cumulative intake. The rate moderation feedback may be combined with the quantity moderation feedback.

In other exemplary implementation, real time feedback about calories being eaten may be provided through automatic processing of food imagery captured by food monitor's camera. Specific food items being eaten may be identified and portion size and nutrition information estimated from imagery. The feedback may be delivered as the number of calories presented on a wearable display in the field of view. The calorie estimates may overlay the food images. The recommended foods from available selection and recommended portion sizes may also be displayed over the captured food imagery. The image-based caloric intake feedback may be combined with rate moderation feedback and/or with the quantity moderation feedback based on sensor metrics.

Figure 9:
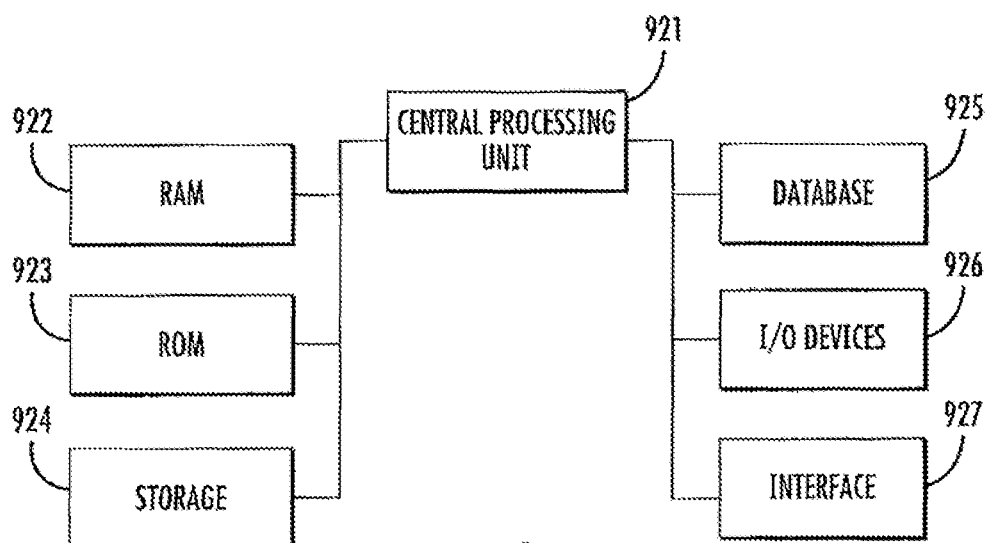
FIG. 9 illustrates an exemplary processing system consistent with various implementations.
Figure 10B:
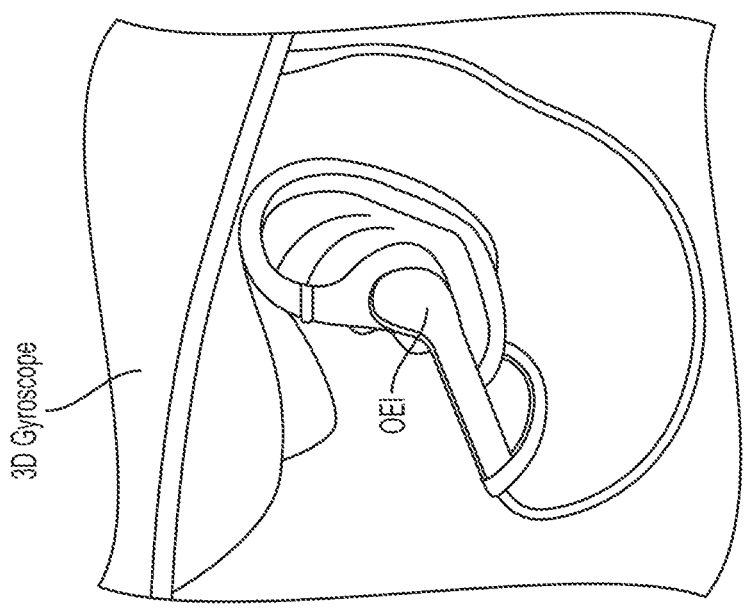
FIGS. 10A-10B illustrate PRIOR ART embodiments of pressure sensor monitors used to measure ear canal pressure for a user.
Figure 10A:
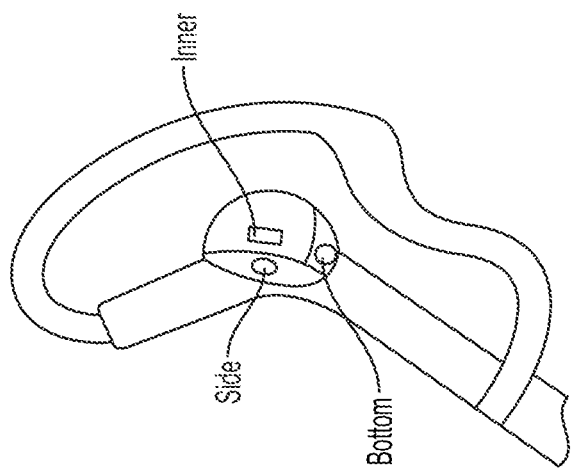

FIG. 9 illustrates an exemplary processor-based computer system, on which the disclosed methods and processes may be implemented. The overall system may involve multiple sensors communicating wirelessly. The computer may include one or more hardware and/or software components configured to collect, monitor, store, analyze, evaluate, distribute, report, process, record, and/or sort information in the disclosed implementations. For example, a controller may include one or more hardware components such as, for example, a central processing unit (CPU) 921, a random access memory (RAM) module 922, a read-only memory (ROM) module 923, a storage 924, a database 925, one or more input/output (I/O) devices 926, and an interface 927. Alternatively and/or additionally, controller 920 may include one or more software components such as, for example, a computer-readable medium including computer-executable instructions for performing a method associated with the exemplary implementations. It is contemplated that one or more of the hardware components listed above may be implemented using software. For example, storage 924 may include a software partition associated with one or more other hardware components. The controller may include additional, fewer, and/or different components than those listed above. It is understood that the components listed above are exemplary only and not intended to be limiting.

CPU 921 may include one or more processors, each configured to execute instructions and process data to perform one or more functions associated with a controller. CPU 921 may be communicatively coupled to RAM 922, ROM 923, storage 924, database 925, I/O devices 926, and interface 927. CPU 921 may be configured to execute sequences of computer program instructions to perform various processes. The computer program instructions may be loaded into RAM 922 for execution by CPU 921.

RAM 922 and ROM 923 may each include one or more devices for storing information associated with operation of CPU 921. For example, ROM 923 may include a memory device configured to access and store information associated with controller 920, including information for identifying, initializing, and monitoring the operation of one or more components and subsystems. RAM 922 may include a memory device for storing data associated with one or more operations of CPU 921. For example, ROM 923 may load instructions into RAM 922 for execution by CPU 921.

Storage 924 may include any type of mass storage device configured to store information that CPU 921 may need to perform processes consistent with the disclosed implementations. For example, storage 924 may include one or more magnetic and/or optical disk devices, such as hard drives, CD-ROMs, DVD-ROMs, or any other type of mass media device.

Database 925 may include one or more software and/or hardware components that cooperate to store, organize, sort, filter, and/or arrange data used by controller 920 and/or CPU 921. For example, database 925 the computations of signals from the various system sensors and a running count of calories consumed as estimated based on the food consumption. It is contemplated that database 1525 may store additional and/or different information than that listed above.

I/O devices 926 may include one or more components configured to communicate information with a user associated with controller 920. For example, I/O devices may include a console with an integrated keyboard and mouse to allow a user to input parameters or food intake. I/O devices 926 may also include a display including a graphical user interface (GUI) for outputting information on a monitor. I/O devices 926 may also include peripheral devices such as, for example, a printer for printing information associated with controller 920, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 927 may include one or more components configured to transmit and receive data via a communication network, such as the Internet, a local area network, a workstation peer-to-peer network, a direct link network, a wireless network, or any other suitable communication platform. For example, interface 927 may include one or more modulators, demodulators, multiplexers, demultiplexers, network communication devices, wireless devices, antennas, modems, and any other type of device configured to enable data communication via a communication network.

EXAMPLE 1

An example study monitored food intake and ingestive behavior of community-dwelling individuals and predominantly relied on jaw motion and inertial sensors embedded within a Bluetooth headset—like device to fully and automatically—without any input from the user—detect food intake accurately. The test also considered how well the equipment was configured to reject signal artifacts arising from participants' movements, talking, cell phone use and other activities. Twelve participants (6 Male/6 Female, aged 21-34 y, BMI 20-33 kg/m2) wore the sensors for 24 hours or longer while performing their usual activities of daily living. Participants were asked to report the time of occurrence of every food intake episode in a food journal. A subject-independent computer model for the food intake recognition was trained using machine and statistical learning techniques. The computer model analyzed time, frequency and time-frequency features of the sensor signals and labeled every 30 s of the observation period (an epoch) either as 1-'food intake' or -1-'no food intake'. Food intake predictions from the computer model were compared to data from the food journals to assess the accuracy of the proposed model in detecting food intake epochs. The accuracy was computed as an average of Positive Predictive Value (PPV) and True Positive Rate (TPR), which provide a realistic estimate of food intake detection in experiments with a very high number of true negatives (no food intake' epochs). The computed accuracy of detecting food intake epochs was 89.7% (±5.5%). FIG. 8 illustrates the specific times of eating as reported by one participant (top) and the food intake episodes predicted by the computer model (bottom). The model was able to detect most of the eating episodes with a low number of false positives.

EXAMPLE 2

The food intake recognition methodology was tested both under controlled laboratory conditions and in the free-living individuals. Evaluation of the device in the wild is critical to study the practical usability of the device for real-life situations. The performance of the proposed method was evaluated at several time resolutions in models that do not require subject dependent calibration.

Data Collection Protocol

Ten participants (8 males and 2 females) volunteered for this study. The recruited population had an average age of 29.03+/−12.20 years (mean+/−STD) and average body mass index (BMI) of 27.87+/−5.51 kg/m². Participants were included if they did not report any difficulties with chewing. Participants were not paid for their participation. The study was approved by the Institutional Review Board at the University of Alabama. Participants signed an informed consent before the experiments.

Participants came for two visits on different days. The first visit consisted of a controlled laboratory experiment and the second visit consisted of a laboratory portion followed by unconstrained free-living testing. During the first visit each participant had to perform several tasks in the following order. First, there was a 5-minutes rest period (using phone or computer) which was followed by a small eating episode where a slice of cheese pizza was consumed. Eating was followed by a 5-minute period where the participants talked to the investigator. The last activity performed was walking on the treadmill for 5 minutes at a speed of 3 miles per hour (mph). Research suggest that depending on the age range, the normal walking speed is in the range of 2.8 to 3.37 mph [3] and therefore a walking speed of 3 mph was chosen. Throughout the experiment, there were no restrictions on the body or head movements of the participants. They were also allowed to talk during the meal.

Eight of the ten participants came for the second visit. The remaining two participants chose not to continue with the study. The second visit had two parts, where, in the first part participants were required to perform several movements that could potentially result in motion artifacts in the sensor signals. These movements included up down, left and right head motions, upper body (trunk) movements, raising hands and transitioning between sitting and standing. These movements were performed 5 times each, and this laboratory session took about 15 minutes in total. The laboratory part was followed by a period of unrestricted free-living where participants were asked to follow their daily routine and have at least one meal that was usually their lunch at the place of their choice such as cafeteria etc. Total duration of the free-living data collected from eight participants was about 23 hours, or approximately 3 hours per person. Participants were required to keep a log of their eating episodes only. Out of 23 hours of free-living data about 3 hours were spent on eating. Since we were mostly interested in the ability of the system to detect food intake, users were not required to keep record of their other activities. During the free-living part, there were no restrictions where the participants obtained their food, the type of foods or manner in which the foods were consumed. Food items included pizza, pasta, sandwiches, fried rice, salads, apples, oranges, nuts and beverages such as water, soda and orange juice. The participants were asked to report all eating events (both solids and liquids).

Sensor System and Annotation

The wearable sensor system used in this study consisted of a small sensor module which housed a low-power 3D accelerometer (ADXL335 from Analog Devices, Norwood, Mass., USA) and a Bluetooth module (RN-42). The sensor module was connected to the right temple of non-corrective eyeglasses by heat-shrink tube (FIG. 1).

Data from the accelerometer was sampled at 100 Hz by a microprocessor (MSP430F2418, Texas Instruments, Dallas, Tex., USA). Collected data from the accelerometer were wirelessly transmitted to an Android smartphone via the Bluetooth module. The data were processed offline for algorithm development and evaluation. Participants used a pushbutton (FIG. 1) to mark consumption of solid and liquid foods. For solid foods, participants were asked to press the button at the moment when the food was placed in the mouth (a bite), and hold the button until the last swallow related to a given bite. For liquids, they were instructed to press the button from when they brought the liquid to their mouth (a sip from the container or straw) until last swallow. Pushbutton signals were used as a reference for the development of signal processing and pattern recognition algorithms.

The working principle of the proposed sensor relies on the detection of temporalis muscle activity during chewing and other facial activities. During the chewing cycle, the lower jawbone (mandible) has up-down and side to side grinding movements which results in the contraction and relaxation of the temporalis epidermis [4]. This work used the oscillatory movements of the temporalis muscle during chewing captured by the accelerometer for detection of chewing events. The temporalis muscle also participates in the sucking, or drawing the liquids into the mouth by creating a negative pressure in the oral cavity. The accelerometer used in this work captured the acceleration in three-dimensional space across three axes i.e. $Acc_x(t)$, $Acc_y(t)$ and $Acc_z(t)$ axes. Net acceleration $Acc_{Net}(t)$ was computed from the accelerometer signals:

$$Acc_{Net}(t) = \sqrt{(Acc_x(t)^2 + Acc_y(t)^2 + Acc_z(t)^2)} \quad (1)$$

Feature Extraction

A high-pass filter with a cutoff frequency of 0.1 Hz was used to remove the DC component from the signal, and the signals were normalized to compensate for inter-subject variations [5]. For feature computation, signals were divided into non-overlapping fixed time segments/window called decision epochs. Epoch duration determined the time resolution of the chewing detection. Our previous studies have used the epoch duration of the 30 s for piezoelectric strain sensor placed on the jaw [3] and 3s for piezoelectric strain sensor placed on the temporalis muscle [4]. In [7], we have shown that an epoch size <5 s is desirable to preserve information about the meal microstructure (eating bouts). To determine the best epoch duration for detection of chewing using the accelerometer signals, this work explored seven durations i.e. 3 s, 5 s, 10 s, 15 s, 20 s, 25 s, and 30 s. The pushbutton signals were used for assignment of labels to each epoch. If more than half of an epoch belonged to food intake, the epoch i was assigned a label $C_i$='1' (food intake), otherwise the label $C_i$='−1' (no food intake).

For each of the 3 axes of accelerometer and the net acceleration signal, a set of 38 features were computed for $i^{th}$ epoch. The corresponding feature sets were represented by $f_{i,x}$, $f_{i,y}$, $f_{i,z}$, and $f_{i,Net}$ for $Acc_x(t)$, $Acc_y(t)$, $Acc_z(t)$ and $Acc_{Net}(t)$, respectively. The feature vectors contained a combination of time and frequency domain features. Time domain features consisted of 1) the number of zero crossings per epoch, 2) the number of peaks per epoch, 3) mean, median, the standard deviation of the epoch data. Frequency-domain features consisted of features related to the frequency spectrum such as entropy and the standard deviation of the spectrum and the peak frequency of the spectrum. For frequency domain features, the signals were filtered in three different frequency bands which have been found to correspond to different activities i.e. 1.25-2.5Hz contains information about chewing, 25-100 Hz contains information about physical activity such as walking and 100-300 Hz contains information about speech [8], [9]. Details of these features are given in [5]. The final feature vector for the $i^{th}$ epoch was formed by concatenated the corresponding feature vectors i.e. $f_i = \{f_{i,x}, f_{i,y}, f_{i,z}, f_{i,Net}\}$, which resulted in a vector with 152 features. The computed features along with the labels for each epoch were used for training of different classification models to detect food intake.

Feature Selection and Classification

To reduce redundancy in the computed features and avoid overfitting, a two-stage feature selection procedure was used. In the first stage the computed features were ranked based on their mutual information (relevancy and redundancy measurements) using the minimum Redundancy and Maximum Relevance (mRMR) [10]. The mRMR selection can be used for both continuous and discrete datasets. The second stage applied Forward Feature Selection (FFS) to the top-ranked 30 features selected by mRMR. The combination of mRMR and/FFS is a common way of practical utilization of mRMR in feature selection [10]. For classification, a k-nearest neighbor (kNN) classifier with k=10 (found to give best results in initial experimentation) was used. The distance metric used for kNN was Euclidean distance. Separate classification models were trained, one for each epoch size.

Feature selection and classification were performed in a leave-one-out cross-validation procedure. During the 10-fold cross validation, features from 9 participants (training set) were first ranked using mRMR. Next, the subset of top 30 features was further reduced by FFS, applied in a 5-fold cross validation performed on the training data, where average classification accuracy was used as the selection criterion. The final set of features was used to train a classifier that was tested on the participant excluded from the training set (the $10^{th}$ participant). This ensured that the test data is not used in the feature selection. For the test participant, the accuracy was evaluated separately on laboratory and free-living data. The cross-validation procedure was repeated 10 times such that data from each participant was used for testing once. The F1-score (weighted average of precision and recall) was used as the measure of classification accuracy:

$$F1 = 2*Precision*Recall/(Precision-Recall) \quad (2)$$

$$Precision = TP/(TP+FP) \quad (3)$$

$$Recall = TP/(TP+FN) \quad (4)$$

where TP, FP, and FN denote true positives, false positives, and false negatives, respectively. Reported results are the average values for across test sets (10 test sets for laboratory part and 8 sets for free-living part). By choosing the F1 measure for evaluation of the classification models, the true negatives (non-food intake epochs) were not considered. Duration of food intake is relatively short (a few percent) part of daily life and inclusion of true negatives in the accuracy metrics would artificially inflate the performance of the classification models.

Results

Since feature selection was performed separately for each fold of the dataset and for a given epoch size, a different number of features were selected for each fold. Overall, the minimum number of features selected for a fold was 3 whereas the maximum number of selected features was 12. For each epoch size, some of the features repeated more than once for during the 10-fold cross validation procedure. Table I shows the selected features with a frequency of 3 or more during feature selection, for each epoch size. Tables II and III show the F1-score along with the precision and recall of the kNN classifiers for different epoch size for laboratory and free-living datasets, respectively. Table IV show the combined results. The best combined result of 87.9+/−13.8% was obtained for 20 s epoch.

TABLE 15

Selected features based on the FFS procedure for different epoch durations.
First column shows the different features which were selected at least three times. The number
represents the epoch durations for which a feature was selected.

|  | X-axis | Y-axis | Z-axis | Net-Acceleration |
|---|---|---|---|---|
| Number of Zero Crossings (ZC) |  |  |  | 25 |
| Mean time between ZC | 10, 15, |  |  | 3, 15, 20, 25, 30 |
| Number of Peaks (NP) | 3, 5, 20 | 3, 5, 10, 15, 20, 25, 30 | 3, 5, 10, 15, 20, 25, 30 |  |
| Range of amplitudes |  | 3, 5, 10, 15, 20, 25 |  |  |
| Mean time between Peaks | 3, 5, 10, 15, 25 | 3, 5, 10, 15, 25 |  | 3, 5, 10, 15 |
| ZC/NP | 3, 5, 10, 15, 20, 25 | 10, 20, 25, 30 |  | 3, 10, 15, 30 |
| Slope sign changes | 3, 20, 30 |  |  | 3, 5, 10, 15, 20, 30 |
| Spectrum energy (talking frequency band) |  | 20, 25, 30 |  |  |
| abs(entropy_spectrum_chew)/abs(entropy_spectrum_walk) | 3, 5, 10, 15, 25 |  | 3, 5, | 3, |
| walking_energy/talking_energy (frequency bands) | 3, 5, 10, 20 | 3, 5, 10, 15, 20, 25, 30 |  |  |
| spectrum_energy (chewing frequency band) |  | 15, 20, 25, 30 |  |  |
| Entropy | 3 |  |  |  |

The objective of this pilot work was to propose and evaluate the ability of a single 3-axis accelerometer attached to the temple of the glasses to detect food intake in free-living individuals. This work used a heat-shrink tube to connect the sensor to the temple of regular eyeglasses without the need of special 3D printed frames to house the electronics. Connecting the sensor to regular eyeglasses without the need for special hardware (3D printed frames or Google Glass) is a viable option since about 64% of the US population uses eyeglasses. Such a system can help in improving the comfort of the user while using the device as well as potentially improve the user compliance. The sensor module presented here was based on older technology (Bluetooth 2.0). The size and form-factor of the device can be dramatically miniaturized with use of modern Bluetooth LE platform.

This work explored different epoch durations for detection of food intake. Selecting proper epoch duration is important because the epoch duration defines the time resolution of the food intake recognition and, in turn, meal microstructure [7]. For example, smaller epoch will provide better time resolution and can be helpful in detection of short eating episodes such as snacking. Longer epochs can provide better accuracy by using more data but can result in lower time resolution and inaccurate representation of the meal microstructure.

The feature selection procedure resulted in different number of features for different folds of 10-fold cross validation. There were several features common among the various folds of the selection process. Features such as number of peaks, average time between peaks, average time difference between zero crossings and slope sign changes etc. are related to the periodicity of the signal. Other selected features are associated with the spectral contents of the signals such as the spectral energy of different frequency bands of different activities (chewing, walking and talking) and entropy.

A general trend for both the laboratory and free-living results was that the performance of the classifier increased with the increase in epoch duration (decrease in time resolution) up to a certain epoch size (10 s for laboratory (F1-score: 91.5+/−5.8%) and 20 s for free-living data (F1-score: 85.8+/−11.7%)). For combined data (laboratory and free-living), there is an increasing trend until 20 s epoch size (average F1-score: 87.9+/−13.8%). Considering the range of chewing frequency (0.94 to 2.17 Hz), the epoch durations of 10 s and 20 s will ensure the presence of multiple chewing events. Recent wearable systems presented in the literature have reported food intake detection accuracies in the ranges of 80% to 99.4% in controlled laboratory studies and 89% to 96% in unrestricted free-living conditions, using a wide variety of sensors for monitoring of bites, chew and swallowing. The system presented here has a comparable accuracy with a much simpler and user-friendly sensor. The presented sensor may be suitable to study dietary intake patterns and extract information about meal microstructure, such as meal duration, number of eating bouts, etc.

The sensor was tested in both controlled laboratory setting as well as in an unrestricted free-living. The presented methodology for food intake detection was robust to account for inter-person variations. Models were trained using leave-one-out cross-validation, which ensured that participant (subject) specific calibration of the models was not required and that the models can be generalized to larger populations.

One limitation of this study is that the intake of liquids was considered together with intake of solids, as most meals are consumed mixed. This was done to ensure that the user eating behavior is not changed or restricted in any way. Although previous research suggests that there are characteristic jaw movements during consumption of liquids similar to those of chewing [9], however, further research is needed in an attempt to differentiate solid and liquid intake with the proposed approach. A single push-button for ground truth was used for both solid and liquids and, therefore, it was not possible to differentiate between solid and liquid intake events in the free-living part of the study.

Also, the ability of the device to detect food intake when the participants were physically active (such as eating while walking) was not explicitly tested. There are other approaches that can detect eating even if the user is physically active such as snacking on the move. However, that approach required sensor placed directly on the temporalis muscle [6]. Further studies will explore the long-term use of the device and will focus on issues related to user comfort and compliance.

Another limitation of this pilot study was the small sample size of 10 participants. Although, the results presented in this pilot study are promising, further studies will be conducted to replicate these results in a larger population and for longer durations. User compliance with wearing of eyeglasses for longer term monitoring needs to be tested in future studies. The use of pushbutton to provide accurate ground truth data could potentially limit consumption of certain foods that may require use of both hands. However, it is not required for actual use of the proposed device in free-living and, thus, is not a limitation of the proposed approach in general. Future research will also explore the possibility of including a camera in the device. In this case, the sensor will be used for detection of eating episodes, and the camera will be triggered based on the sensor signals to take images of the food being consumed. Computer vision techniques such as deep learning methods could potentially be used for recognition of the type of food consumed.

An added potential advantage of this device is its potential ability to recognize physical activity being performed by the participants because of the use of an accelerometer as shown in [6]. Accelerometers are a popular choice to differentiate among activities such as sitting, standing, walking, going upstairs and downstairs [11]. Thus, by using this approach, there is a possibility to use a single sensor for monitoring of both dietary intake (energy intake) and physical activity patterns (energy expenditure), and this will be the topic of further research.

This work presented a novel approach for automatic and objective detection of food intake using a single 3-axis accelerometer sensor. The accelerometer was connected to the temple of the glasses and monitored the periodic movements of the eyeglass frame caused by the contraction and relaxation of the temporalis muscle during eating. This work explored different epoch durations for determining the best time resolution. Overall, best average F1-score of 87.9% was achieved for 20 s whereas for shortest epoch size of 3 s, the average F1-score achieved was 84.7%. These results show that the proposed approach can provide accuracy comparable to other devices presented in literature without the need of using sensors that require constant contact with the skin.

TABLE 16

Precision, Recall (Sensitivity), and F1-score for different epochs, for laboratory part. All values are in percent. Epoch sizes are in seconds.

| Epoch (sec) | Precision (%) | Recall (%) | F1-score (%) |
|---|---|---|---|
| 3 | 90.3 +/− 4.9 | 92 +/− 7.2 | 90.9 +/− 4.4 |
| 5 | 90.1 +/− 7.8 | 93.6 +/− 6.7 | 91.3 +/− 5.4 |
| 10 | 90.2 +/− 11.5 | 93.9 +/− 7.8 | 91.5 +/− 5.8 |
| 15 | 84.6 +/− 13.4 | 87 +/− 20.5 | 83.6 +/− 16 |
| 20 | 88.6 +/− 16.9 | 94.8 +/− 9.0 | 90.1 +/− 11.8 |
| 25 | 84.1 +/− 23.5 | 90.6 +/− 10.6 | 83.8 +/− 18.9 |
| 30 | 83.9 +/− 16.8 | 98.3 +/− 0.1 | 89.5 +/− 10.9 |

TABLE 17

Precision, Recall (Sensitivity), and F1-score for different epochs for free-living experiments. All values are in percent.

| Epoch (sec) | Precision (%) | Recall (%) | F1-score (%) |
|---|---|---|---|
| 3 | 83.9 +/− 11.2 | 75.3 +/− 13.5 | 78.6 +/− 10.5 |
| 5 | 85.1 +/− 10.8 | 77.1 +/− 15.1 | 80.0 +/− 10.5 |
| 10 | 86.5 +/− 10.2 | 76.5 +/− 12.7 | 80.0 +/− 9.2 |
| 15 | 91.6 +/− 6.4 | 75.7 +/− 29.4 | 79.4 +/− 21.4 |
| 20 | 88.6 +/− 8.5 | 85.4 +/− 19.4 | 85.8 +/− 11.7 |
| 25 | 86.9 +/− 10.2 | 80.2 +/− 14.2 | 81.8 +/− 8.7 |
| 30 | 84.7 +/− 7.6 | 88.2 +/− 12 | 84.9 +/− 6.0 |

TABLE 18

Precision, Recall (Sensitivity), and F1-score for different epochs for combined (laboratory and free-living) results. All values are in percent.

| Epoch (sec) | Precision (%) | Recall (%) | F1-score (%) |
|---|---|---|---|
| 3 | 87.1 +/− 9.3 | 83.7 +/− 10.9 | 84.7 +/− 7.95 |
| 5 | 87.6 +/− 10.9 | 85.6 +/− 10.3 | 85.8 +/− 7.5 |
| 10 | 88.4 +/− 9.9 | 85.2 +/− 25.0 | 85.7 +/− 18.7 |
| 15 | 88.1 +/− 12.7 | 81.4 +/− 14.2 | 81.5 +/− 11.8 |
| 20 | 88.6 +/− 16.9 | 90.1 +/− 12.4 | 87.9 +/− 13.8 |
| 25 | 85.5 +/− 12.2 | 85.4 +/− 6.0 | 82.8 +/− 8.5 |
| 30 | 84.3 +/− 12.2 | 93.3 +/− 6.0 | 87.2 +/− 8.5 |

Any combination of one or more computer readable medium(s) may be utilized. The computer readable medium may be a computer readable signal medium or a computer readable storage medium. A computer readable storage medium may be, for example, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. Program code embodied on a computer readable medium may be transmitted using any appropriate medium, including but not limited to wireless, wireline, optical fiber cable, RF, etc., or any suitable combination of the foregoing.

Computer program code for may be written in any combination of one or more programming languages, including an object oriented programming language such as Java, Smalltalk, C++, or the like, and conventional procedural programming languages, such as the "C" programming language or similar programming languages. The program code may execute entirely on the computing unit.

It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

REFERENCES

[1] Dunki-Jacobs A., Harris, J L, Lemay M., Pfleiderer M., Proenca M., Utard T. Meal Detection Devices and Methods [Internet], U.S. Pat. No. 9,168,000 B2, 2015.

[2] Bedri A, Verlekar A., Thomaz E., Avva V, Starner T., Detecting Mastication: A Wearable Approach; Proceedings of the 2015 ACM on International Conference on Multimodal Interaction [Internet]; New York, N.Y., USA: ACM 2015 [cited 2015 Dec. 7] p. 247-250. (ICMI 2015).

[3] I.-M. Lee, C.-C. Hsieh, and R. S. Paffenbarger Jr., "Exercise intensity and longevity in men: The Harvard Alumni Health Study," J. Am. Med. Assoc., vol. 273, no. 15, pp. 1179-1184,1995.

[4] "Elsevier: Gray's Anatomy, 41st Edition: Standring." [Online]. Available: https://elsevier.ca/product.jsp?isbn=9780702052309. [Accessed: 2Feb. 2017].

[5] J. M. Fontana, M. Farooq, and E. Sazonov, "Automatic Ingestion Monitor: A Novel Wearable Device for Monitoring of Ingestive Behavior," IEEE Trans. Biomed. Eng., vol. 61, no. 6, pp. 1772-1779, June 2014.

[6] M. Farooq and E. Sazonov, "A Novel Wearable Device for Food Intake and Physical Activity Recognition," Sensors, vol. 16, no. 7, p. 1067, July 2016.

[7] A. Doulah et al., "Meal Microstructure Characterization from Sensor-Based Food Intake Detection," Front. Nutr., vol. 4, 2017.

[8] J. M. Fontana and E. S. Sazonov, "A robust classification scheme for detection of food intake through non-invasive monitoring of chewing," in 2012 Annual International Conference of the IEEE Engineering in Medicine and Biology Society (EMBC), 2012, pp. 4891-4894.

[9] E. Sazonov and J. M. Fontana, "A Sensor System for Automatic Detection of Food Intake Through Non-Invasive Monitoring of Chewing," IEEE Sens. J., vol. 12, no. 5, pp. 1340-1348, May 2012.

[10] H. Peng, F. Long, and C. Ding, "Feature selection based on mutual information: criteria of max-dependency, max-relevance, and min-redundancy," IEEE Trans. Pattern Anal. Mach. Intell., vol. 27, no. 8, pp. 1226-1238,2005.

[11] D. M. Karantonis, M. R. Narayanan, M. Mathie, N. H. Lovell, and B. G. Celler, "Implementation of a real-time human movement classifier using a triaxial accelerometer for ambulatory monitoring," IEEE Trans. Inf. Technol. Biomed., vol. 10, no. 1, pp. 156-167, January 2006.

What is claimed is:

1. A system for monitoring food intake, comprising:
   an air pressure sensor for detecting ear canal deformation, the sensor detecting a change in air pressure within the ear canal resulting from mandible movement;
   an automatic gain control amplifier receiving a signal from the air pressure sensor and pre-amplifying the signal pursuant to gain values;
   a processor in communication with the sensor and a memory, wherein the processor executes computer readable instructions stored on the memory, the instructions cause the processor to:
      receive a pre-amplified signal from the air pressure sensor, wherein the pre-amplified signal comprises non-overlapping decision epochs of fixed time periods each subject to the gain values;
      store the decision epochs of the signal with corresponding gain values applied by the automatic gain control amplifier;
      compare the signal and the gain values to one or more stored signal data associated with mandible movement associated with food intake; and
      in response to the signal being indicative of mandible movement associated with food intake, generate a communication signal indicating mandible movement associated with food intake.

2. The system of claim 1, further comprising at least one ear bud in fluid communication with the air pressure sensor, wherein at least a portion of the ear bud is disposable within an ear canal of a user.

3. The system of claim 2, wherein the ear bud and the air pressure sensor are coupled by a tube.

4. The system of claim 3, further comprising an earpiece housing, wherein the air pressure sensor is disposed within the earpiece housing, the earpiece housing being disposable adjacent the user's ear outside of the ear canal.

5. The system of claim 4, wherein the earpiece housing further comprises a timer subsystem, an accelerometer, a microphone, a camera, and/or a local area network communication transceiver device.

6. The system of claim 5, wherein the processor is coupled to the timer subsystem, accelerometer, microphone, camera, and/or local area network communication transceiver device.

7. The system of claim 5, wherein the processor is coupled to the accelerometer, microphone, camera, and/or local area network communication transceiver device via a wireless connection.

8. The system of claim 1, further comprising a camera for taking images of food, the camera being in communication with the processor, and wherein the instructions further cause the processor to cause the camera to acquire an image in response to the signal reflecting a probability calculated by the processor and determined as being indicative of mandible movement associated with food intake.

9. The system of claim 1, wherein the processor compares the signal to one or more stored signal patterns and gain values and generates the communication signal without manual input from an individual.

10. The system of claim 9 wherein the instructions comprise machine learning techniques to learn food intake patterns by:
    extracting features of the signal with a time-frequency decomposition method;
    constructing an initial feature vector with the features corresponding to a respective epoch;
    calculating a plurality of power spectral density coefficients from the initial feature vector;
    constructing a predictor vector with the power spectral density coefficients and the gain values for each epoch.

11. The system of claim 10, wherein the machine learning techniques further comprise:
    reducing the number of elements in the predictor vector;
    using a resulting reduced vector as an input to a neural network that calculates labels for the reduced number of the elements;
    labeling the epochs with a classification indicating a detection or absence of a swallow, and wherein the system further comprises:
    a display to display a notification to the user of the amount of food intake the user has consumed over a given period of time.

12. The system of claim 11, wherein the display is disposed remotely from the air pressure sensor and is in communication with the processor via a wireless network.

13. A computerized method for monitoring food intake, comprising:
    measuring ear canal deformation using an air pressure sensor; and determining whether the ear canal deformation is associated with food intake by using a computer configured with a processor that is connected to both memory and an automatic gain controller to perform the steps of:
receiving a signal from the air pressure sensor at the automatic gain controller and pre-amplifying the signal pursuant to gain values;
receive a pre-amplified signal from the automatic gain controller at the processor, wherein the pre-amplified signal comprises non-overlapping decision epochs of fixed time periods each subject to the gain values;
store in the memory the decision epochs of the signal with corresponding gain values applied by the automatic gain control amplifier;
compare the signal and the gain values to one or more stored signal data associated with mandible movement associated with food intake; and
in response to the signal being indicative of mandible movement associated with food intake, generate a communication signal indicating mandible movement associated with food intake.

14. The method of claim 13, further including using a camera to take images of food, wherein the camera takes the images in response to the signal being indicative of food intake.

15. The method of claim 13, further including using machine learning techniques to learn food intake patterns by:
extracting features of the signal with a time-frequency decomposition method;
constructing an initial feature vector with the features corresponding to a respective epoch;
calculating a plurality of power spectral density coefficients from the initial feature vector:
constructing a predictor vector with the power spectral density coefficients and the gain values for each epoch.

16. The method of claim 13, further comprising compiling the signal by measuring ear canal deformation by detecting a change in air pressure within the ear and after constructing the predictor vector, reducing the number of elements in the predictor vector;
using a resulting reduced vector as an input to a neural network that calculates labels for the reduced number of the elements;
labeling the epochs of the signal with a classification indicating a detection or absence of a swallow.

17. The method of claim 13, further including notifying a user of the amount of food intake the user has consumed over a given period of time.

18. An apparatus for incorporating into a housing that is configured for connecting to an air pressure sensor that detects ear canal deformation corresponding to changes in air pressure within the ear canal resulting from mandible movement, the apparatus comprising:
a circuit comprising a processor in communication with the sensor, a memory, and an automatic gain control amplifier receiving a signal from the air pressure sensor and pre-amplifying the signal pursuant to gain values;
wherein the processor executes computer readable instructions stored on the memory, and the instructions cause the processor to:
receive a pre-amplified signal from the automatic gain control amplifier, wherein the pre-amplified signal comprises non-overlapping decision epochs of fixed time periods each subject to the gain values;
store the decision epochs of the signal with corresponding gain values applied by the automatic gain control amplifier;
compare the signal and the gain values to one or more stored signal data associated with mandible movement associated with food intake; and
in response to the signal being indicative of mandible movement associated with food intake, generate a communication signal indicating mandible movement associated with food intake.

19. An apparatus according to claim 18, further comprising:
further including using machine learning techniques to learn food intake patterns by:
extracting features of the signal with a time-frequency decomposition method;
constructing an initial feature vector with the features corresponding to a respective epoch;
calculating a plurality of power spectral density coefficients from the initial feature vector;
constructing a predictor vector with the power spectral density coefficients and the gain values for each epoch.

20. The method of claim 19, further comprising compiling the signal by reducing the number of elements in the predictor vector;
using a resulting reduced vector as an input to a neural network that calculates labels for the reduced number of the elements;
labeling the epochs of the signal with a classification indicating a detection or absence of a swallow.

* * * * *